US012767695B2

(12) United States Patent
Hagiya et al.

(10) Patent No.: US 12,767,695 B2
(45) Date of Patent: Oct. 20, 2026

(54) METHOD FOR PRODUCING HUMAN PROFESSIONAL ANTIGEN-PRESENTING CELLS

(71) Applicants: AGC INC., Tokyo (JP); National Cancer Center Japan, Tokyo (JP)

(72) Inventors: Yuichiro Hagiya, Tokyo (JP); Yasushi Uemura, Kashiwa (JP); Kyoko Fukuda, Kashiwa (JP); Tatsuaki Iwama, Kashiwa (JP)

(73) Assignees: AGC INC., Tokyo (JP); National Cancer Center Japan, Tokyo (JP)

( * ) Notice: Subject to any disclaimer, the term of this patent is extended or adjusted under 35 U.S.C. 154(b) by 918 days.

(21) Appl. No.: 18/054,392

(22) Filed: Nov. 10, 2022

(65) Prior Publication Data

US 2023/0070866 A1 Mar. 9, 2023

Related U.S. Application Data

(63) Continuation of application No. PCT/JP2021/018121, filed on May 12, 2021.

(30) Foreign Application Priority Data

May 13, 2020 (JP) ................................ 2020-084821
Sep. 4, 2020 (JP) ................................ 2020-149486

(51) Int. Cl.

| | |
|---|---|
| ***C12N 5/0783*** | (2010.01) |
| ***A61K 35/15*** | (2015.01) |
| ***A61K 35/17*** | (2015.01) |
| ***A61K 39/00*** | (2006.01) |
| ***A61K 40/10*** | (2025.01) |
| ***A61K 40/24*** | (2025.01) |
| ***A61K 40/42*** | (2025.01) |
| ***A61P 35/00*** | (2006.01) |
| ***C07K 14/535*** | (2006.01) |

(52) U.S. Cl.

CPC ............ *C07K 14/535* (2013.01); *A61K 35/15* (2013.01); *A61K 35/17* (2013.01); *A61K 40/10* (2025.01); *A61K 40/24* (2025.01); *A61K 40/42* (2025.01); *A61P 35/00* (2018.01); *C12N 5/0638* (2013.01); *A61K 2239/31* (2023.05); *C12N 2501/125* (2013.01); *C12N 2501/145* (2013.01); *C12N 2501/165* (2013.01); *C12N 2501/22* (2013.01); *C12N 2506/45* (2013.01)

(58) Field of Classification Search

CPC ...... C07K 14/535; A61K 35/15; A61K 35/17; A61K 40/24; C12N 5/0638; C12N 2501/125; C12N 2501/165; C12N 2501/22; C12N 2501/2303; C12N 2502/1121; C12N 2513/00; C12N 5/0639; A61P 43/00

See application file for complete search history.

(56) References Cited

U.S. PATENT DOCUMENTS

| | | | |
|---|---|---|---|
| 9,499,789 | B2 | 11/2016 | Nakahata et al. |
| 2013/0195818 | A1 | 8/2013 | Senju |
| 2014/0212398 | A1 | 7/2014 | Reisner et al. |

FOREIGN PATENT DOCUMENTS

| | | | | | |
|---|---|---|---|---|---|
| JP | 2014-526244 | A | | 10/2014 | |
| JP | 5861191 | B2 | | 2/2016 | |
| JP | 2018171005 | A | * | 11/2018 | |
| WO | WO-2012043651 | A1 | * | 4/2012 | ................ A61P 9/00 |
| WO | WO 2018/181903 | A1 | | 10/2018 | |

OTHER PUBLICATIONS

Jin Lianhong et al., Histology and Embryology, 2004, 5 pages (with partial English machine translation).
Zhang Juntian et al., Modern Pharmacological Experimental Methods, 2012, 7 pages (with partial English machine translation).
Chinese Search Report issued Jun. 6, 2025 in Chinese Patent Application No. 2021800479527, 2 pages.
Extended European Search Report dated May 17, 2024 in corresponding European Patent Application No. 21803659.8, 11 pages.
Zhang, R., et. al. "Generation of Mouse Pluripotent Stem Cell-Derived Proliferating Myeloid Cells as an Unlimited Source of Functional Antigen-Presenting Cells", Cancer Immunology Research, vol. 3, No. 6, Feb. 11, 2015, pp. 668-677.
Haruta, M. et al., "TAP-deficient human iPS cell-derived myeloid cell lines as unlimited cell source for dendritic cell-like antigen-presenting cells," Gene Therapy, vol. 20, No. 5, May 1, 2013, pp. 504-513.
Cui, J., et al., "Dendritic cells transfected with lentriviral vector-encoding human granulocyte-macrophage colony-stimulating factor augment anti-tumour T-cell response in vitro," International Journal of Immunogenetics, vol. 37, No. 5, May 27, 2010, pp. 329-336.
Curiel-Lewandrowski, Clara, "Transfection of Immature Murine Bone Marrow-Derived Dendritic Cells with the Granulocyte-Macrophage Colony-Stimulating Factor Gene Potently Enhances Their In Vivo Antigen-Presenting Capacity," The Journal of Immunology, vol. 163, No. 1, Jul. 1, 1999, pp. 174-183.
Mashima, Hiroaki, "Generation of GM-CSF-producing antigen-presenting cells that induce a cytotoxic T cell-mediated antitumor response," Oncoimmunology, vol. 9, No. 1, Sep. 6, 2020, 16 pages.
International Search Report issued on Aug. 3, 2021 in PCT/JP2021/018121, 3 pages.

(Continued)

*Primary Examiner* — Jeremy C Flinders
*Assistant Examiner* — Masudur Rahman
(74) *Attorney, Agent, or Firm* — Oblon, McClelland, Maier & Neustadt, L.L.P.

(57) ABSTRACT

A method for producing a professional antigen-presenting cell, including inducing expression of c-MYC, BMI1, and MDM2 in a myeloid cell (MC) to obtain a proliferative myeloid cell (pMC), and inducing expression of GM-CSF and/or M-CSF in the pMC to obtain a professional antigen-presenting cell (pAPC). The myeloid cell is a myeloid cell differentiated from a pluripotent stem cell.

5 Claims, 27 Drawing Sheets

(56) References Cited

OTHER PUBLICATIONS

Written Opinion issued on Aug. 3, 2021 in PCT/JP2021/018121, 5 pages.

Palucka et al., "Dendritic-Cell-Based Therapeutic Cancer Vaccines", Immunity, Jul. 2013, vol. 39, pp. 38-48.

Yarchoan et al., "Targeting neoantigens to augment antitumour immunity", Nat Rev Cancer, Apr. 2017, vol. 17, No. 4, pp. 1-29.

Senju et al., "Generation and genetic modification of dendritic cells derived from mouse embryonic stem cells", Blood, May 2003, vol. 101, No. 9, pp. 3501-3508.

Matsuyoshi et al., "Enhanced Priming of Antigen-Specific CTLs In Vivo by Embryonic Stem Cell-Derived Dendritic Cells Expressing Chemokine Along with Antigenic Protein: Application to Antitumor Vaccination", The Journal of Immunology, Jan. 2004, vol. 172, No. 2, pp. 776-786 (12 total pages).

Hirata et al., "Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand". The Journal of Immunology, Feb. 2005, vol. 174, vol. 4, pp. 1888-1897 (11 total pages).

Hirata et al., "Involvement of Regulatory T Cells in the Experimental Autoimmune Encephalomyelitis-Preventive Effect of Dendritic Cells Expressing Myelin Oligodendrocyte Glycoprotein plus TRAIL", The Journal of Immunology, Jan. 2007, vol. 178, No. 2, pp. 918-925 (9 total pages).

Senju et al., "Genetically Manipulated Human Embryonic Stem Cell-Derived Dendritic Cells with Immune Regulatory Function", Stem Cells, 2007, vol. 25, pp. 2720-2729 (11 total pages).

* cited by examiner

[Fig. 1]
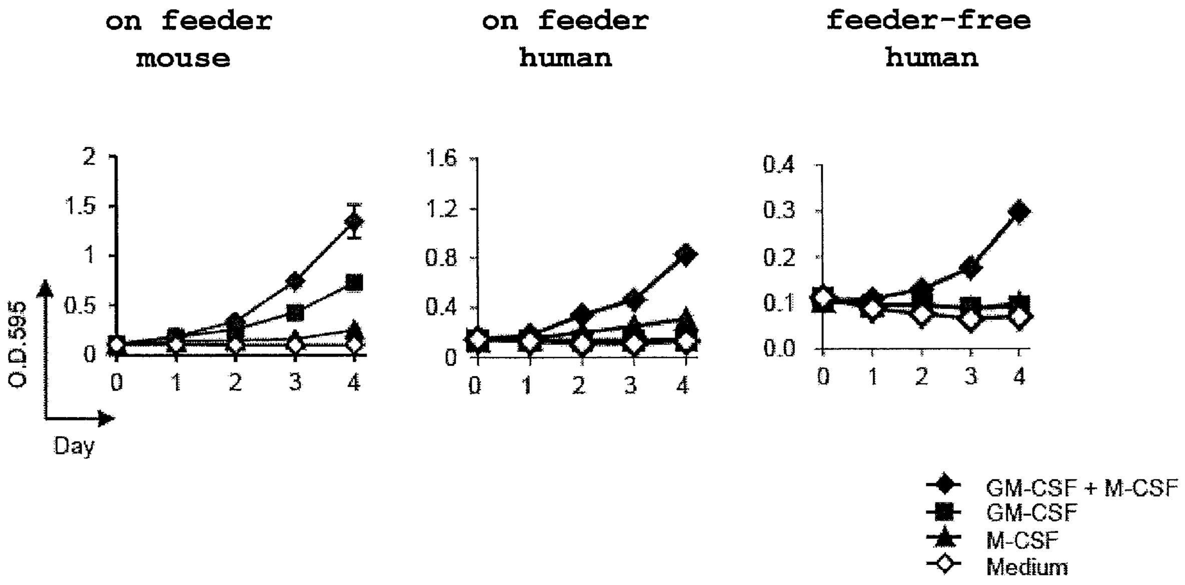
[Fig. 2]
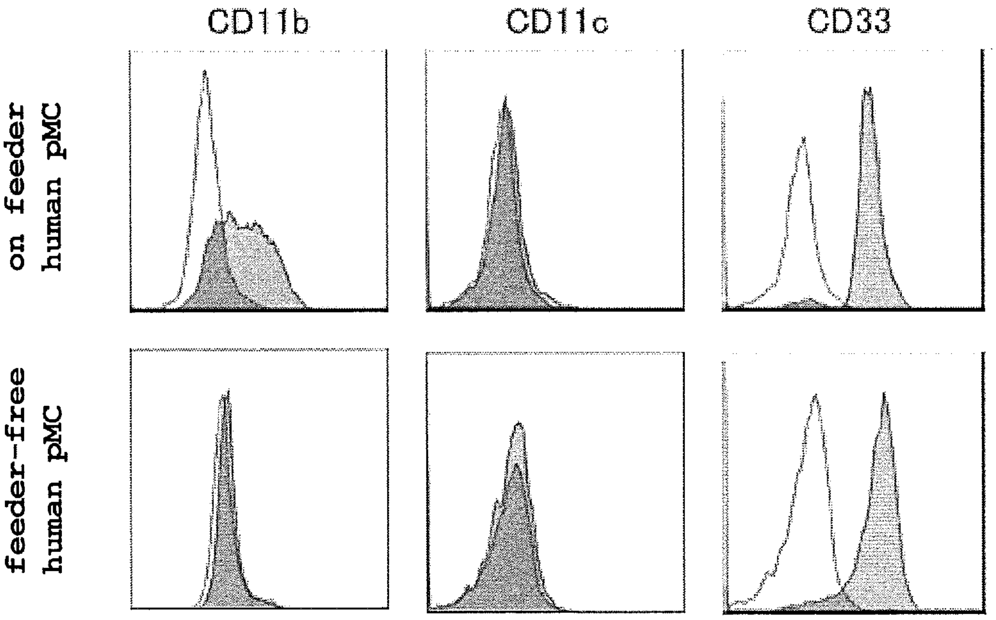

[Fig. 3]
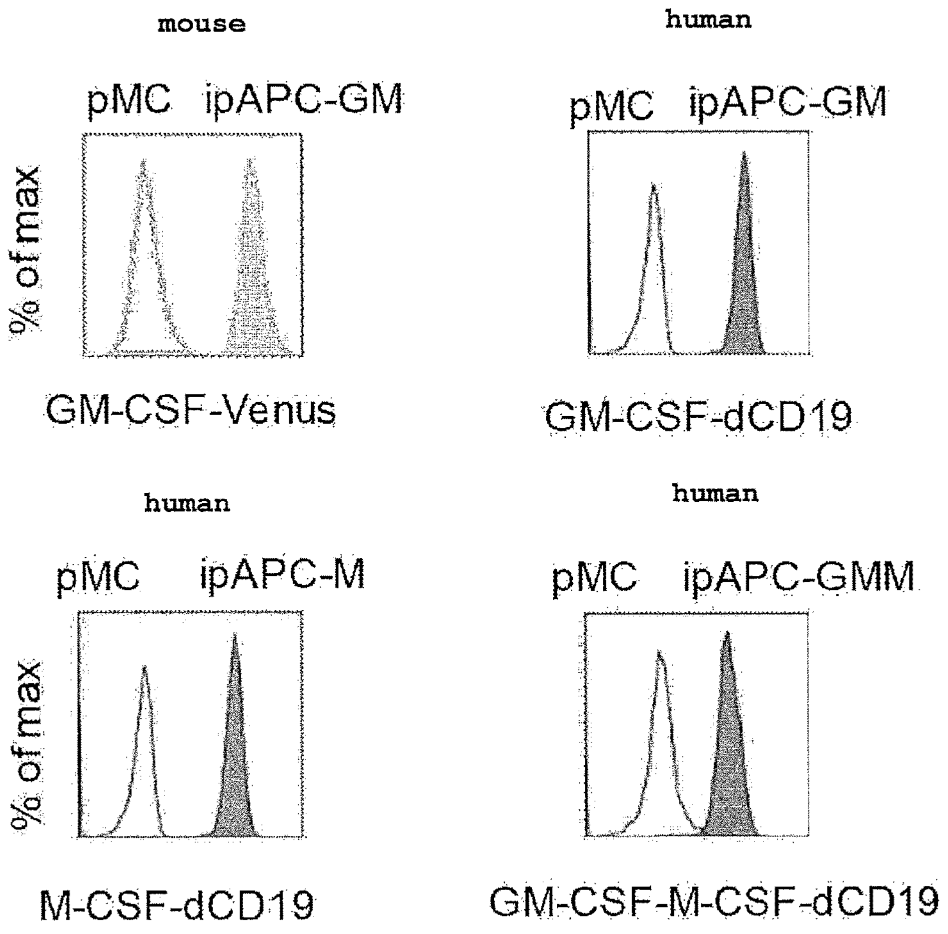
[Fig. 4]
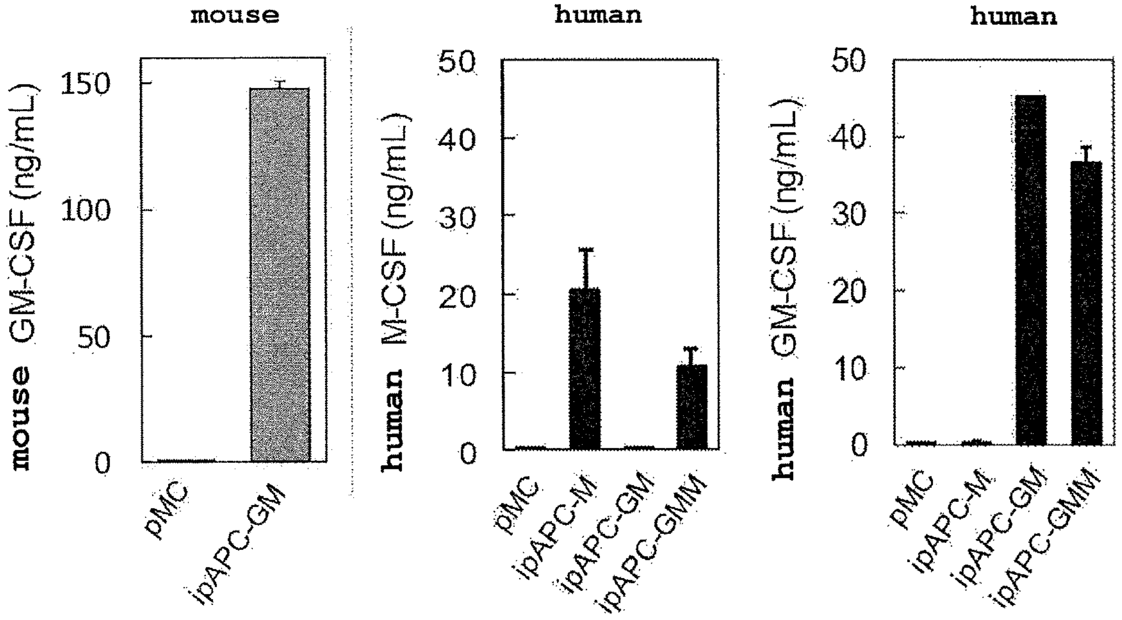

[Fig 5]
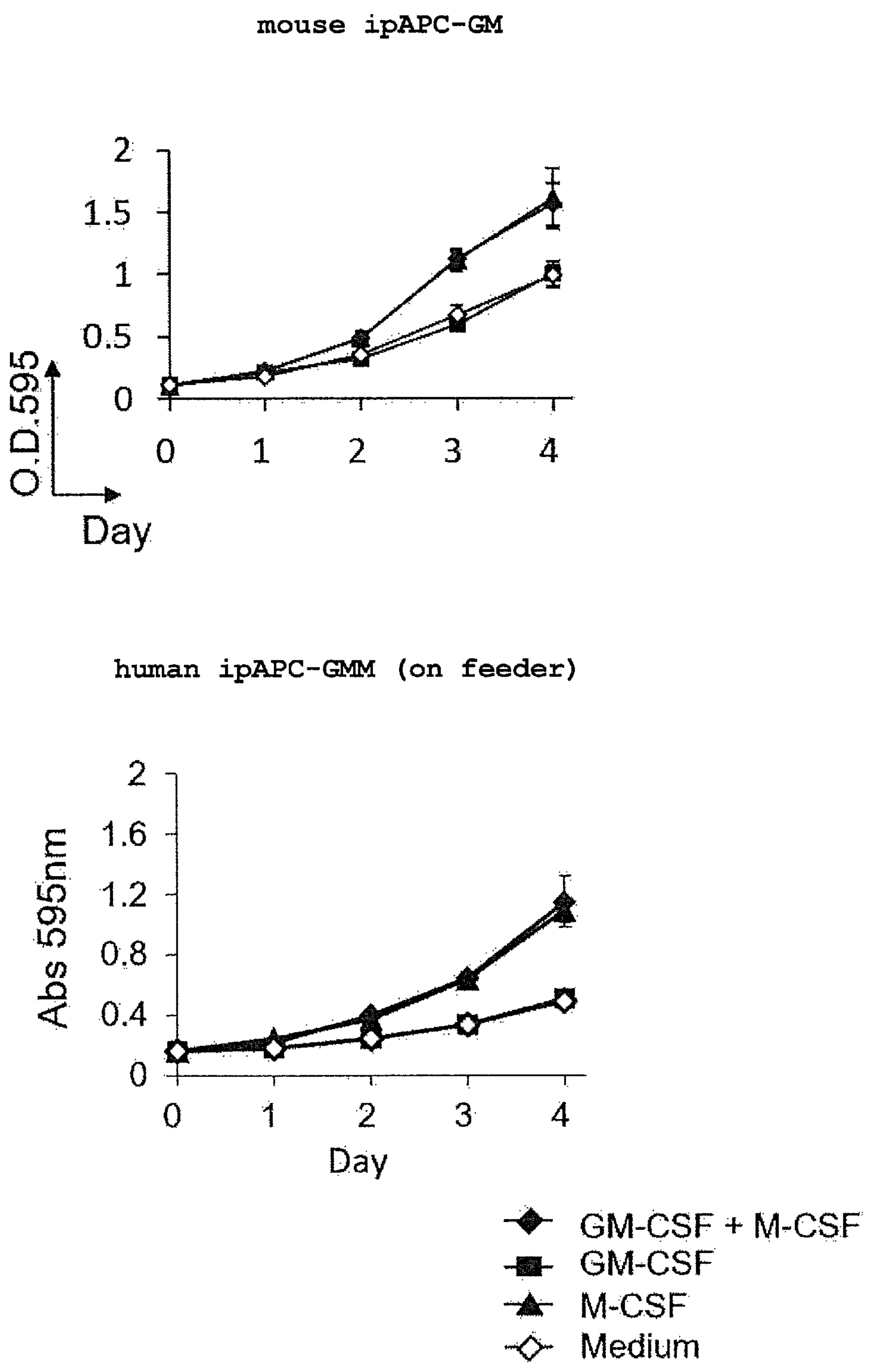

[Fig. 6]
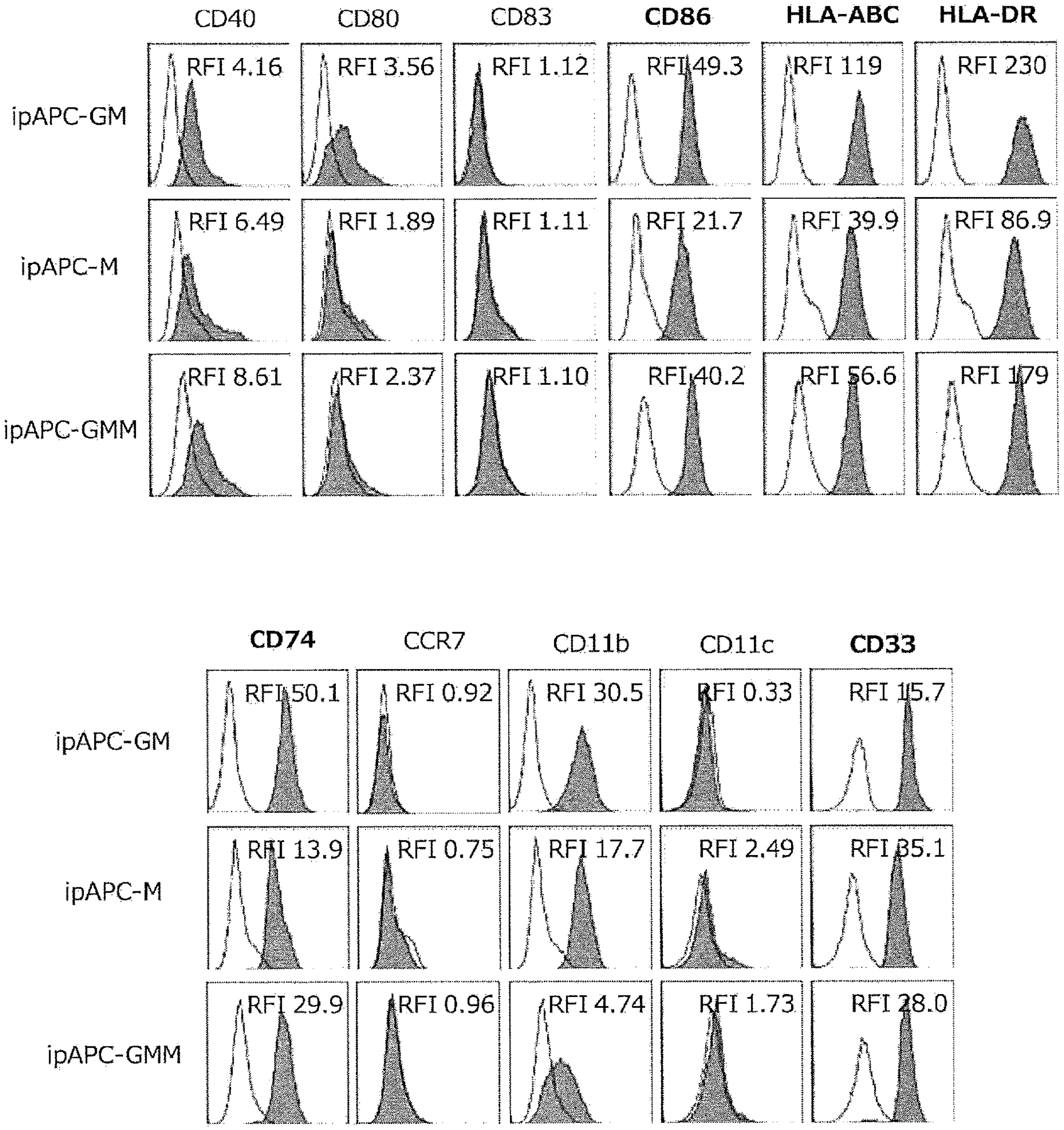

[Fig. 7]
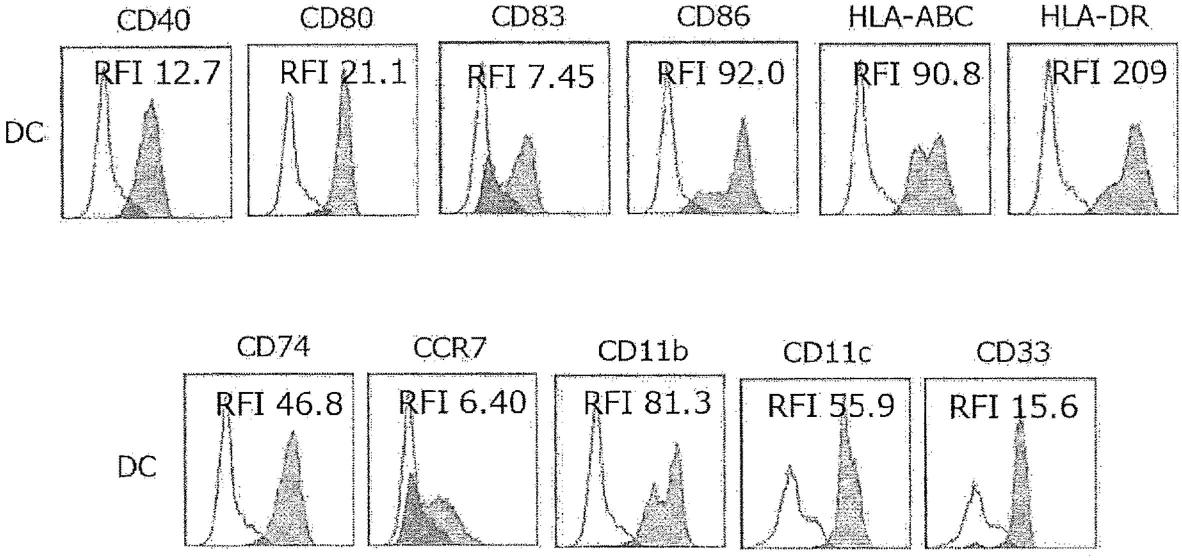
[Fig. 8]
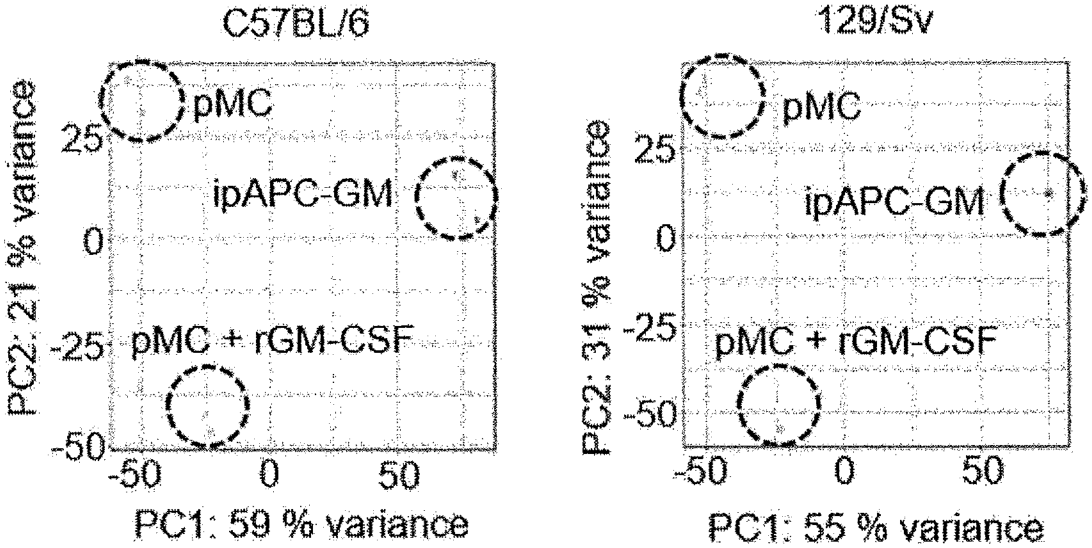

[Fig. 9]
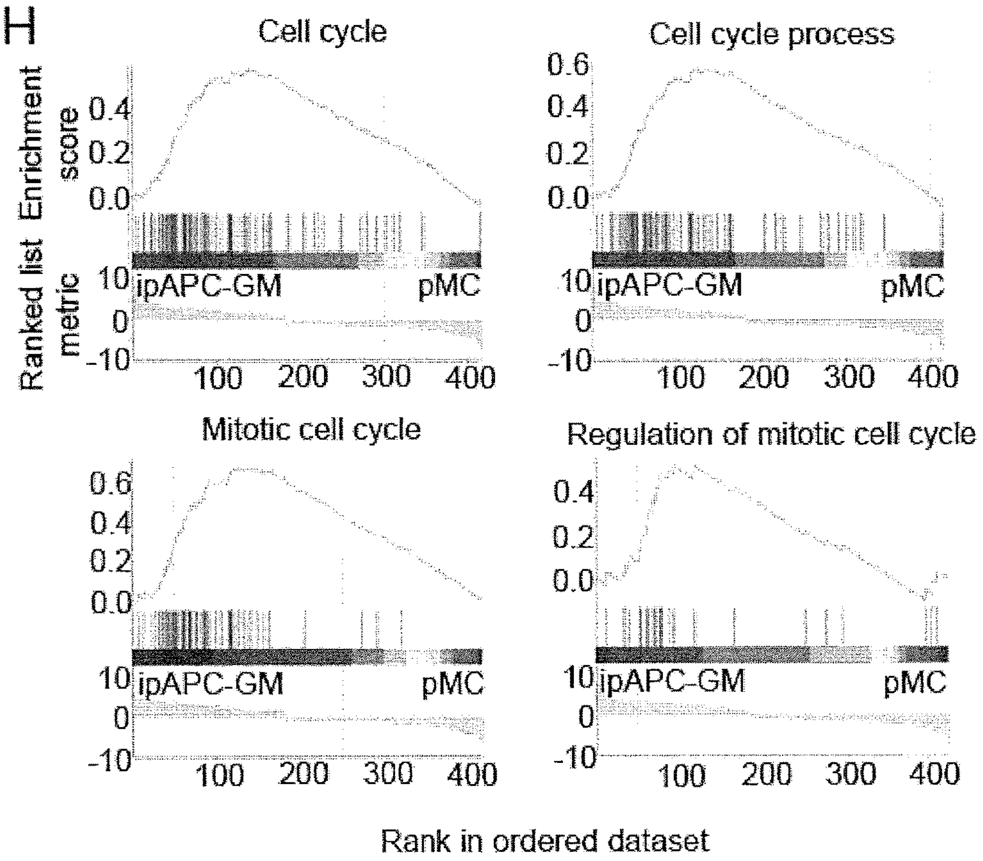
[Fig. 10A]
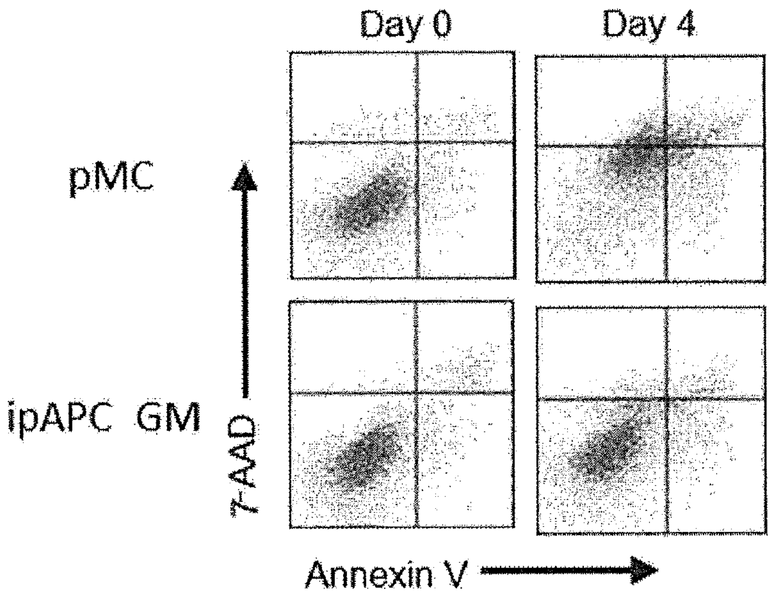

[Fig. 10B]
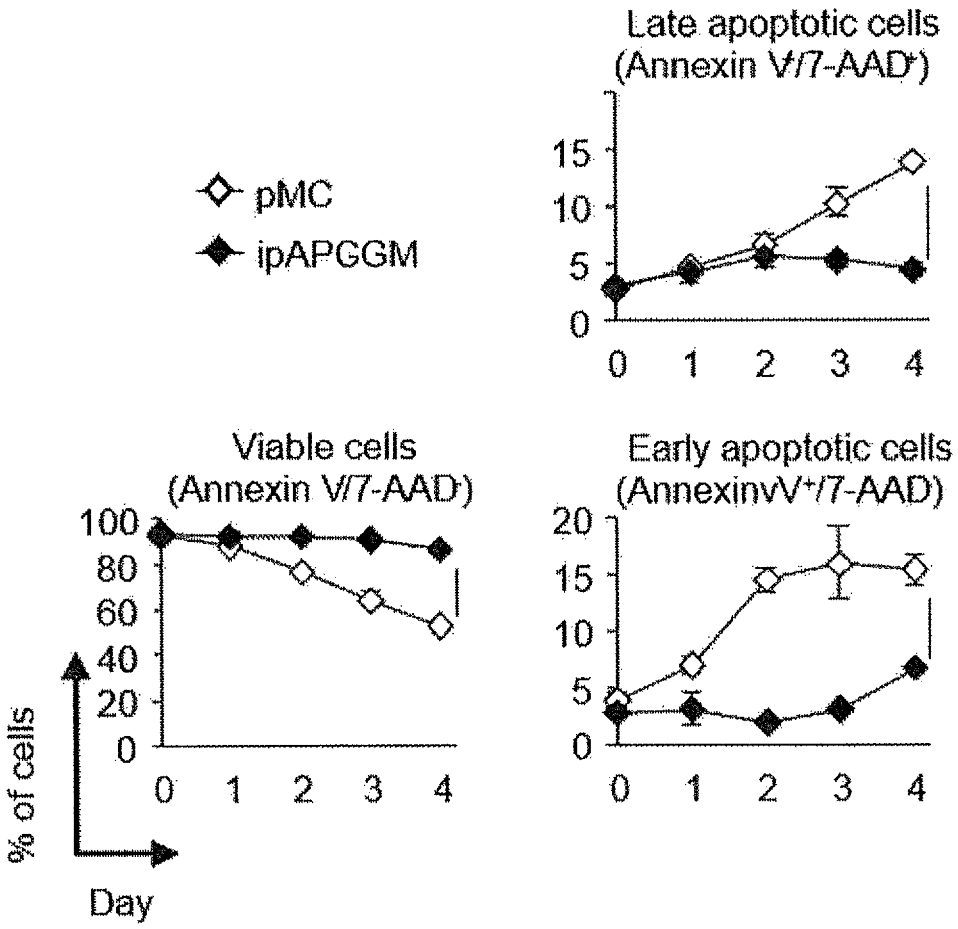

[Fig. 10C]
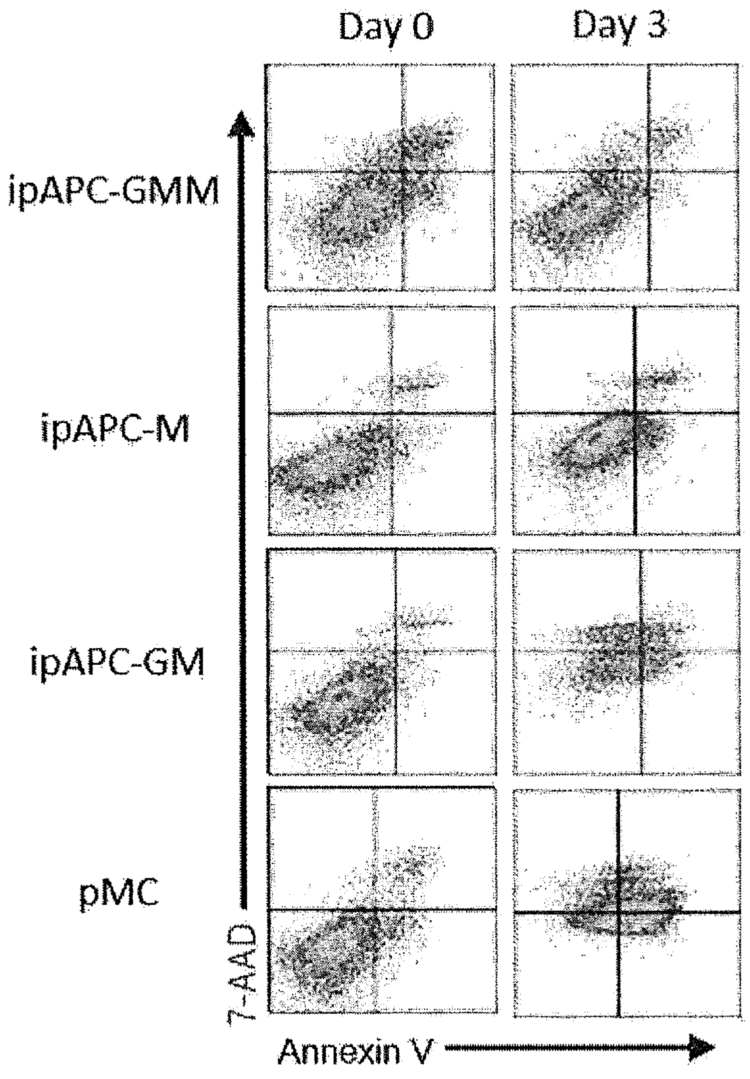

[Fig. 10D]
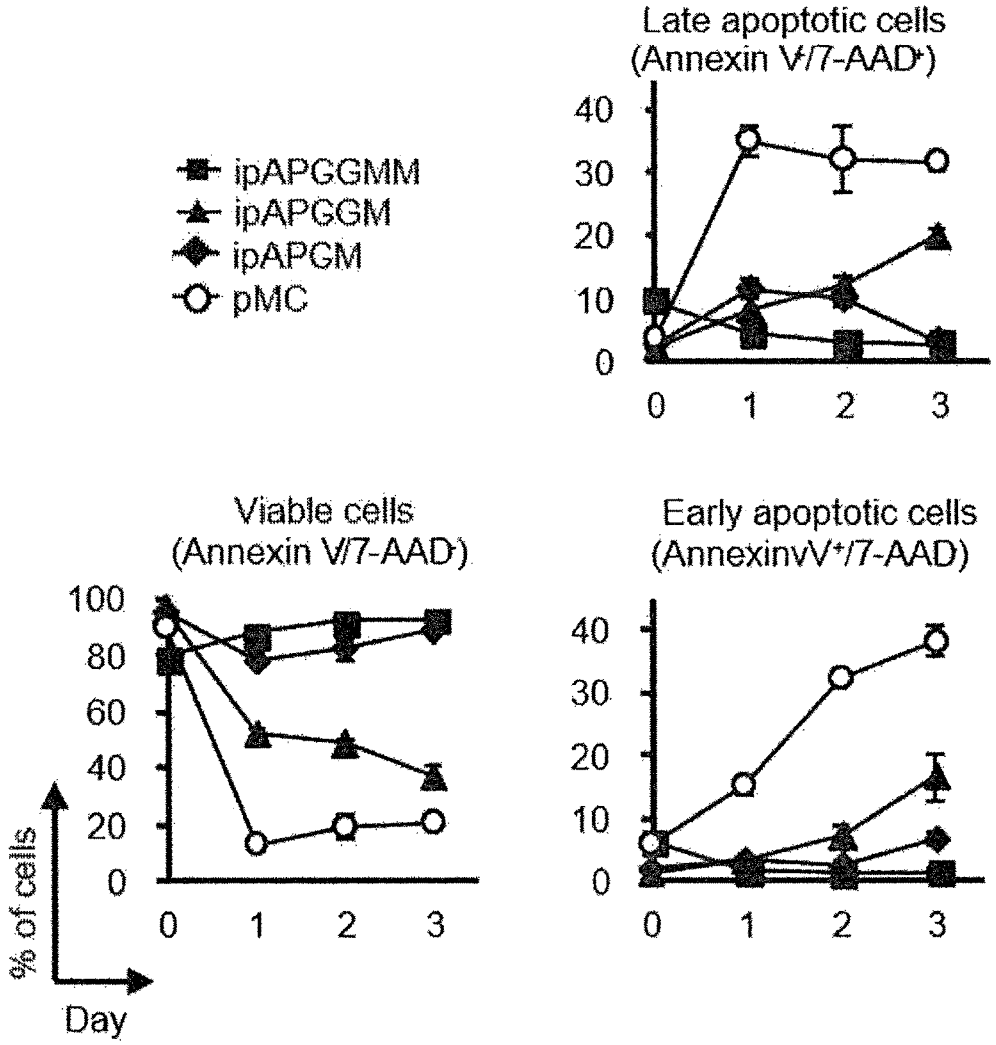
[Fig. 11]
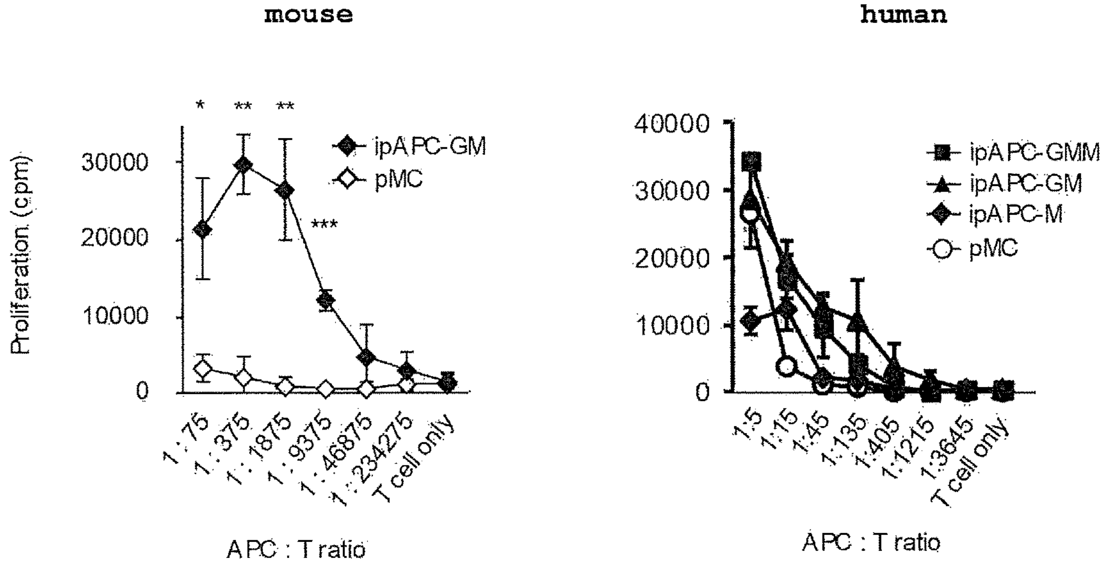

[Fig. 12A]
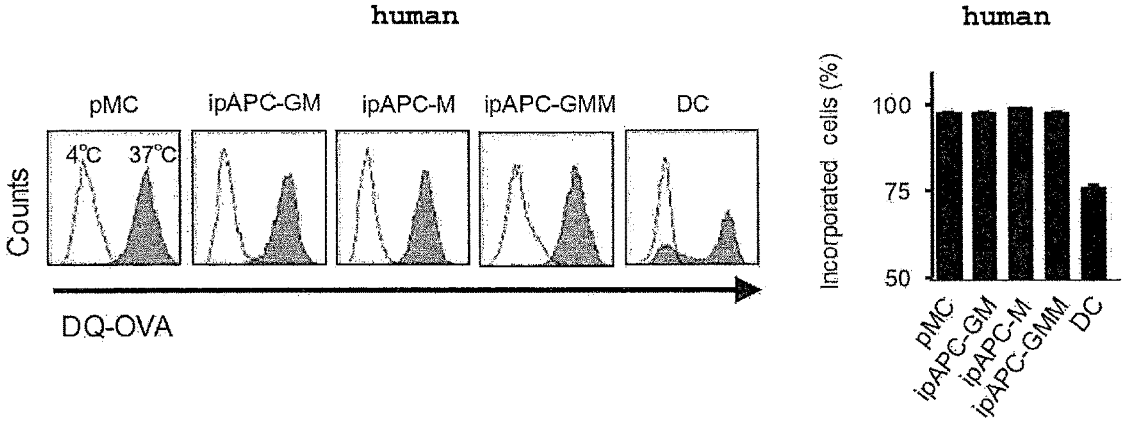
[Fig. 12B]
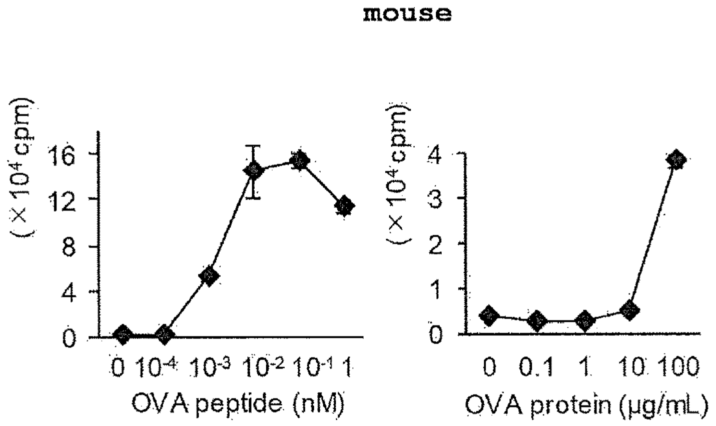
[Fig. 13]
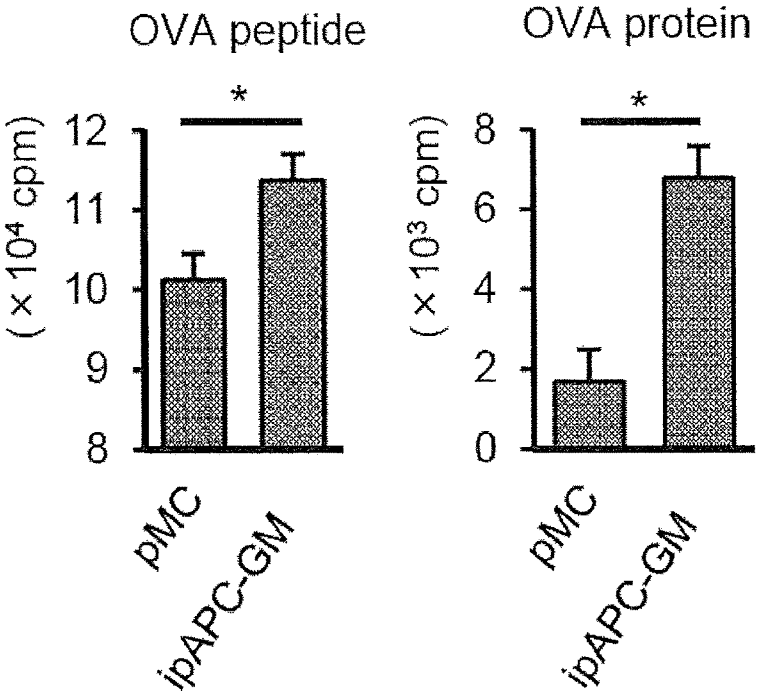

[Fig. 14]
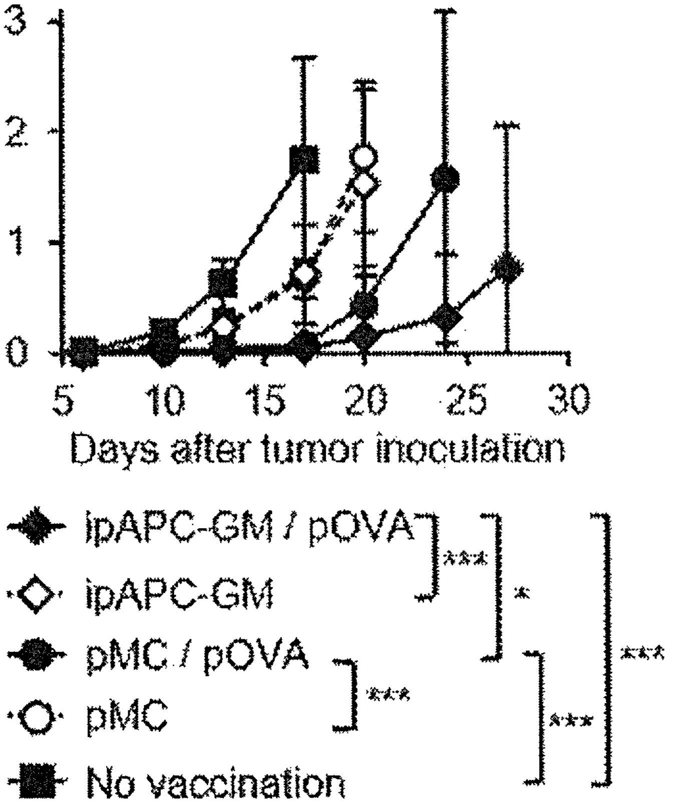

[Fig. 15]
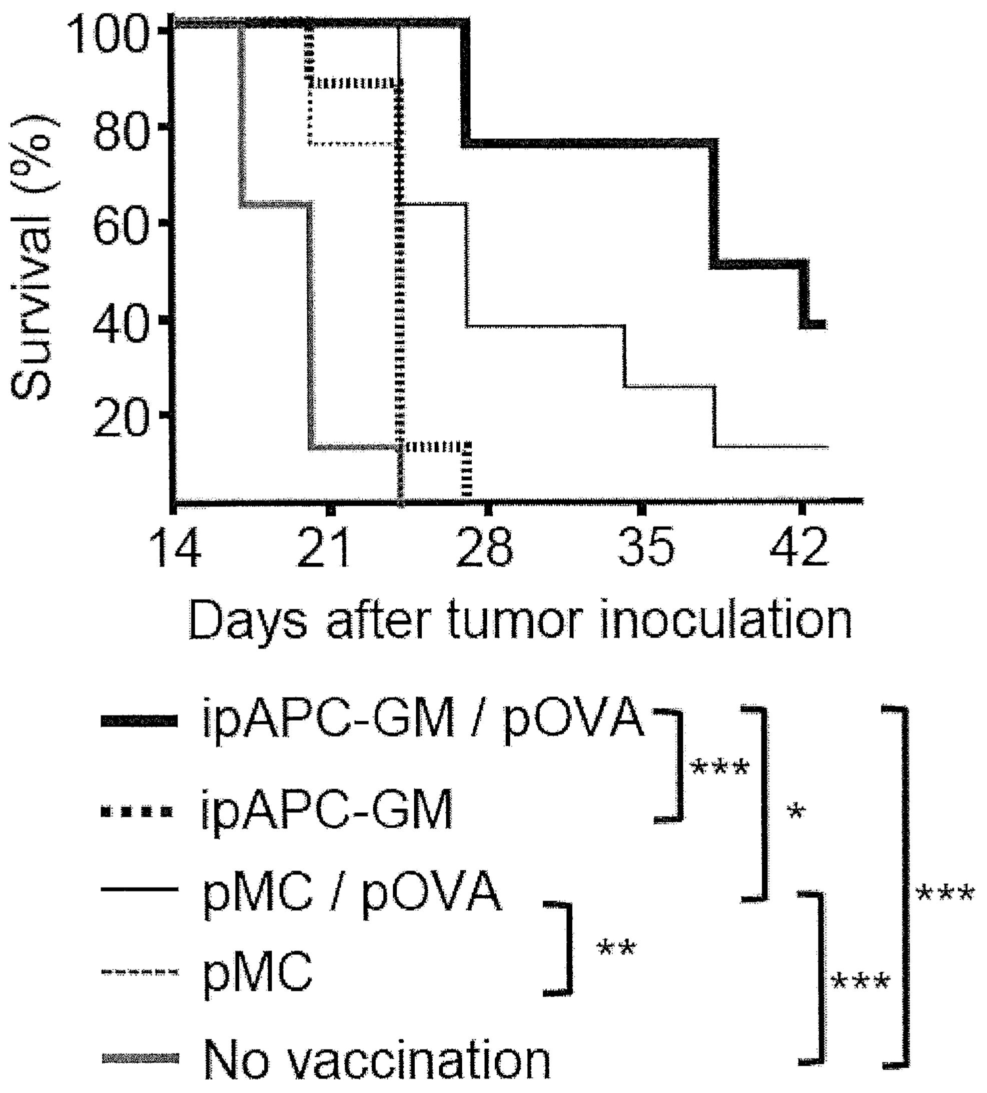

[Fig. 16]
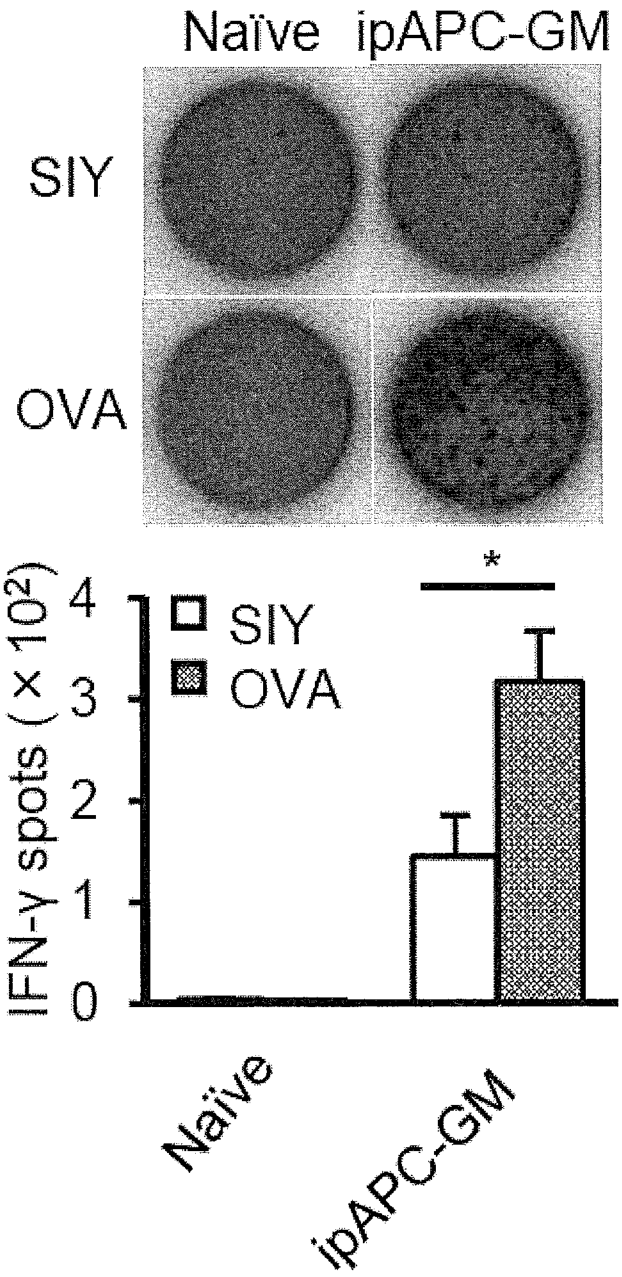

[Fig. 17]
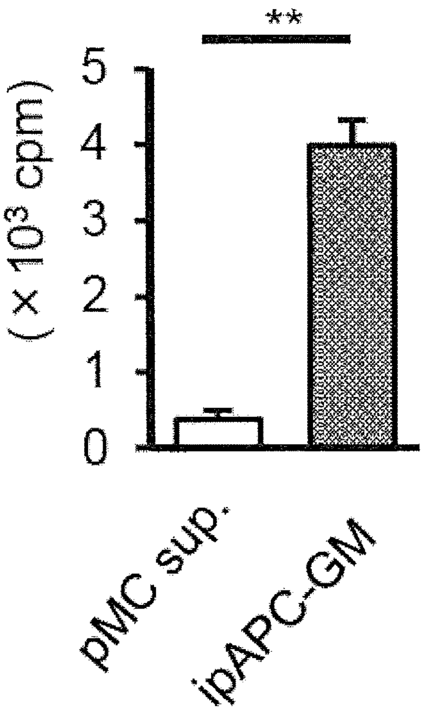
[Fig. 18]
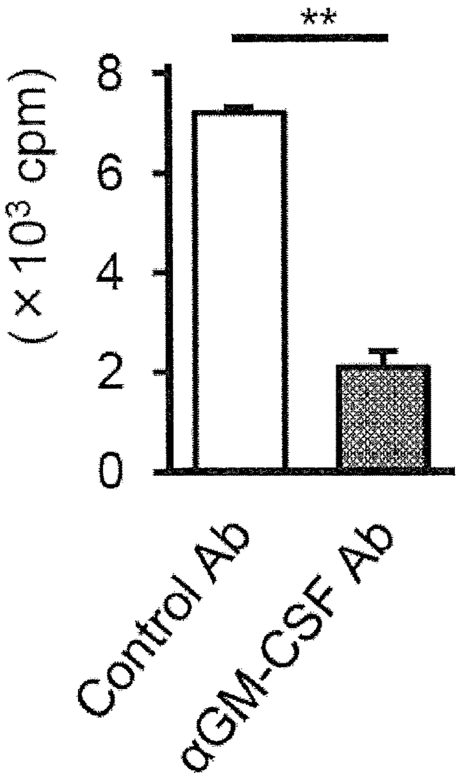

[Fig. 19]
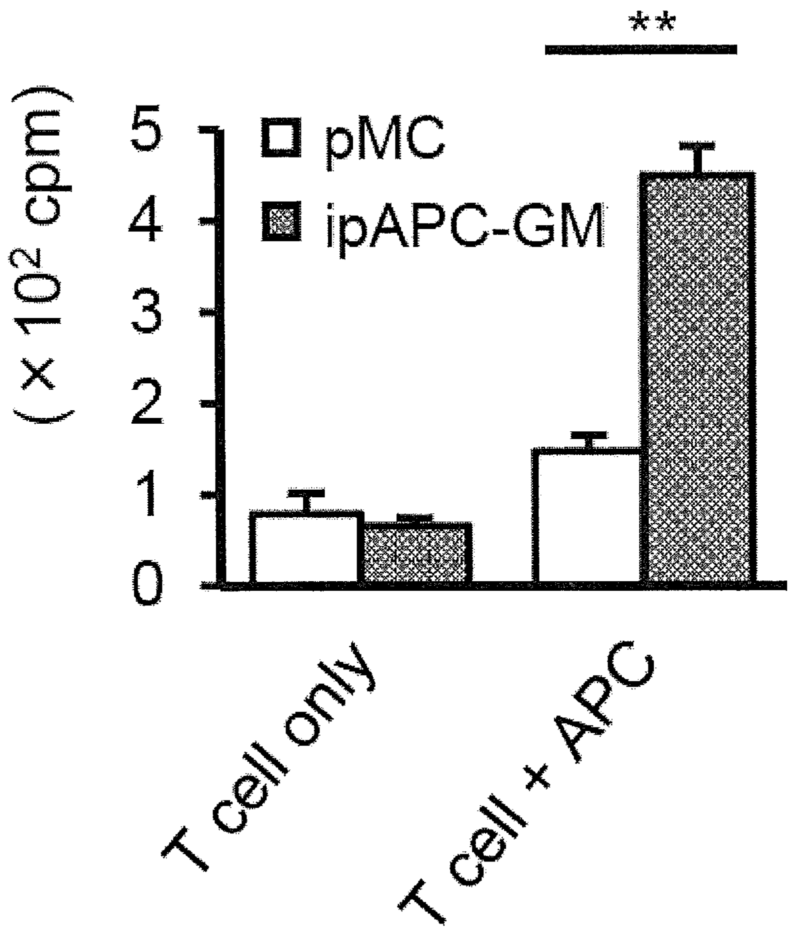

[Fig. 20]
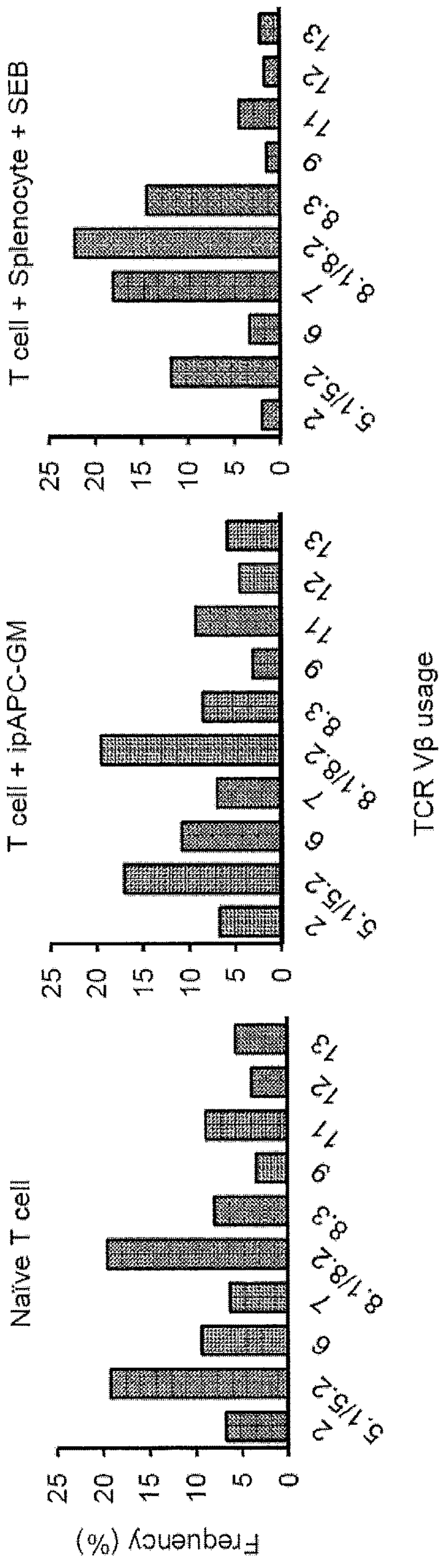

[Fig. 21]
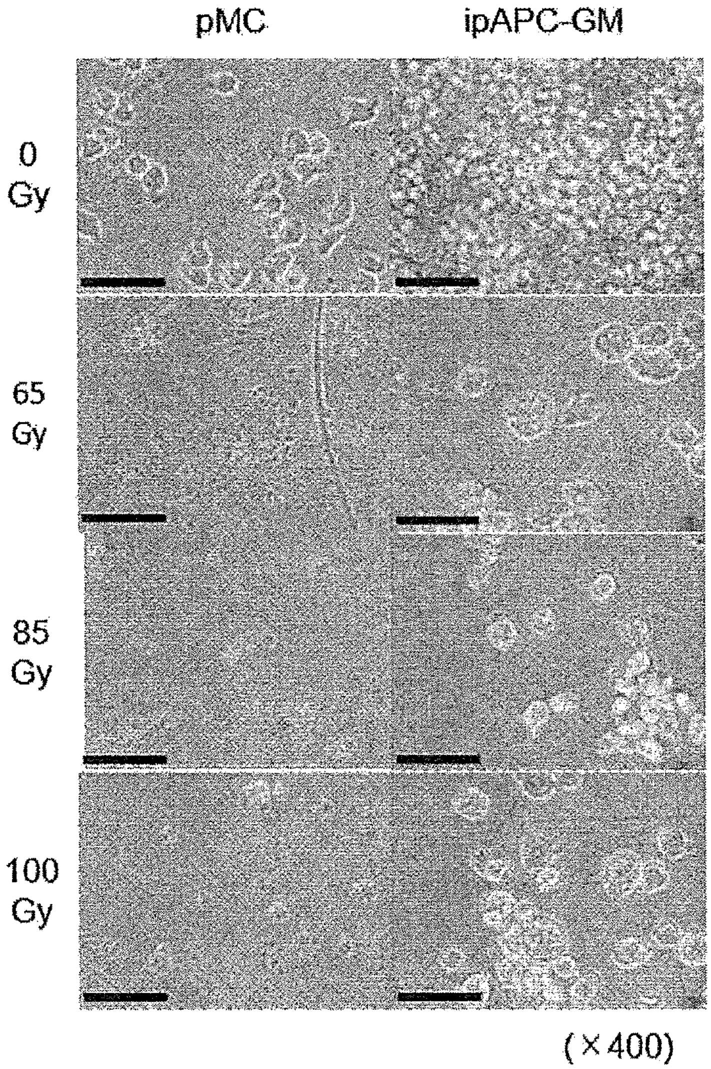
[Fig. 22]
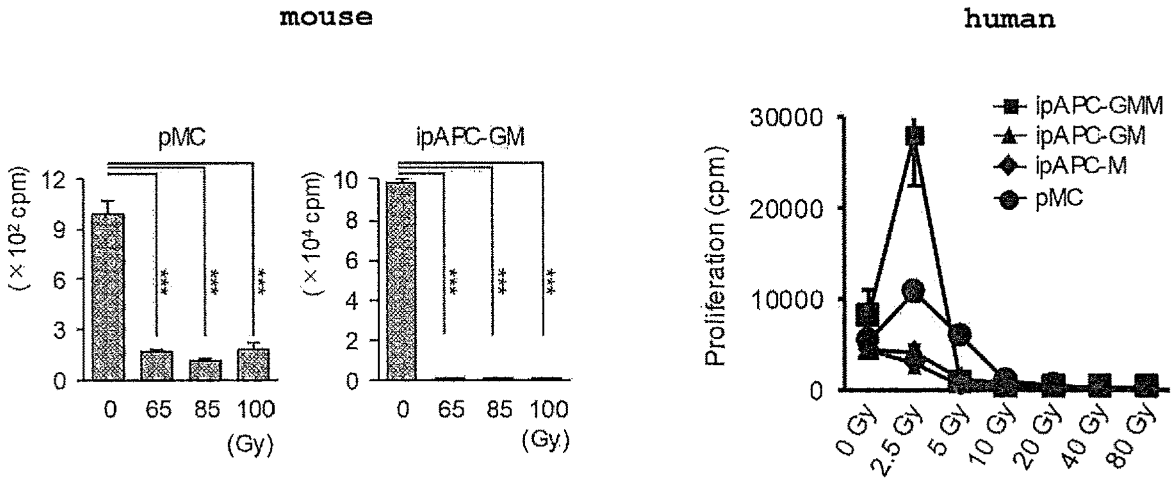

[Fig. 23]
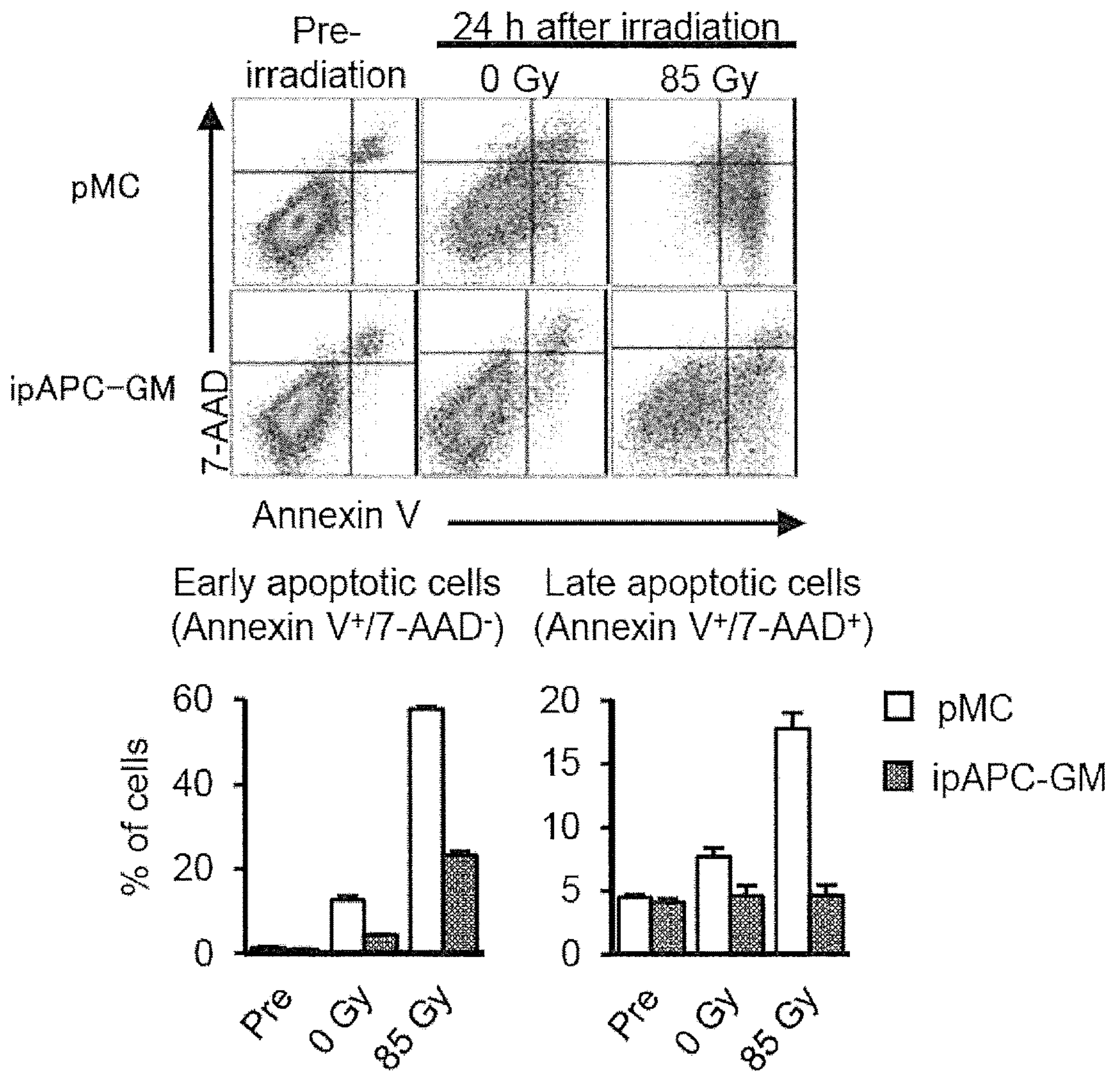
[Fig. 24]
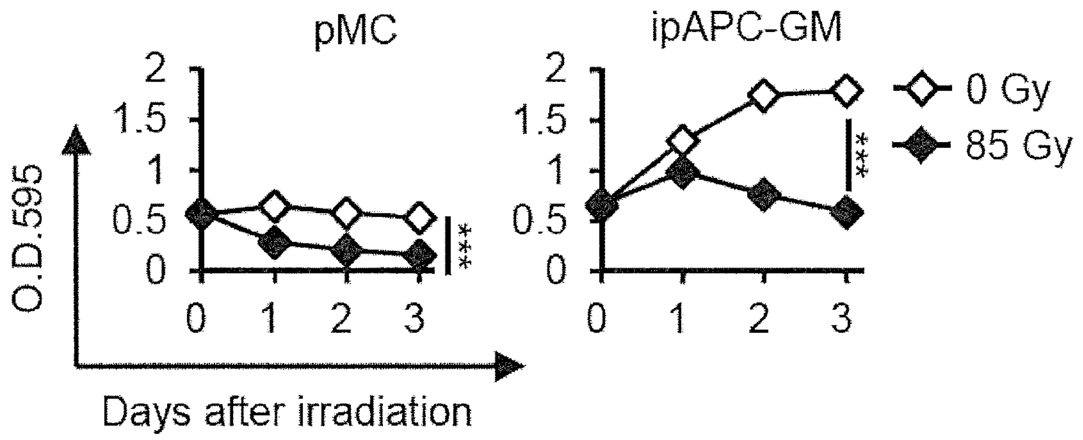

[Fig. 25]
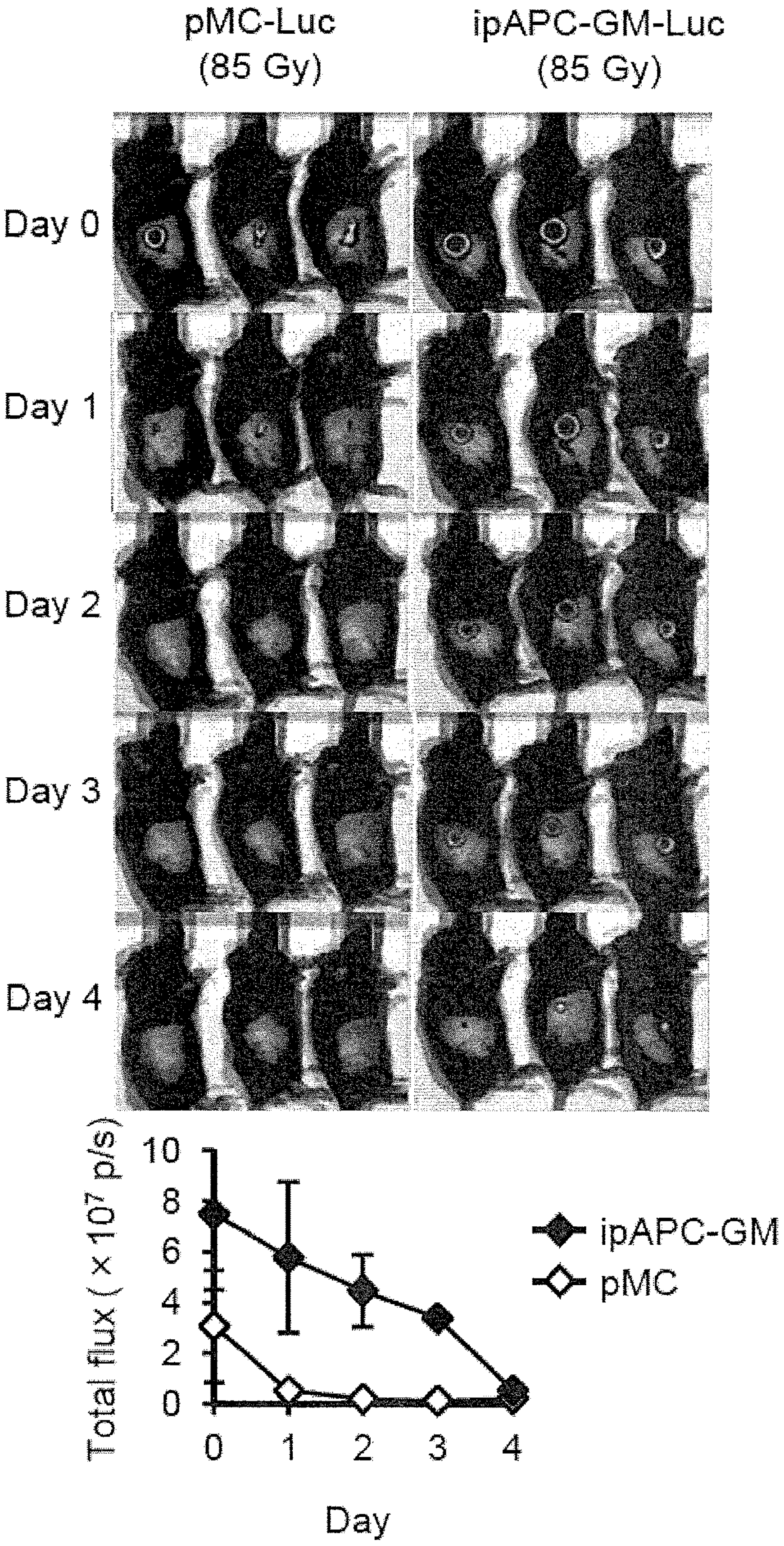

[Fig. 26]
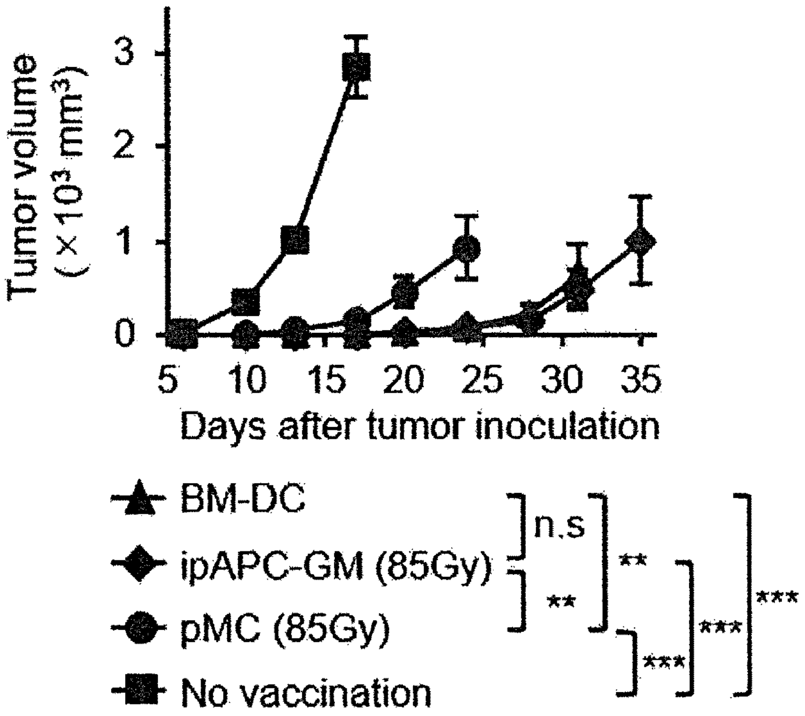
[Fig. 27]
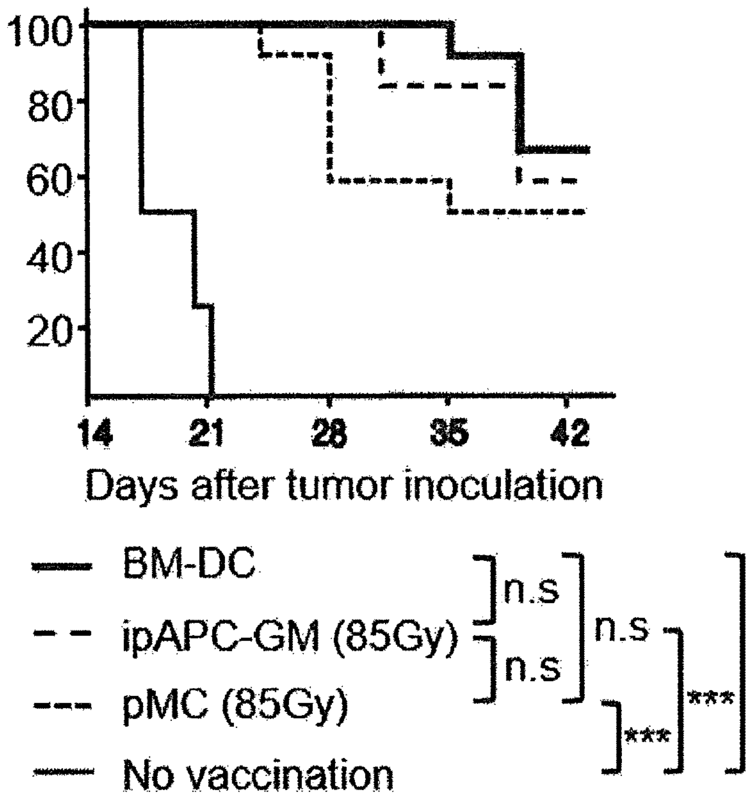

[Fig. 28]
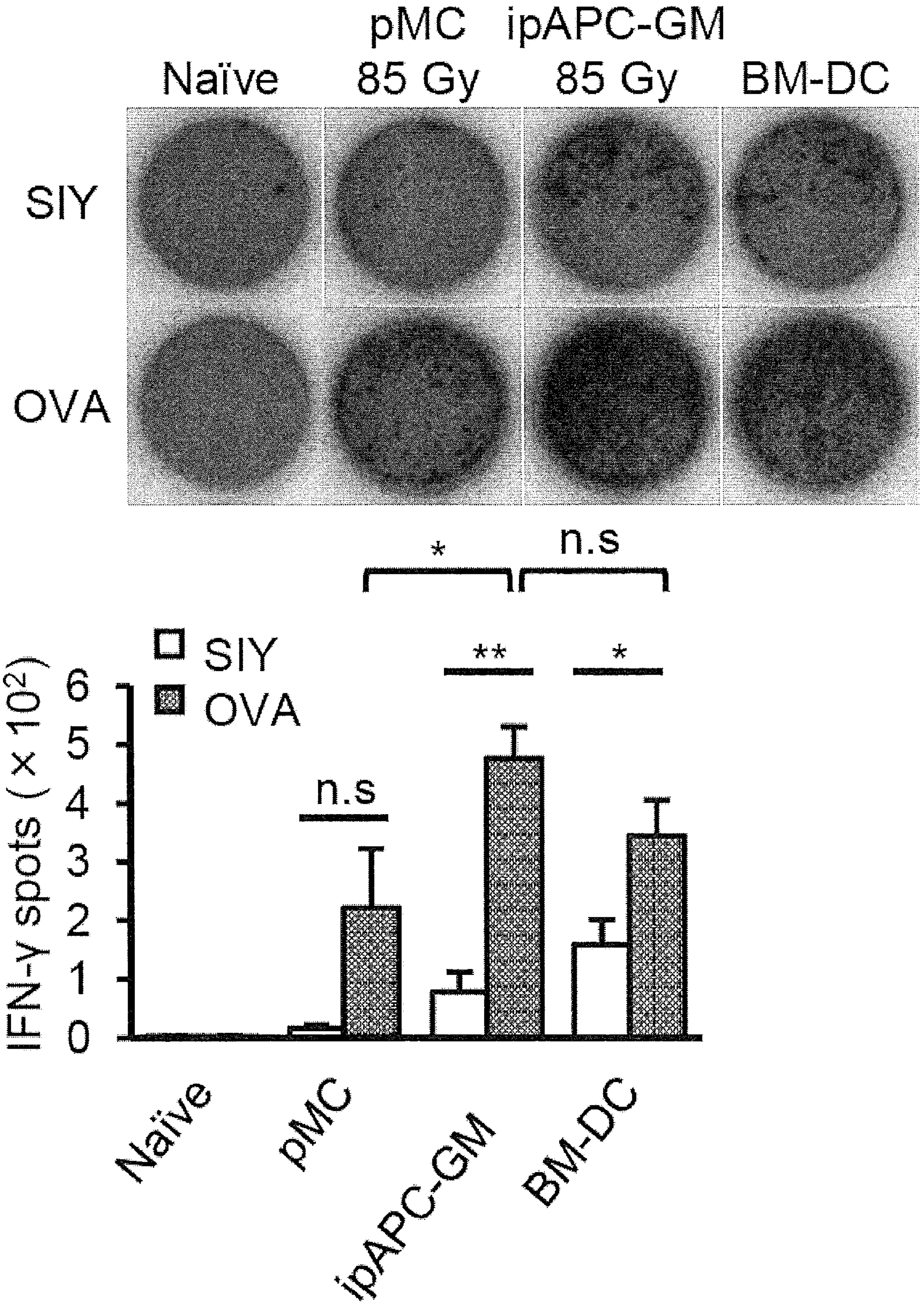

[Fig. 29]
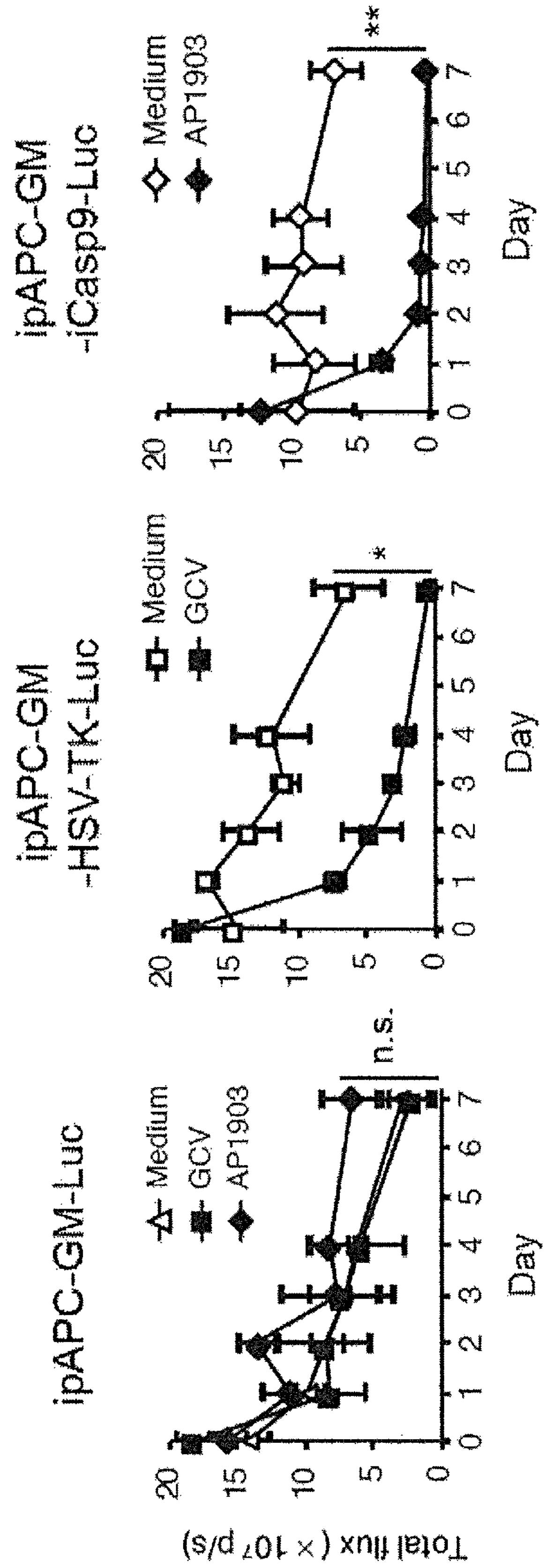

[Fig. 30]
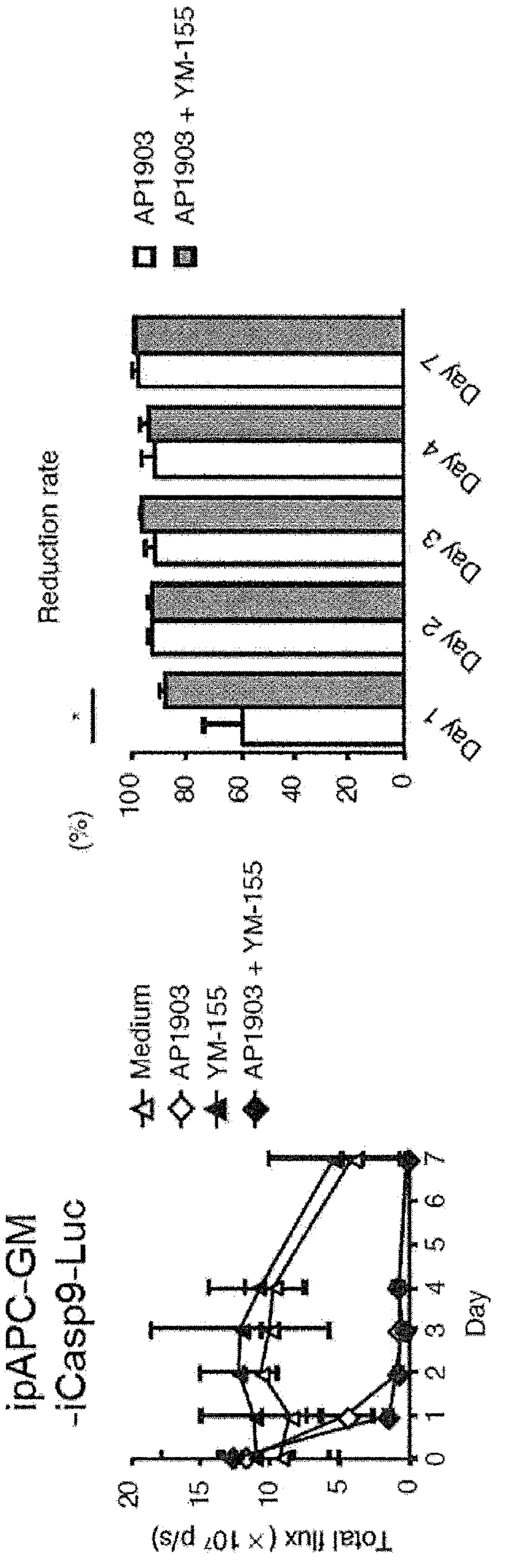

[Fig. 31]
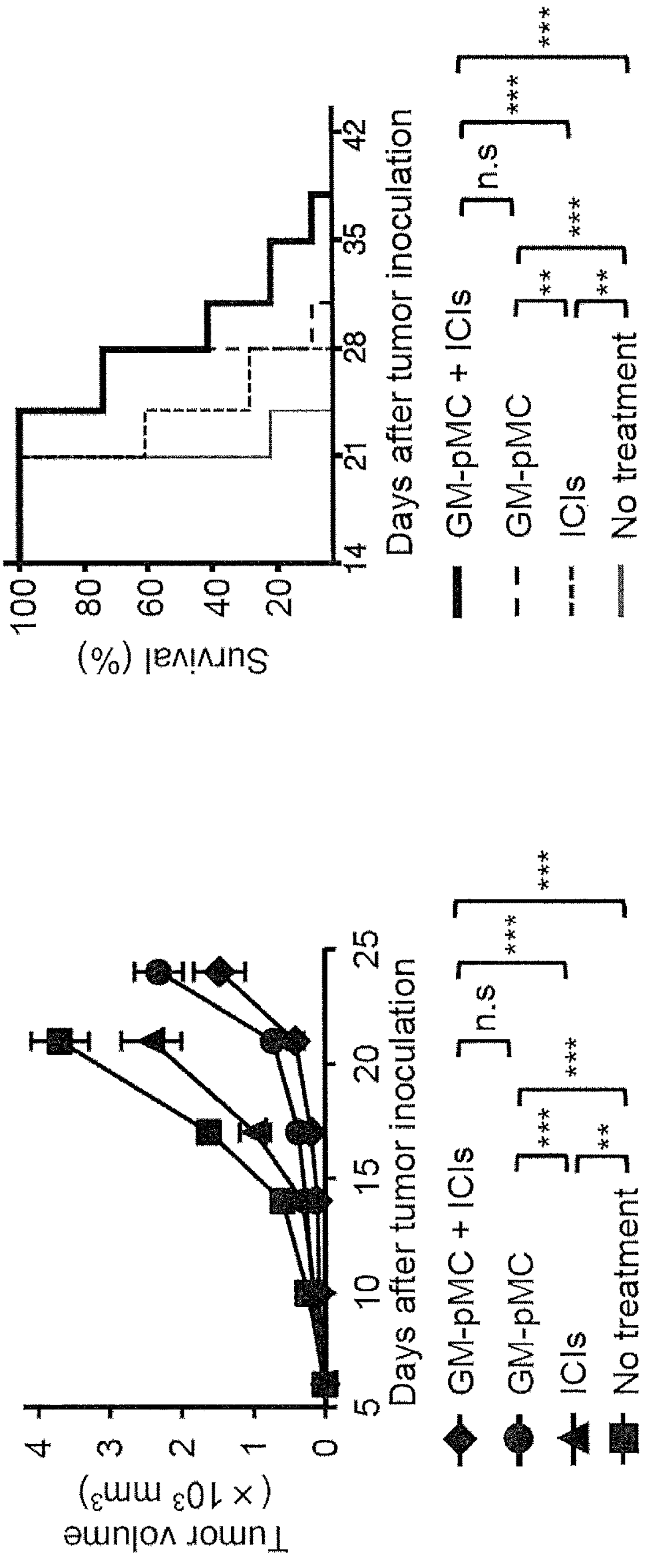

[Fig. 32]
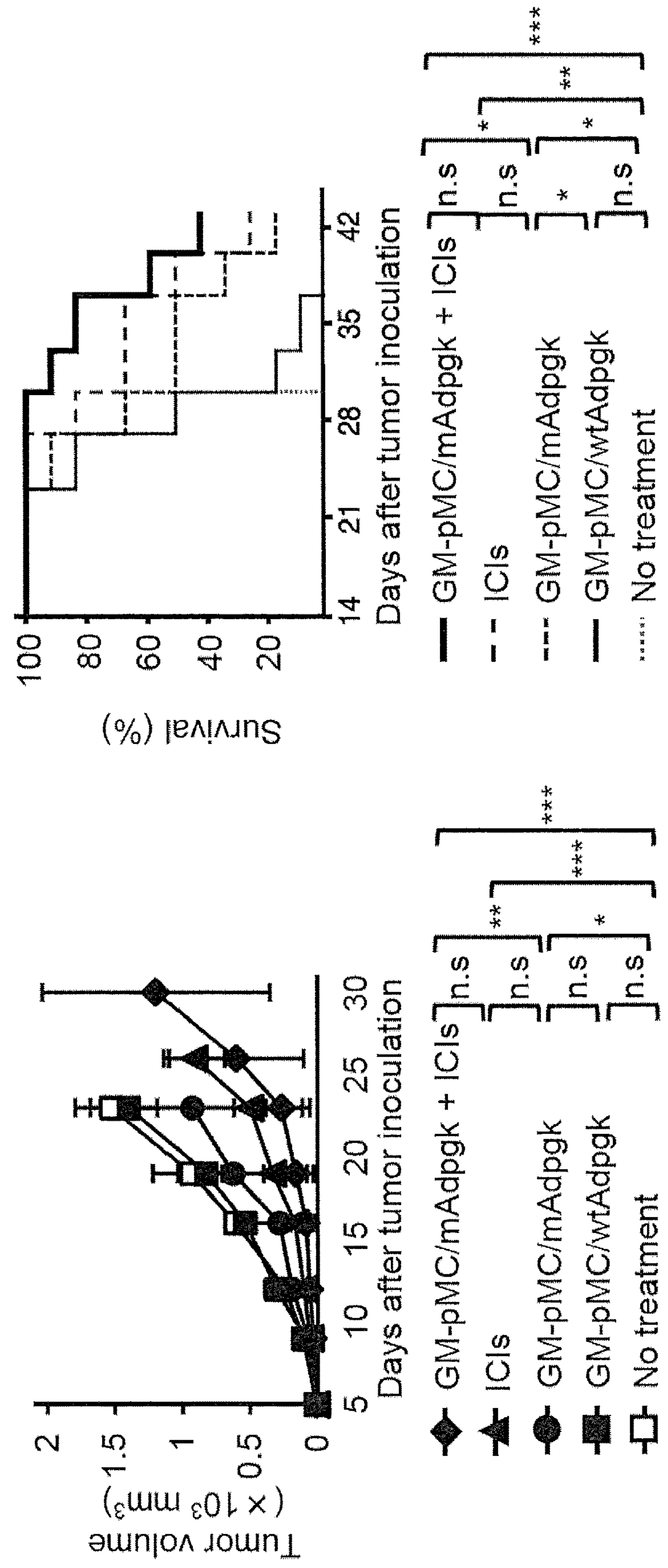

[Fig. 33]
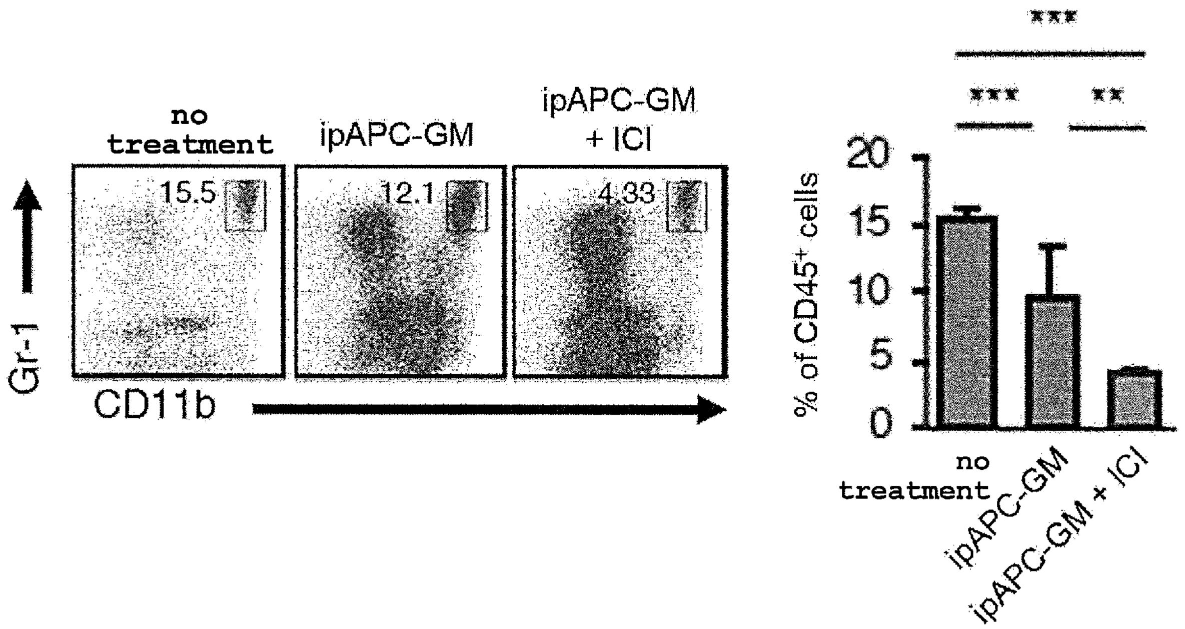
[Fig. 34]
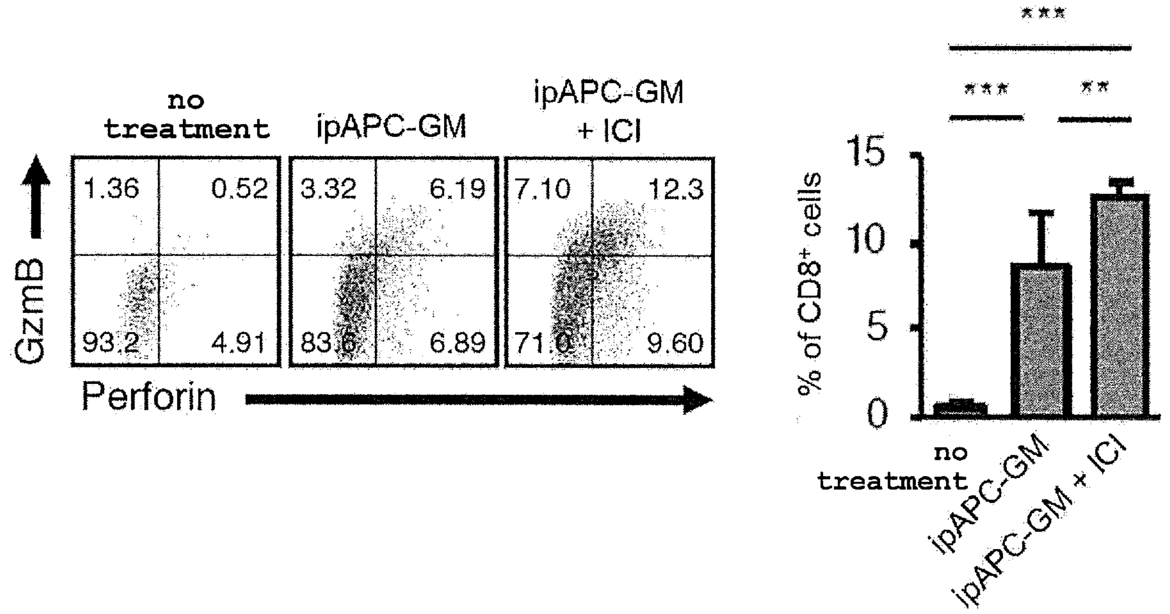

[Fig. 35]
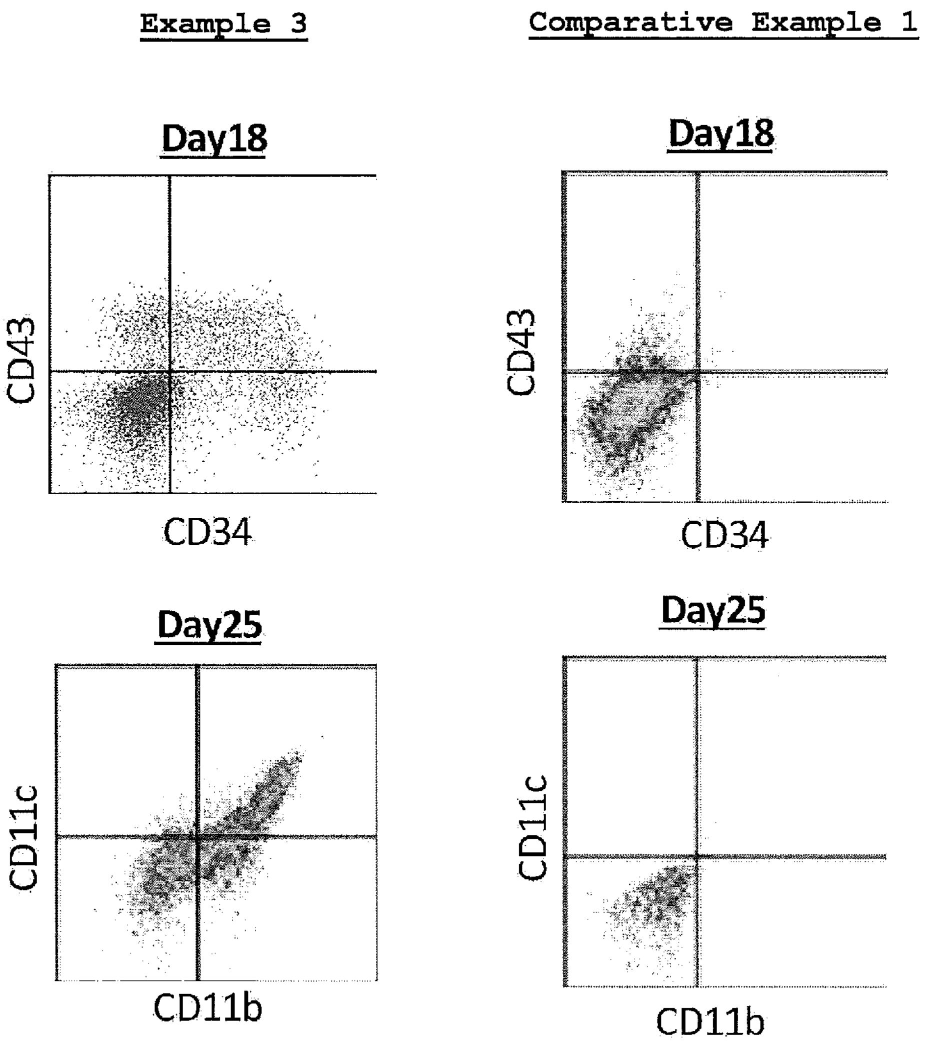
| days of culture | differentiation marker | Example 3 | Comparative Example 1 |
|---|---|---|---|
| Day18 | CD34 | 19.4% | N.D. |
| Day25 | CD11b | 48.3% | N.D. |

METHOD FOR PRODUCING HUMAN PROFESSIONAL ANTIGEN-PRESENTING CELLS

CROSS REFERENCE TO RELATED APPLICATIONS

This application is a continuation of PCT/JP2021/018121, filed on May 12, 2021, and claims priority to Japanese Patent Application No. 2020-084821, filed on May 13, 2020, and Japanese Patent Application No. 2020-149486, filed on Sep. 4, 2020. The entire contents of each are incorporated herein by reference.

TECHNICAL FIELD

The present invention relates to methods for producing human professional antigen-presenting cells derived from pluripotent stem cells, pluripotent stem cell-derived human professional antigen-presenting cells produced by the method, methods for inducing proliferation of T cells by using the human professional antigen-presenting cells, and the like.

BACKGROUND ART

Professional antigen-presenting cells are cells that present fragments of invading bacteria, virus-infected cells, cancer cells, and the like as antigens on the cell surface of their own to activate T cells. Professional antigen-presenting cells are cells that are specialized in antigen presentation and express not only human leukocyte antigen (HLA) class I molecules possessed by normal nucleated cells, but also HLA class II molecules, and include macrophage, dendritic cell, B cell, and the like. Dendritic cells (hereinafter also referred to as DC) are antigen-presenting cells that have potent T cell stimulation activity and play a role in eliciting immune responses to exogenous antigens. The so-called DC vaccine therapy, in which DC is loaded with “cancer antigens” and administered to the body to activate cancer-reactive T cells in the body, is considered to be one of the “cancer immunotherapies” expected to have superior effects (Non Patent Literatures 1 and 2).

Current DC therapy includes many problems in that (1) it requires apheresis in patients to procure DC progenitor cells, (2) DC induction efficiency varies among patients, and it is difficult to obtain DC function and number of cells sufficient for treatment, (3) the cost of personalized medicine using autologous cells is high, and the like.

In order to obtain a clinical effect using DC as a cell preparation, a large amount of cells of about $10^8$ to $10^9$ cells, which cannot be obtained from collected blood, is required. The number of DC present in biological tissues is limited and expansion of DC by in vitro culture is difficult. Thus, it is difficult to collect and prepare a large amount of DC from biological tissues.

Techniques for inducing differentiation of DC from embryonic stem cells (ESC) or induced pluripotent stem cells (iPSC) (Non Patent Literatures 3 to 7) make it possible to prepare DC from pluripotent stem cells to be infinite cell sources. However, the process of differentiating ESC and iPSC into DC via hematopoietic differentiation is complicated, requires time and cost for more than one month of preparation, and a DC vaccine method using same has not been put to practical use. A human iPSC-derived myeloid blood cell line (iPS-ML), which has been reported as a prior art, is produced by two main steps of differentiation induction and gene transfer (Patent Literature 1). The production methods of iPS-ML reported so far show low induction efficiency and low reproducibility, and cannot achieve stable supply of iPS-ML as cell preparations. Problems in practical use are that iPS-ML cannot exhibit functions equivalent to those of DC, and requires a certain way of differentiation induction, such as culture in the presence of cytokine, and the like, in order to exhibit the functions as DC.

There are also reports on the production of human myeloid blood cells that have the ability to proliferate in vitro (Patent Literature 1) and a production method of human myeloid blood cells with suppressed tumorigenicity (Patent Literature 2). However, none of these prior art documents discloses or suggests a production method of human myeloid cells having antigen-presenting ability, or the existence or properties of cells having antigen-presenting ability.

CITATION LIST

Patent Literature

[PTL 1]
JP-B-5861191
[PTL 2]
JP-A-2018-171005

Non Patent Literature

[NPL 1]
Immunity 39: 38-48, 2013.
[NPL 2]
Nat Rev Cancer 17, 209-222, 2017.
[NPL 3]
Blood 101: 3501-8, 2003.
[NPL 4]
J Immunol 172: 776-86, 2004.
[NPL 5]
J Immunol 174: 1888-97, 2005.
[NPL 6]
J Immunol 178: 918-25, 2007.
[NPL 7]
Stem Cells 25: 2720-29, 2007.

SUMMARY OF INVENTION

Technical Problem

A problem of the present invention is to provide a production method of pluripotent stem cell-derived human professional antigen-presenting cells having the ability to proliferate in vitro to enable stable supply as a cell preparation and antigen-presenting ability comparable to that of DC of biological origin, and human professional antigen-presenting cells produced by the method. A further problem of the present invention is to provide a method for promoting proliferation of antigen specific or non-specific T cells by using the human professional antigen-presenting cell of the present invention, and T cells promoted to proliferate and/or produced by the method. A still further problem of the present invention is to provide a pharmaceutical composition for promoting proliferation of T cells containing the professional antigen-presenting cells derived from pluripotent stem cells of the present invention, and an anticancer agent containing antigen specific or non-specific T cells promoted to proliferate and/or produced using the human professional antigen-presenting cells of the present invention.

Solution to Problem

The present invention provides a production method of professional antigen-presenting cells derived from pluripotent stem cells, and the like.

That is, the present invention provides a method for producing a professional antigen-presenting cell, comprising inducing expression of c-MYC, BMI1, and MDM2 in myeloid cells (MC) to obtain proliferative myeloid cells (pMC), and inducing expression of GM-CSF and/or M-CSF in the aforementioned pMC to obtain a professional antigen-presenting cell (pAPC).

In the production method of professional antigen-so presenting cells of the present invention (hereinafter to be referred to as "the production method of the present invention"), the aforementioned myeloid cell may be a myeloid cell differentiated from a pluripotent stem cell.

In the production method of the present invention, the aforementioned pluripotent stem cell may be an induced pluripotent stem cell or an embryonic stem cell.

In the production method of the present invention, the aforementioned c-MYC, BMI1, and MDM2 may be provided by transfection into myeloid cells.

In the production method of the present invention, the aforementioned GM-CSF and/or M-CSF may be provided by transfection into pMC.

When the aforementioned myeloid cell is a myeloid cell (MC) differentiated from a pluripotent stem cell, the production method of the present invention may include differentiating myeloid cells (MC) from pluripotent stem cells by (i) a step of performing a double-layer culture of embryoid body (EB) induced from the aforementioned pluripotent stem cells on feeder cells in a medium containing VEGF, and further culturing same in a medium containing VEGF, SCF, and TPO, or (ii) a step of performing a monolayer culture of embryoid body (EB) induced from the aforementioned pluripotent stem cells in a medium containing BMP-4, VEGF, and SCF without feeder cells, and further culturing same in a medium containing VEGF, TPO, and GM-CSF.

When the aforementioned embryoid body (EB) is formed from pluripotent stem cells, moreover, the production method of the present invention may be a production method for forming an embryoid body (EB) from pluripotent stem cells, including a step of (i) seeding pluripotent stem cells in a container for cell mass-forming culture to form an embryoid body (EB), wherein (ii) the aforementioned container has fine spheroid wells at the bottom, and does not have a flat surface between adjacent wells.

The production method of the present invention may be a production method including (i) seeding pluripotent stem cells in a container for cell mass-forming culture that has fine spheroid wells at the bottom, and does not have a flat surface between adjacent spheroid wells to form an embryoid body (EB), (ii) obtaining myeloid cells (MC) from the aforementioned embryoid body (EB) by the following step (ii)-1 or (ii)-2, that is, (ii)-1 performing a double-layer culture of the aforementioned embryoid body on feeder cells in a medium containing VEGF, and further culturing same in a medium containing VEGF, SCF, and TPO, or (ii)-2 performing a monolayer culture of the aforementioned embryoid body in a medium containing BMP-4, VEGF, and SCF without feeder cells, and further culturing same in a medium containing VEGF, TPO, and GM-CSF, (iii) inducing expression of c-MYC, BMI1, and MDM2 in the myeloid cells (MC) obtained in (ii) to obtain proliferative myeloid cells (pMC), and (iv) inducing expression of GM-CSF and/or M-CSF in the proliferative myeloid cells (pMC) obtained in (iii) to obtain professional antigen-presenting cells (pAPC).

In the production method of the present invention including the aforementioned (i) to (iv), c-MYC, BMI1, and MDM2 may be provided by transfection into myeloid cells (MC), and GM-CSF and/or M-CSF may be provided by transfection into proliferative myeloid cells (pMC).

In the production method of the present invention including forming an embryoid body (EB) from pluripotent stem cells, the size of the aforementioned embryoid body (EB) may be 50 to 200 μm.

The production method of the present invention may further include exposure of the aforementioned professional antigen-presenting cells (pAPC) to radiation.

The present invention provides a professional antigen-presenting cell (pAPC) produced by any of the production methods of the present invention.

The professional antigen-presenting cell (pAPC) of the present invention may also be a professional antigen-presenting cell (pAPC) that disappears from a living body, when administered to the living body after radiation irradiation, in at least 3 or 4 days after the administration to the living body.

The professional antigen-presenting cell (pAPC) of the present invention may be a professional antigen-presenting cell (pAPC) that shows low expression of CD11b/c and expression of CD74.

The present invention provides professional antigen-presenting cells that are derived from pluripotent stem cells (pAPC) and show low expression of CD11b/c and expression of CD74.

A professional antigen-presenting cell (pAPC) produced by any of the production methods of the present invention, or the pluripotent stem cell-derived professional antigen-presenting cell (pAPC) of the present invention may further express CD33.

In the pluripotent stem cell-derived professional antigen-presenting cells (pAPC) of the present invention, the aforementioned pluripotent stem cells may be embryonic stem cells or induced pluripotent stem cells.

The pluripotent stem cell-derived professional antigen-presenting cells (pAPC) of the present invention may express exogenous GM-CSF and/or M-CSF.

In the pluripotent stem cell-derived professional antigen-presenting cells (pAPC) of the present invention that express exogenous GM-CSF and/or M-CSF, the aforementioned GM-CSF and/or M-CSF may be provided by transfection.

A professional antigen-presenting cell (pAPC) produced by the production method of the present invention, or the pluripotent stem cell-derived professional antigen-presenting cells (pAPC) of the present invention showing low expression of CD11b/c and expression of CD74 have self-proliferation potency and may show apoptosis resistance.

The present invention provides a pharmaceutical composition for inducing and/or promoting proliferation of T cells that express CD8, the composition containing any of the professional antigen-presenting cells of the present invention.

The present invention provides a method for promoting proliferation of T cells that express antigen non-specific or antigen specific CD8 in vivo and in vitro by coculturing any of the professional antigen-presenting cells of the present invention or GM-CSF, and naive T cells expressing CD8 in vitro.

In the method of the present invention for promoting so proliferation of T cells that express CD8, the aforementioned professional antigen-presenting cell may be a professional antigen-presenting cell loaded with a desired antigen.

The method of the present invention for promoting proliferation of T cells that express CD8 may further include exposing the aforementioned professional antigen-presenting cells loaded with an antigen to radiation in vitro.

In the method of the present invention for promoting proliferation of T cells that express CD8, when the aforementioned professional antigen-presenting cells exposed to radiation are administered to a living body after the in vitro radiation irradiation, they may disappear from the living body in at least 3 to 4 days.

In the method of the present invention for promoting proliferation of T cells that express CD8, the T cells that express CD8 may be T cells that express CD8 specific to an antigen loaded with professional antigen-presenting cells.

The present invention provides T cells that express CD8 and promoted to proliferate by the method of the present invention for promoting proliferation of T cells that express CD8.

The present invention provides a method for producing T cells that express antigen non-specific or specific CD8, by using the method of the present invention for promoting proliferation of T cells that express CD8.

The present invention provides T cells that express antigen non-specific or specific CD8 produced by the method of the present invention for producing T cells that express antigen non-specific or specific CD8.

The present invention provides a method for producing T cells that express antigen specific CD8 for administration to a body. The method of the present invention for producing T cells that express antigen specific CD8 for administration to a body includes loading the professional antigen-presenting cell (pAPC) of the present invention with an antigen, exposing the aforementioned professional antigen-presenting cell loaded with the antigen to radiation, and coculturing in vitro the aforementioned professional antigen-presenting cell exposed to radiation, and naive T cells that express CD8 to promote proliferation of T cells that express antigen specific CD8. The professional antigen-presenting cell (pAPC) may have self-proliferation potency, as well as apoptosis resistance.

The present invention provides T cells that express antigen specific CD8 for administration to a body that are produced by the method of the present invention for producing T cells that express antigen specific CD8 for administration to a body.

In the T cells that express antigen specific CD8 for administration to a body that are produced by the method of the present invention for producing T cells that express antigen specific CD8 for administration to a body, when administered to a living body after radiation irradiation, the aforementioned pluripotent stem cell-derived professional antigen-presenting cells exposed to radiation may disappear in at least 3 to 4 days after administration to the living body.

The present invention provides an anticancer agent. The anticancer agent of the present invention comprises T cells expressing CD8 that are promoted to proliferate by the method of the present invention for promoting proliferation of T cells expressing CD8, or T cells that express antigen specific CD8 for administration to a body, produced by the production method of the present invention of T cells that express antigen specific CD8 for administration to a body, wherein the antigen in the method of the present invention for promoting proliferation of T cells expressing CD8 and the production method of the present invention of T cells that express antigen specific CD8 for administration to a body is a cancer specific antigen.

Advantageous Effects of Invention

The professional antigen-presenting cells derived from pluripotent stem cells and provided by the present invention are cells that have acquired self-proliferation potency. The professional antigen-presenting cells derived from pluripotent stem cells of the present invention once constructed do not require induction of redifferentiation or reproduction from pluripotent stem cells into myeloid cells, and have a superior antigen-presenting ability equivalent to that of DC, which has not been reported so far.

BRIEF DESCRIPTION OF DRAWINGS

FIG. 1

Polygonal line graphs showing the measurement results of MTT assay examining the effect of a medium containing GM-CSF and/or M-CSF (20% FBS-containing αMEM) on the growth rate of iPSC-derived proliferative myeloid cell (pMC) cultured with or without feeder cells. The vertical axis shows the concentration of formazan metabolized from an MTT reagent (evaluated as absorbance at wavelength 595 nm), and the horizontal axis shows culture days.

FIG. 2

Histograms showing the results of CD11b and CD11c and CD33 surface antigen analysis of iPSC-derived pMC cultured with or without feeder cells by a flow cytometer.

FIG. 3

Histograms showing the results of GM-CSF-Venus surface antigen analysis of mouse pMC and ipAPC-GM by a flow cytometer (upper left), M-CSF-dCD19 surface antigen analysis of human pMC and ipAPC-M (lower left), GM-CSF-dCD19 surface antigen analysis of human pMC and ipAPC-GM (upper right), and GM-CSF-M-CSF-CD19 surface antigen analysis of human pMC and ipAPC-GMM (lower right).

FIG. 4

Bar graphs showing the quantification results by ELISA of GM-CSF production in the culture supernatant of mouse pMC and ipAPC-GM (left), and M-CSF production (middle), and GM-CSF production (right) in the culture supernatant of human pMC, ipAPC-M, ipAPC-GM, and ipAPC-GMM.

FIG. 5

Polygonal line graphs showing the measurement results of MTT assay examining the effect of a medium containing GM-CSF and/or M-CSF (20% FBS-containing αMEM) on the growth rate of mouse ipAPC-GM (upper) and human (lower) ipAPC-GMM. The measurement results are the mean values for repeated trial number n=3, and the error bars indicate the standard deviation.

FIG. 6

Histograms showing the results by a flow cytometer for HLA-ABC, HLA-DR, CD40, CD80, CD83, CD86, CCR7, CD74, CD11b, CD11c and CD33 surface antigen analysis in human ipAPC-GM, ipAPC-M, and ipAPC-GMM.

FIG. 7

Histograms showing the analysis results with a flow cytometer of HLA-ABC, HLA-DR, CD40, CD80, CD83, CD86, CCR7, CD74, CD11b, CD11c and CD33 surface antigens in DC.

FIG. 7

Histograms showing the results by a flow cytometer for HLA-ABC, HLA-DR, CD40, CD80, CD83, CD86, CCR7, CD74, CD11b, CD11c and CD33 surface antigen analysis in DC.

FIG. 8

Plots (C57BL/6 (left) and 129/Sv (right)) of profiles of mouse pMC, mouse ipAPC-GM, and GM-CSF-added mouse pMC, with respect to two axes (PC1 and PCA) with high contribution ratio obtained by principal component analysis (PCA) multivariate analysis after whole transcriptome analysis (RNA-seq analysis) of GM-CSF-added mouse pMC.

FIG. 9

Diagrams showing the results of gene set enrichment analysis (GSEA) of mouse ipAPC-GM for mouse pMC and GM-CSF-added mouse pMC.

FIG. 10A

Cytograms showing the results of Annexin V and 7-AAD analysis by a flow cytometer for mouse ipAPC-GM (lower panel) and mouse pMC (upper panel) on the date of culture start (Day 0, left) and the fourth day of culture (Day 4, right) in 20% FBS-containing αMEM without exogenous cytokines. The vertical axis of FIG. 10A shows fluorescence intensity of 7-AAD and the horizontal axis shows fluorescence intensity of Annexin V.

FIG. 10B

The polygonal line graphs (lower left, lower right, and upper right) of FIG. 10B show, similar to FIG. 10A, the analysis results by a flow cytometer for the percentage of cells in the total cells, that are obtained by sampling Annexin V-negative and 7-AAD-negative fractions, Annexin V-positive and 7-AAD-negative fractions, and Annexin V-positive and 7-AAD-positive fractions respectively as viable cells (lower left), early apoptotic cells (lower right), and late apoptotic cells (upper right) every day from the start of culture to day 4 of culture, and gating by each fraction. The vertical axis of the polygonal line graphs of FIG. 10B lower left, lower right, and upper right shows the percentage of cells gated by each fraction in the total cells, and analyzed by flow cytometry on each sampling date of mouse ipAPC-GM or mouse pMC, and the horizontal axis shows the sampling date from the culture start date to the culture day 4.

FIG. 10C

Similar cytograms (Day0 and Day3) of human ipAPC-GMM (first row), ipAPC-M (second row), ipAPC-GM (third row), and pMC (fourth row).

FIG. 10D

Polygonal line graphs of the analysis results of the percentage of viable cells (lower left), early apoptotic cells (lower right), and late apoptotic cells (upper right).

FIG. 11

Plot (left) of quantification results of allogeneic mixed lymphocyte reaction (alloMLR) by scintillation counting of $[^3H]$-thymidine uptake after coculture of C57BL/6 strain mouse ipAPC-GM or pMC with antigen unstimulated T cells prepared from BALB/c strain mouse at various mixing ratios. Plot (right) of quantification results of alloMLR after coculturing human ipAPC-GMM, ipAPC-GM, ipAPC-M, or pMC in the same manner as with alloreactive T cells. The vertical axis shows the results of scintillation counting of $[^3H]$-thymidine uptake (unit: cpm), and the horizontal axis shows the ratio of the number of ipAPC-GMM, ipAPC-GM, ipAPC-M, or pMC cells:number of T cells free of antigen stimulation.

FIG. 12A

Cytogram (left) of flow cytometric evaluation of human pMCs, ipAPC-GM, ip-APC-M, ip-APC-GM, or DCs loaded with DQ-OVA protein and bar graph (right) showing the percentage of cells that incorporated and intracellularly digested DQ-OVA.

FIG. 12B

Mouse ipAPC-GM was loaded with OVA peptide $OVA_{257-264}$ or OVA protein in a concentration-dependent manner, and proliferation of ipAPC-GM was stopped by radiation irradiation. Then, they were cocultured with naive CD8-positive T cells OT-1 having OVA-specific T cell receptor (TCR). The in vitro proliferation of antigen-specific CD8-positive T cells was quantified by scintillation counting of $[^3H]$-thymidine uptake. Plots of the results are shown. The vertical axis shows the results of scintillation counting of $[^3H]$-thymidine uptake (unit: $10^4$ cpm), and the horizontal axis shows the concentration of OVA peptide $OVA_{257-264}$ or OVA protein.

FIG. 13

Bar graphs showing comparison of the OT-1 proliferation-inducing activity between mouse ipAPC-GM and mouse pMC under conditions loaded with 10 NM OVA peptide (left) or 100 μg/mL OVA protein (right). The vertical axis shows the results of scintillation counting of $[^3H]$-thymidine uptake (unit: $10^4$ cpm (left), $10^3$ cpm (right)) and the horizontal axis shows cells cocultured with OT-1. Asterisk (*) indicates $p<0.05$ by two-tailed Student's t test.

FIG. 14

A polygonal line graph showing comparison of suppressive effect on subcutaneously transplanted tumor of OVA-expressing cancer cells using mouse ipAPC-GM and mouse pMC loaded with OVA peptide, and mouse ipAPC-GM and mouse pMC not loaded with peptide. The vertical axis shows transplanted tumor volume (unit: cm), and the horizontal axis shows the number of days after tumor transplantation. Asterisk (*) shows p-values by One-way ANOVAs with Tukey's test: $*p<0.05$, $p<0.01$, $*p<0.001$. The animal not administered with mouse ipAPC-GM or mouse pMC showed the weakest suppressive effect, mouse ipAPC-GM and mouse pMC not loaded with peptide showed an almost equivalent suppressive effect, mouse ipAPC-GM loaded with OVA peptide showed the highest suppressive effect, and mouse pMC loaded with OVA peptide the next highest suppressive effect.

FIG. 15

Survival curves of individual tumor-bearing mice treated with each cell of FIG. 15. Asterisk (*) shows p-values by log-rank tests: $*p<0.05$, $p<0.01$, $*p<0.001$.

FIG. 16

A photograph of stained culture dishes showing the results of an ELISPOT assay that examined the frequency of OVA peptide antigen-specific T cells among peripheral blood mononuclear cells collected from mice on day 56 of tumor implantation, and a bar graph summarizing the results. Upper composite pictures show the frequency of antigen-specific T cells that produce interferon-γ by ELISPOT assay of mouse ipAPC-GM (right) stimulated with OVA peptide (lower) or control STY peptide (upper), and naive T cells (left). The lower bar graph quantitatively shows the results of the upper composite pictures, showing the frequency of antigen-specific T cells that produce interferon-γ and induced by mouse ipAPC-GM or naive T cells stimulated with OVA peptide (gray) or control SIY peptide (white). The vertical axis of the graph shows the number of spots reactive with interferon γ (unit: $1\times10^2$ cells).

FIG. 17

A bar graph showing proliferation of naive OT-1 CD8-positive T cells in a medium containing the culture supernatant of ipAPC-GM or pMC. The vertical axis shows the results of scintillation counting of [$^3$H]-thymidine uptake into T cells (unit: $10^3$ cpm). Asterisk (**) indicates $p<0.01$ by two-tailed Student's t test.

FIG. 18

A bar graph showing the effect of addition of anti-GM-CSF neutralizing antibody (αGM-CSF Ab) or control antibody (Control Ab) to a medium containing the culture supernatant of ipAPC-GM on the proliferation of naive OT-1 CD8-positive T cells. The vertical axis shows the results of scintillation counting of [$^3$H]-thymidine uptake into T cells (unit: $10^3$ cpm).

FIG. 19

A bar graph showing the effect of coculture with ipAPC-GM or pMC on the proliferative activity of T cells. The vertical axis shows the results of scintillation counting of [$^3$H]-thymidine uptake into T cells (unit: $10^3$ cpm). Asterisk (**) indicates $p<0.01$ by two-tailed Student's t test.

FIG. 20

Histograms showing the flow cytometer analysis results of T cell receptor (TCR) Vβ frequency of naive CD8-positive T cells (left), ipAPC-GM and naive CD8-positive T cells after so coculture (middle), and splenocyte and naive CD8-positive T cells after coculture (right). The horizontal axis shows each repertoire of TCRVβ, and the vertical axis shows use frequency of each repertoire.

FIG. 21

Phase-contrast micrographs comparing the influence of different intensities of radiation irradiation on cell morphology of ipAPC-GM (right) or pMC (left). The absorbed doses of the cells in the top to bottom rows are 0 Gy, 65 Gy, 85 Gy, and 100 Gy, respectively, and the magnification of the photographs is ×400. Scale bar indicates 50 μm.

FIG. 22

Bar graphs showing comparison of the influence of different intensities of radiation irradiation on cell proliferation of mouse ipAPC-GM (middle) or mouse pMC (left), human ipAPC-GMM, ipAPC-GM, ipAPC-M, and pMC (right). The horizontal axis shows absorbed dose (unit: Gy) of irradiated radiation, and the vertical axis shows the results of scintillation counting of [$^3$H]-thymidine uptake of ipAPC-GM (right) or pMC (left) after radiation irradiation under respective conditions (unit: $10^2$ cpm (left), $10^4$ cpm (middle), cpm (right)).

FIG. 23

FIG. 23, upper, is a cytogram showing the results of Annexin V and 7-AAD analysis by a flow cytometer of mouse ipAPC-GM (lower panel) and mouse pMC (upper panel) before irradiation, 24 hr after 0 Gy or 85 Gy irradiation. FIG. 23, lower left and lower right, are, similar to the upper cytogram, bar graphs showing the analysis results by flow cytometer of the percentage of cells in the total cells, that are obtained by sampling Annexin V-positive and 7-AAD-negative fractions and Annexin V-positive and 7-AAD-positive fractions respectively as early apoptotic cells (lower left) and late apoptotic cells (lower right) before irradiation, 24 hr after 0 Gy or 85 Gy irradiation, and gating by each fraction. The vertical axis of the upper cytogram of FIG. 23 shows the fluorescence intensity of 7-AAD and the horizontal axis shows the fluorescence intensity of Annexin V. The vertical axis of the bar graphs of FIG. 23 lower left and lower right shows the percentage of cells gated by each fraction in the total cells, and analyzed by flow cytometry on each sampling date of mouse ipAPC-GM or mouse pMC, and the horizontal axis shows samples before irradiation, and 24 hr after 0 Gy or 85 Gy irradiation.

FIG. 24

Polygonal line graphs showing the evaluation results of the cell proliferation in vitro of mouse ipAPC-GM or mouse pMC irradiated with 0 or 85 Gy by MTT assay continuously for 3 days after irradiation. The vertical axis shows the concentration of formazan metabolized from MTT reagent (measurement based on absorbance at wavelength 595 nm) and the horizontal axis shows the number of days of culture.

FIG. 25

Photographed images (upper) of in vivo imaging of all individual mice obtained by subcutaneously administering luciferase-expressing ipAPC-GM (ipAPC-GM-Luc) or pMC (pMC-Luc) irradiated with 85 Gy to mice of the same strain, and measuring viable cells by biochemiluminescence every day (upper) from the administration day (Day 0) to the fourth day (Day 4), and a polygonal line graph (lower) showing time-course changes in the total flux of luciferase luminescence. The right side of the photographed images above is a scale showing the luciferase luminescence intensity in chromatic colors, and the minimum luminescence intensity is 5.46×e5, and the maximum luminescence intensity is 4.31×e6 (unit: p/sec/cm$^2$/sr). The vertical axis of the lower polygonal line graph shows the total flux of luciferase luminescence (unit: $10^7$p/s), and the horizontal axis shows the number of days after administration.

FIG. 26

After loading ipAPC-GM whose proliferation ability was stopped by radiation irradiation with OVA peptide and intraperitoneal administration, cancer cells MO4 were implanted subcutaneously. A polygonal line graph showing changes in tumor volume as the result of the evaluation of tumor diameter every 3 to 4 days. The vertical axis shows tumor volume (unit: $10^3$ m$^3$) and the horizontal axis shows the number of days after tumor inoculation. When no antigen-presenting cells were administered, the tumor suppressive effect was the weakest, the group administered with pMC after 85 Gy irradiation showed the second weakest tumor suppressive effect, and ipAPC-GM after irradiation with 85 Gy showed the highest tumor suppressive effect as did non-irradiated bone marrow-derived dendritic cells (BM-DC).

FIG. 27

Survival curves of individual tumor-bearing mice treated with each cell of FIG. 26.

FIG. 28

A photograph of stained culture dishes showing the results of an ELISPOT assay that examined the frequency of OVA peptide antigen-specific T cells among peripheral blood mononuclear cells collected from mice on day 56 of tumor implantation, and a bar graph summarizing the results. Upper composite pictures show the frequency of antigen-specific T cells that produce interferon-γ by ELISPOT assay of mouse ipAPC-GM irradiated with 85 Gy after loading with OVA peptide (lower) or control SIY peptide (upper) (ipAPC-GM 85 Gy), mouse pMC also irradiated with 85 Gy after loading with OVA peptide (lower) or control STY peptide (upper) (pMC 85 Gy), bone marrow dendritic cells (BM-DC, right end) also loaded with OVA peptide (lower) or control STY peptide (upper), and naive T cells (left end). The lower bar graph quantitatively shows the results of the upper composite pictures, showing the frequency of antigen-specific T cells that produce interferon-γ and induced by irradiated mouse ipAPC-GM and pMC loaded with OVA peptide (gray) or control STY peptide (white), bone marrow dendritic cells loaded with OVA peptide (gray) or control STY peptide (white), and naive T cells. The vertical axis of the graph shows the number of spots reactive with interferon γ (unit: $1\times10^2$ cells).

FIG. 29

Polygonal line graphs showing time-course changes in the total flux of luciferase luminescence resulting from in vivo imaging of all individual mice obtained by subcutaneously administering luciferase-expressing ipAPC-GM introduced with suicide gene HSV-TK or iCasp9 (ipAPC-GM-HSV-TK-Luc or ipAPC-GM-iCasp9-Luc) or luciferase-expressing ipAPC-GM (ipAPC-GM-Luc) to mice of the same strain, and measuring viable cells in the body by biochemiluminescence from the administration day (Day 0) to the seventh day (Day 7). The results of intraperitoneal administration of GCV, AP1903, which are suicide gene inducing reagents, or physiological saline (Medium) without an inducing reagent, for five consecutive days from the day of administration (Day 0) to the fourth day (Day 4) are shown. * indicates $p<0.05$ and ** indicates $p<0.01$ by two-tailed Student's t test.

FIG. 30

A polygonal line graph (left) showing time-course changes in the total flux of luciferase luminescence resulting from in vivo imaging of all individual mice obtained by subcutaneously administering luciferase-expressing ipAPC-GM introduced with suicide gene iCasp9 (ipAPC-GM-iCasp9-Luc) to mice of the same strain, and measuring viable cells in the body by biochemiluminescence from the administration day (Day 0) to the seventh day (Day 7). A bar graph (right) showing signal reduction rate (Reduction rate) on each measurement day with the signal intensity on Day0 as 100%. The results of intraperitoneal administration of iCasp9 inducing reagent AP1903, or Survivin inhibitor YM-155, or physiological saline (Medium) without an inducing reagent, for five consecutive days from the day of administration (Day 0) to the fourth day (Day 4) are shown. * indicates $p<0.05$ by two-tailed Student's t test.

FIG. 31

Immune checkpoint inhibitor (ICI)-low-sensitive cancer cells MO4 were subcutaneous transplanted to mice to form a tumor, and ipAPC-GM loaded with OVA peptide, or ICI (anti-CTLA-4 antibody and anti-PD-L1 antibody), or ipAPC-GM and ICI in combination was intraperitoneally administered to the mice. A polygonal line graph (left) showing changes in tumor volume as the result of the evaluation of tumor diameter every 3 to 4 days, and survival curves (right) of individual tumor-bearing mice. The vertical axis of the polygonal line graph (left) shows tumor volume (unit: $10^3$ $mm^3$) and the horizontal axis shows the number of days after tumor transplantation. The vertical axis of the survival curve (right) shows the survival rate of the mice and the horizontal axis shows the number of 20 days after tumor transplantation. In One-way ANOVAs with Tukey's test, * indicates $p<0.05$,  indicates $p<0.01$, and * indicates $p<0.001$. When no ICI or antigen-presenting cells were administered, the tumor suppressive effect was the weakest, the group administered with ICI showed the second weakest tumor suppressive effect, and ipAPC-GM after 85 Gy irradiation and a combined use of ipAPC-GM and ICI showed the highest tumor suppressive effect.

FIG. 32

ICI-sensitive cancer cells MC38 were subcutaneously transplanted to mice to form a tumor and, as a cancer antigen, ipAPC-GM loaded with mAdpgk or wtAdpgk peptide, or ICI (anti-CTLA-4 antibody and anti-PD-L1 antibody), or ipAPC-GM and ICI in combination was intraperitoneally administered to the mice. A polygonal line graph (left) showing changes in tumor volume as the result of the evaluation of tumor diameter every 3 to 4 days, and survival curves (right) of individual tumor-bearing mice. The vertical axis of the polygonal line graph (left) shows tumor volume (unit: $10^3$ $mm^3$) and the horizontal axis shows the number of days after tumor transplantation. The vertical axis of the survival curve (right) shows the survival rate of the mice and the horizontal axis shows the number of days after tumor transplantation. In One-way ANOVAs with Tukey's test, * indicates $p<0.05$,  indicates $p<0.01$, and * indicates $p<0.001$. When no ICI or antigen-presenting cells were administered, the tumor suppressive effect was the weakest, the group administered with ipAPC-GM loaded with wtAdpgk showed the second weakest tumor suppressive effect. Compared with wtAdpgk peptide-loaded ipAPC-GM, mAdpgk peptide-loaded ipAPC-GM treated group did not show a significant difference but showed a tendency to suppress an increase in the tumor diameter, and significantly prolonged the survival of mice. Compared with ICI alone treatment, no significant difference was found in the time-course changes in the tumor size and survival of mice by mAdpgk peptide-loaded ipAPC-GM. When ICI and mAdpgk peptide-loaded ipAPC-GM were used in combination, no significant difference was found from ICI alone, but an increase in the tumor diameter was significantly suppressed and mouse survival was prolonged more than ipAPC-GM alone treatment.

FIG. 33

Cytograms (left) showing the results of Gr-1 and CD11b surface antigen analysis by flow cytometry of CD45-positive immunocytes in tumor after treatment of tumor-bearing mice transplanted with cancer cell MO4 with ipAPC-GM alone or combined use with immune checkpoint inhibitor (ICI). Gate numbers indicate percentage of bone marrow-derived immunosuppressive cells (MDSC). The right figure is a bar graph showing the ratio of MDSCs calculated from the results of flow cytometry analysis.  indicates $p<0.01$ and * indicates $p<0.001$ by two-tailed Student's t test.

FIG. 34

Cytograms (left) showing the results of GzmB and Perforin surface antigen analysis by flow cytometry of CD8-positive T cells in tumor after treatment of tumor-bearing mice transplanted with cancer cell MO4 with ipAPC-GM alone or combined use with immune checkpoint inhibitor (ICI). Gate numbers indicate percentage with respect to the measured CD8-positive T cells. The right figure is a bar graph showing the ratio of both GzmB and Perforin-positive CD8-positive T cells calculated from the results of flow cytometry analysis.  indicates $p<0.01$ and * indicates $p<0.001$ by two-tailed Student's t test.

FIG. 35

Cytograms (upper) showing the results of CD34 and CD43 or CD11b and CD11c surface antigen analysis of human iPS cell-derived differentiated cells produced by feeder-free differentiation induction method (Comparative Example 1) described in Example 3(4) and Non Patent Literature (Gene Therapy 2011 18, 874-883). A table (lower) showing the CD34-positive cell frequency on day 18 of culture and the CD11b-positive cell frequency on day 25 of culture. N.D. indicates Not Detected.

[Description of Embodiments]

The Description of Embodiments is explained in detail in the following.

In one embodiment, the present invention relates to a production method of professional antigen-presenting cells, including inducing expression of c-MYC, BMI1, and MDM2 in myeloid cells (MC) to obtain proliferative myeloid cells (pMC), and inducing expression of GM-CSF and/or M-CSF in the aforementioned pMC to obtain professional antigen-presenting cells (pAPC).

Professional antigen-presenting cells (pAPC) having antigen-presenting ability could be obtained ex vivo from myeloid cells for the first time by the present production method.

In the present invention, the myeloid cell is a generic term for monocytes, macrophages, dendritic cells, and progenitor cells belonging to the cell lineages that differentiate into these cells, among leukocytes differentiated from stem cells. Preferably, the myeloid cells are myeloid cells differentiated from pluripotent stem cells. In the following, myeloid cells are also referred to as MCs.

In the present invention, the "stem cell" refers to a cell that maintains, even after cell division, the same differentiation potency into a cell having a specific function as before the cell division.

In the present invention, the pluripotent stem cell refers to a stem cell that can be cultured in vitro while maintaining an undifferentiated state and has the ability (pluripotency) to differentiate into all cells (tissues derived from three germ layers (ectoderm, mesoderm, endoderm)) constituting a living body except the placenta. Embryonic stem cells (ES cells) isolated from embryos after fertilization and before the formation of three germ layers, embryos after the organogenesis stage including primordial germ cells, and fetuses or fetuses are also induced in the "pluripotent stem cells". Preferably, the pluripotent stem cells in the present invention are induced pluripotent stem cells.

In the present invention, the "induced pluripotent stem cell" refers to cells in which pluripotency is induced by directly reprogramming somatic cells that have once lost their pluripotency by expressing several types of genes such as Oct3/4, Sox2, Klf4, Myc, and the like (hereinafter to be also referred to as iPSC or iPS cells). The "induced pluripotent stem cell" is also included in the "pluripotent stem cell". Pluripotent stem cells can be produced by known methods. As for the production methods, for example, the methods for human induced pluripotent stem cells so are described in, for example, Cell, 2007, 131(5) pp. 861-872 and Kitayama, S. et. al. (Stem Cell Reports. 6: 213-227, (2016)), and the methods for mouse induced pluripotent stem cells are described in Cell, 2006, 126(4) pp. 663-676. "Pluripotent stem cells" can also be obtained from embryo-engineered animals including cloned embryos, transgenic animals, and genome-edited mutant animals. It is known that pluripotent stem cells can be differentiated into cells of various cell types, including myeloid cells. Professional antigen-presenting cells (pAPC) prepared from induced pluripotent stem cells are referred to as iPSC-derived professional antigen-presenting cells (ipAPC).

Human or mouse iPSCs can be maintained and expanded using the regenerative medicine medium StemFit (Ajinomoto). Laminin 511 may be added at this time. In addition, a lock inhibitor such as Y-27632 may be added to the medium at about 10 μM in order to reduce or remove iPSC damage due to dissociation of cells for passage culture of the cells.

Pluripotent stem cells can be obtained from designated institutions, and commercially available products can also be purchased. For example, human embryonic stem cells KhES-1, KhES-2, and KhES-3 are available from The Institute for Frontier Life and Medical Sciences, Kyoto University. EB5 cells, which are mouse embryonic stem cells, are available from RIKEN, and the D3 strain is available from ATCC.

Pluripotent stem cells can be maintained and cultured by known methods. For example, human pluripotent stem cells can be maintained by culturing in a medium supplemented with KnockOut (trade mark) Serum Replacement (Invitrogen). Mouse pluripotent stem cells can be maintained by adding fetal bovine serum (FBS) and Leukemia Inhibitory Factor (LIF) and culturing under feeder free.

In the present invention, proliferative myeloid cells refer to myeloid cells that can be cultured for a long term of 3 months or longer, and that have superior proliferative capacity compared to myeloid cells normally present in embryo or adults. In the following, proliferative myeloid cells are also referred to as pMCs.

In the present invention, professional antigen-presenting cells are cells specialized in antigen presentation that express not only human leukocyte antigen (HLA) class I molecules possessed by general nucleated cells, but also HLA class II molecules. They include macrophages, dendritic cells, B cells, and the like. In the present specification, the professional antigen-presenting cells are also referred to as pAPCs.

In the present invention, "c-MYC", "BMI1", "MDM2", "GM-CSF" and "M-CSF" refer to genes of c-MYC, BMI1, MDM2, GM-CSF, and M-CSF of any species, or homologues or orthologues thereof, having an activity of inducing differentiation from myeloid cells derived from pluripotent stem cells of human or mammals other than human into professional antigen-presenting cells.

For example, when inducing differentiation into human professional antigen-presenting cells derived from pluripotent stem cells, human c-MYC, BMI1, MDM2, GM-CSF, and M-CSF, and genomic DNA or cDNA of these mutants are used.

Furthermore, genomic DNA or cDNA of c-MYC, BMI1, MDM2, GM-CSF and/or M-CSF derived from other biological species can also be used. Similarly, for professional antigen-presenting cells derived from pluripotent stem cells of biological species other than human, genomic DNA or cDNA of c-MYC, BMI1, MDM2, GM-CSF and/or M-CSF derived from the biological species can be used. Furthermore, when the target cells can be obtained, genomic DNA or cDNA of c-MYC, BMI1, MDM2, GM-CSF and/or M-CSF derived from other biological species can also be used.

Sequence information of various biological species of the proteins, genomic DNAs or cDNAs of "c-MYC", "BMI1", "MDM2", "GM-CSF", and "M-CSF" of the present invention can be obtained, for example, from sources well known to those skilled in the art, such as the Gene database of the National Center for Biotechnology Information (NCBI).

In the present invention, to induce expression means to produce a desired gene or protein in a cell and, in some cases, to cause secretion outside the cell to exhibit the function of the gene or protein.

In the present invention, provided by transfection means that a desired gene is introduced into a specific cell, and the gene or a protein encoded by the gene is produced in the cell, or in some cases, secreted outside the cell to exhibit the function of the protein.

The desired gene or protein in the present invention includes “c-MYC”, “BMI1”, “MDM2”, “GM-CSF”, “M-CSF”, and the like.

In the present invention, c-MYC, BMI1, and MDM2 are preferably provided by transfection into myeloid cells. In addition, GM-CSF and/or M-CSF are/is provided by transfection into proliferative myeloid cells.

In one embodiment of the present invention, the present invention further relates to a production method of professional antigen-presenting cells, including differentiating myeloid cells (MC) from pluripotent stem cells by the following method (i) or (ii):

(i) a step of performing a double-layer culture of embryoid body (EB) induced from the aforementioned pluripotent stem cells on feeder cells in a medium containing VEGF, and further culturing same in a medium containing VEGF, SCF, and TPO, or (ii) a step of performing a monolayer culture of embryoid body induced from the aforementioned pluripotent stem cells in a medium containing BMP-4, VEGF, and SCF without feeder cells, and further culturing same in a medium containing VEGF, TPO, and GM-CSF.

The “embryoid body” in the present invention refers to cell mass formed by adhesion of undifferentiated pluripotent stem cells. Due to the close cell-to-cell interaction in the cell mass, the repertoire of cell differentiation of the pluripotent stem cells that constitute the cell mass is limited, which resembles an embryo in the developmental stage in which blastoderm is formed after implantation.

The size of the embryoid body in the present invention is not particularly limited. The diameter is preferably 50 to 1000 μm, further preferably 50 to 500 μm, particularly preferably 50 to 200 μm. When the size of the embryoid body is larger than the above-mentioned range, the oxygen supply to the inside of the embryoid body may be insufficient and cell necrosis may occur. When the size of the embryoid body is smaller than the above-mentioned range, single cells may undergo cell death due to apoptosis without forming an embryoid body. Mouse embryoid body may be cultured using mouse mesenchymal C3H10T1/2 cells or mouse bone marrow-derived interstitial OP9 cells as feeder cells. Human embryoid body can be cultured without using feeder cells.

The “VEGF”, “SCF”, “TPO”, “BMP-4”, and/or “GM-CSF” of the present invention refer to VEGF, SCF, TPO, BMP-4, and/or GM-CSF protein of any species, or homologues or orthologues thereof, having an activity of inducing differentiation from pluripotent stem cells of human or mammals other than human into myeloid cells (MC).

As the “VEGF”, “SCF”, “TPO”, “BMP-4”, and/or “GM-CSF” in the present invention, VEGF, SCF, TPO, BMP-4 and/or GM-CSF protein of the biological species other than the biological species of the embryoid body to be cultured, or variants of VEGF, SCF, TPO, BMP-4 and/or GM-CSF protein of the same biological species as the biological species of the embryoid body to be cultured can be used, provided that they have the same level of differentiation-inducing activity as that of “VEGF”, “SCF”, “TPO”, “BMP-4” and/or “GM-CSF” of the biological species of the embryoid body to be cultured.

In the present specification, Flt-3L, IL-3, and/or bFGF are/is also used at times together with the aforementioned VEGF, SCF, TPO, BMP-4, and/or GM-CSF, and the like when culturing cells in the present invention. These can be obtained, for example, from sources well known to those skilled in the art, such as the Gene database of the National Center for Biotechnology Information (NCBI). As the gene-recombinant protein reagent, for example, Recombinant Human Flt-3 Ligand/FLT3 L Protein (308-FKN), Recombinant Human IL-3 Protein (203-IL), Recombinant Human FGF basic/FGF2/bFGF (145 aa) Protein (3718-FB), Recombinant Human VEGF 165 Protein (293-VE), Recombinant Human SCF Protein (255-SC), Recombinant Human Thrombopoietin Protein (288-TP), Recombinant Human BMP-4 Protein (314-BP), and Recombinant Human GM-CSF Protein (215-GM) may also be purchased from R&D Systems (https://www.rndsystems.com/).

Sequence information of various biological species of the proteins, genomic DNAs or cDNAs of “VEGF”, “SCF”, “TPO”, “BMP-4” and/or “GM-CSF” of the present invention can be obtained, for example, from sources well known to those skilled in the art, such as the Gene database of the National Center for Biotechnology Information (NCBI), As the aforementioned gene and protein, those of the same kind as the pluripotent stem cells to be used are preferred. For example, when the pluripotent stem cells are derived from human, it is preferable to use VEGF, SCF, TPO, BMP-4, GM-CSF, Flt-3L, IL-3, and/or bFGF derived from human. When the pluripotent stem cells are derived from mouse, it is also preferable to use the gene or protein derived from mouse.

In the present invention, the “medium containing substance X” means a medium supplemented with exogenous substance X or a medium containing exogenous substance X, and the “medium free of substance X” means a medium not supplemented with exogenous substance X or a medium not containing exogenous substance X. As used herein, the “exogenous substance X” means a substance X foreign to the cell or tissue cultured in the medium, and does not include endogenous substance X produced by the cell or tissue.

For example, the “medium containing VEGF” means a medium supplemented with exogenous VEGF or a medium containing exogenous VEGF. While the dose of VEGF may be influenced by other growth factors and the like, 0.2 ng/mL to 200 ng/mL is preferred, 2 ng/mL to 100 ng/mL is further preferred, and 5 ng/mL to 50 ng/mL is particularly preferred. The “medium free of VEGF” is a medium not supplemented with exogenous VEGF or a medium not containing exogenous VEGF.

Similarly, as regards SCF, TPO, BMP-4, and GM-CSF, a medium containing SCF, TPO, BMP-4 and/or GM-CSF means a medium supplemented with exogenous SCF, TPO, BMP-4 and/or GM-CSF or a medium containing exogenous SCF, TPO, BMP-4 and/or GM-CSF. Therefore, while the dose of SCF, TPO, BMP-4 and/or GM-CSF may be influenced by other growth factors and the like, 0.2 ng/mL to 200 ng/mL is preferred, 2 ng/mL to 100 ng/mL is further preferred, 5 ng/mL to 50 ng/mL is more preferred, 5 ng/mL to 15 ng/mL is particularly preferred, and 10 ng/mL is most preferred.

The “medium free of SCF, TPO, BMP-4 and/or GM-CSF” means a medium not supplemented with exogenous VEGF or a medium not containing exogenous SCF, TPO, BMP-4 and/or GM-CSF.

αMEM supplemented with 20% fetal bovine serum (FBS) can be used as a medium for mouse embryoid body in the present invention. Mouse mesenchymal C3H10T1/2 cells or mouse bone marrow-derived interstitial O9 cells can be used as feeder cells. A completely synthetic medium, X-VIVO15 (Lonza), can be used as a medium for human embryoid body. For differentiation from hematopoietic progenitor cells (HPCs), the CD11b positive fraction can be concentrated with magnetic beads.

As the medium, cMEM supplemented with 20% FBS and the like can be used.

The proliferative myeloid cell (pMC) of the present invention can be transfected with the GM-CSF and/or M-CSF gene.

In the present invention, the "feeder cell" is other cell type used to adjust the culture conditions for undifferentiated maintenance culture and differentiation induction culture of iPS cells. Feeder cells that underwent mitomycin C treatment or radiation irradiation in order to stop the growth thereof are used. Mouse-derived fibroblasts can be used for undifferentiated maintenance culture, and mouse bone marrow-derived interstitial cells OP-9, mouse-derived mesenchymal cells C3H10T1/2, and the like can be used for differentiation induction culture.

In the present invention, the "double-layer culture" refers to seeding and coculturing the iPS cells or embryoid body of interest in a feeder cell layer culture system cultured in advance in a predetermined culture container. In the present invention, the "monolayer culture" means culturing a single cell type being adhered to a container for tissue culture.

In the present invention, the monolayer culture without feeder cells refers to seeding the iPS cells or embryoid body of interest in a culture container and performing static culture.

In addition, in one embodiment of the present invention, the present invention further relates to a production method of professional antigen-presenting cells, including forming an embryoid body from pluripotent stem cells by the following method:

(i) seeding a single cell dispersion of pluripotent stem cells in a container for cell mass-forming culture to form an embryoid body (EB), wherein (ii) the aforementioned container has fine spheroid wells at the bottom, and does not have a flat surface between adjacent spheroid wells.

"Forming an embryoid body" means dissociating pluripotent stem cells proliferating in an undifferentiated state to obtain a single-cell dispersion of the pluripotent stem cells, and forming qualitatively uniform cell mass by suspension culture or static culture under conditions in which pluripotent stem cells adhere and aggregate. The formation of embryoid body is confirmed by visual observation of the presence of viable cells under a microscope.

In the present specification, the "suspension culture" refers to culturing under conditions in which cells or cell masses are kept in a suspending state so that they do not adhere to substrates such as the bottom, walls, and the like of culture containers.

The incubator used for suspension culture is not particularly limited as long as it is capable of "suspension culture", and can be appropriately determined by those skilled in the art. Examples of such incubator include flask, tissue culture flask, dish, petri dish, tissue culture dish, multidish, microplate, microwell plate, micropore, multiplate, multiwell plate, chamber slide, schale, tube, tray, culture bag, and roller bottle. These incubators are preferably cell non-adhesive so that suspension culture can be performed. As the cell non-adhesive incubator, an incubator free of an artificial surface treatment (for example, coating treatment with an extracellular matrix or the like) for the purpose of improving adhesion to cells and the like can be used.

In the present invention, it is preferable to rapidly aggregate pluripotent stem cells to form pluripotent stem cell-derived embryoid body. When cell masses of pluripotent stem cells are formed in this way, transferred to a medium supplemented with VEGF at a concentration of 50 ng/mL, and cultured, the cells of the cell mass can be differentiated from hematopoietic stem cells into the cell lineage of myeloid cells in the same manner as blood island in the yolk sac.

Experimental operation for forming embryoid body includes, for example, a method of confining cells in a small space using a culture container such as a plate with a large number of small-diameter holes (wells) (e.g., 96-well plate), a container for cell mass-forming culture and the like, and a method of aggregating cells by briefly centrifuging them in a small centrifuge tube. The culture conditions for aggregates of cells or pluripotent stem cells include spinning culture, shaking culture, and other suspension cultures. In addition, static culture can also be performed on the condition that the adhesion between the pluripotent stem cells and the surface of the substrate of the culture container that comes into contact with the cells is reduced or suppressed by subjecting the substrate surface of the culture container to a treatment in advance to make same hydrophobic or the like.

The formation of embryoid body as cell mass of pluripotent stem cells and the differentiation of embryoid body cells into myeloid cells can be determined using microscopy and FACS based on characteristics including, but not limited to, confirmation of the size and cell number of embryoid body, confirmation of the microscopic morphology of embryoid body under culture, confirmation of histological or cytochemical findings, and/or confirmation of expression of differentiation and undifferentiation markers, uniformity thereof, regulation of expression of differentiation markers, synchronicity thereof, or reproducibility of differentiation efficiency between embryoid bodies, and the like.

In the present invention, when a certain cell is "positive" for a certain marker, an average fluorescence intensity ratio of the positive cells to the negative control, as measured by flow cytometry of the cells, of 10 times or more is +, 2 times or more to less than 10 times is low, and less than 2 times is −. In the present invention, moreover, high or low expression of a gene in a cell means an expression level of the gene with respect to housekeeping gene β actin, GAPDH (glyceraldehyde-3-phosphate dehydrogenase), HPRT 1 (hypoxanthine phosphoribosyltransferase 1), or β2-microglobulin, as measured by the real-time PCR method, and is high when it is 1-fold or more and low when it is less than 1-fold.

In the present invention, the single cell dispersion is prepared by washing cultured cells with PBS or the like, treating them with a cell dissociation solution trypsin-EDTA (Life Technologies) or TrypLE Select (Life Technologies) for 4 to 5 minutes, further washing them with PBS or the like, centrifuging them to obtain pellets of the desired cells, and resuspending the pellets by pipetting with a desired culture solution or the like.

In the present invention, the container for cell mass-forming culture means a container in which cells seeded during culture can form cell aggregates without adhering to the container. Preferably, the container is provided with fine spheroid wells on its bottom, which is the culture surface, and does not have a flat surface between adjacent spheroid wells, in which the adjacent spheroid wells are separated by a curved surface that slopes toward any spheroid well. Since a surface treatment to suppress adhesiveness of cells is applied to the curved surface, most of the cells seeded in the culture container drop into any of the spheroid wells.

An example of the container is a container in which spheroid wells with a diameter of about 400 to 800 μm and a depth of 100 to 800 μm are uniformly placed without gaps on the culture surface (bottom) up to the wall surface. Preferably, the spheroid well has a diameter of 400 to 500 μm and a depth of 50 to 200 μm. A container with spheroid wells having a diameter of about 500 μm and a depth of about 400 μm, a container with spheroid wells having a diameter of about 800 μm and a depth of about 400 μm, and a container with spheroid wells having a diameter of about 800 μm and a depth of about 300 μm are more preferred. A container with spheroid wells having a diameter of about 400 μm and a depth of 100 to 200 μm is most preferred.

As the container, one in which spheroid wells are uniformly processed without gaps on the culture surface (bottom) up to the wall surface is preferred. Such container does not have a flat surface between adjacent spheroid wells and seeded single cell suspension drops into any of the spheroid wells, thus forming uniform aggregates. More preferred is a micro-fabricated cell culture container (EZSPHERE (registered trade mark)) manufactured by AGC.

The present invention further relates to a method for producing professional antigen-presenting cells, including (i) seeding pluripotent stem cells in a container for cell mass-forming culture that has fine spheroid wells at the bottom, and does not have a flat surface between adjacent spheroid wells to form an embryoid body (EB), (ii) obtaining myeloid cells (MC) from the aforementioned embryoid body by the following method (ii)-1 or (ii)-2:

(ii)-1 performing a double-layer culture of the aforementioned embryoid body on feeder cells in a medium containing VEGF, and further culturing same in a medium containing VEGF, SCF, and TPO, or (ii)-2 performing a monolayer culture of the aforementioned embryoid body in a medium containing BMP-4, VEGF, and SCF without feeder cells, and further culturing same in a medium containing VEGF, TPO, and GM-CSF, (iii) inducing expression of c-MYC, BMI1, and MDM2 in the myeloid cells (MC) obtained in (ii) to obtain proliferative myeloid cells (pMC), and (iv) inducing expression of GM-CSF and/or M-CSF in the proliferative myeloid cells (pMC) obtained in (iii) to obtain professional antigen-presenting cells (pAPC).

In addition, in one embodiment of the present invention, the present invention relates to a production method of professional antigen-presenting cells, in which c-MYC, BMI1, and MDM2 are provided by transfection into myeloid cells (MC), and GM-CSF and/or M-CSF are/is provided by transfection into proliferative myeloid cells (pMC).

In addition, in one embodiment of the present invention, the present invention further relates to a production method of professional antigen-presenting cells, in which the aforementioned embryoid body (EB) has a size of 50 to 200 μm.

When the size of the embryoid body is 50 to 200 μm, pluripotent stem cells can be efficiently differentiated into myeloid cells in both cases of on-feeder differentiation induction and feeder-free differentiation induction.

In addition, in one embodiment of the present invention, the present invention further relates to a method for producing professional antigen-presenting cells, further including exposing the aforementioned professional antigen-presenting cells (pAPC) to radiation (R/pAPC step) and/or introducing a suicide gene into pAPC.

In the present invention, the radiation may be any radiation, including gamma ray, X-ray, UV, visible light, infrared ray, and microwave radiation. X-ray is preferred.

In the present invention, irradiating radiation means exposing cells to radiation. In the present invention, when the professional antigen-presenting cells are irradiated with radiation, any absorbed irradiation dose may be irradiated as long as the professional antigen-presenting cells after radiation irradiation can maintain the ability to promote the proliferation of T cells even though they lose their self-proliferation potency.

In the present invention, introducing a suicide gene into pAPC means that the suicide gene is retained in the pAPC and the suicide gene is in a state of functioning.

The suicide gene refers to a gene that can cause death of the cell into which it has been introduced. The method of eliminating cells by suicide genes is performed by first introducing into cells a suicide gene that encodes a protein that causes the death of cells into which the suicide gene has been introduced, only when the suicide gene is activated by a specific compound. The suicide gene may encode an enzyme that selectively converts a nontoxic compound into a highly toxic metabolite. As a result, cells expressing the enzyme are specifically eliminated. In some embodiments, the aforementioned suicide gene is the herpes virus thymidine kinase (HSV-tk) gene and the trigger is ganciclovir, AP1903 (can be purchased from MedChemExpress), or YM-155 (can be purchased from Cayman Chemical). In another embodiment, the aforementioned suicide gene is the *Escherichia coli* cytosine deaminase (EC-CD) gene and the trigger is 5-fluorocytosine (5-FC) (Barese et al., Mol. Therap. 20(10):1932-1943 (2012), Xu et al., Cell Res. 8:73-8 (1998), both of which are incorporated herein by reference in their entireties).

In another embodiment, the aforementioned suicide gene is an inducible caspase protein. The inducible caspase protein contains at least a portion of a caspase protein capable of inducing apoptosis. In a preferred embodiment, the aforementioned inducible caspase protein is iCasp9. It contains the sequence of human FK506 binding protein (FKBP12) with F36V mutation and linked to a gene encoding human caspase9 via a series of amino acids. FKBP12-F36V binds with high affinity to AP1903, a low-molecular weight dimerizing agent. Therefore, the suicide function of iCasp9 in the present invention is triggered by administering a chemical inducer of dimerization (CID). In some embodiments, the aforementioned CID is low-molecular weight drug AP1903. Dimerization rapidly induces apoptosis (WO 2011146862; Stasi et al, N. Engl. J. Med 365; 18 (2011); Tey et al., Biol. Blood Marrow Transplant. 13:913-924 (2007), each of which is incorporated herein by reference in its entirety).

As a method for introducing the suicide gene, the gene can be introduced into cells by using a gene transfer vector containing the desired suicide gene. The gene transfer vector includes viral vector, non-viral vector, and the like. Examples of the viral vector include lentiviral vector and retroviral vector, and lentiviral vector is preferred. The non-viral vector includes transposon vector and plasmid DNA. In another method, the suicide gene can also be introduced into the desired cells by incorporating the suicide gene into genomic DNA by genome editing.

Surprisingly, the present inventors have found that when the professional antigen-presenting cells are exposed to radiation, they lose their self-proliferation potency, but when they are irradiated with radiation to the extent that the professional antigen-presenting cells can maintain the ability to promote the proliferation of T cells and are administered in vivo, they disappear from the body in at least 3 to 4 days after the in vivo administration.

The irradiation dose of radiation in the present invention may be any as long as it is within a range in which the irradiated professional antigen-presenting cells disappear from the body within 3 to 4 days after administration in vivo. For example, 5 to 100 Gy, 10 to 85 Gy, 10 to 75 Gy, 10 to 65 Gy, 10 to 55 Gy, and the like can be mentioned. It is preferably 10 Gy to 85 Gy, more preferably 10 Gy to 75 Gy, further preferably 10 Gy to 65 Gy, particularly preferably 10 Gy to 55 Gy, most preferably 10 Gy to 40 Gy.

When mouse pAPC is irradiated with radiation, the irradiation dose of radiation in the present invention is preferably 5 to 85 Gy, more preferably 10 to 85 Gy, further preferably 20 to 85 Gy, and particularly preferably 25 to 85 Gy. When the dose is within the above-mentioned range, irradiated mouse pAPCs disappear from the body within 3 to 4 days after administration in vivo.

When human pAPC is irradiated with radiation, the irradiation dose of radiation in the present invention is preferably 5 to 80 Gy, more preferably 10 to 80 Gy, further preferably 20 to 80 Gy, and particularly preferably 20 to 40 Gy. When the dose is within the above-mentioned range, irradiated human pAPCs disappear from the body within 3 to 4 days after administration in vivo.

T cells are lymphocytes that recognize antigens presented from pAPC via HLA/MHC and cause cellular immune responses to damage and kill cells regarded as exogenous substances. Naive T cells are surface marker CD3-positive cell populations differentiated from hematopoietic stem cells, and subtypes such as CD4-positive helper T cells, CD8-positive killer T cells, and Foxp3-positive regulatory T cells, and the like exist depending on the co-expressed surface markers. In the present invention, CD8-positive killer T cells specific to the antigen loaded on pAPC are particularly desirable as cytotoxic T cells induced by pAPC.

In addition, in one embodiment of the present invention, the present invention further relates to a professional antigen-presenting cell (pAPC) produced by the production method described in the present specification. In addition, in one embodiment of the present invention, the present invention relates to a professional antigen-presenting cell (pAPC) that is produced by the production method described in the present specification, and disappears, when administered to a living body after radiation irradiation, in at least 3 or 4 days after the administration to the living body.

In addition, in one embodiment of the present invention, the present invention relates to a professional antigen-presenting cell (pAPC) that shows low expression of CD11b/c and expression of CD74.

In addition, in one embodiment of the present invention, the present invention relates to a professional antigen-presenting cell (pAPC) that shows low expression of CD11b/c and expression of CD74 and CD33.

This professional antigen-presenting cell can be produced by so the method described in the present specification.

CD11b is a differentiation marker of myeloid cells expressed on the cell surface. It can be detected by performing immunostaining using an anti-CD11b antibody and analyzing with a flow cytometer.

CD11c is a differentiation marker of dendritic cells expressed on the cell surface. It can be detected by performing immunostaining using an anti-CD11c antibody and analyzing with a flow cytometer.

CD33 is a differentiation marker of myeloid cells expressed on the cell surface. It can be detected by performing immunostaining using an anti-CD33 antibody and analyzing with a zo flow cytometer.

CD74 is a marker expressed on the cell surface involved in cross-presentation. It can be detected by performing immunostaining using an anti-CD74 antibody and analyzing with a flow cytometer.

To express means that the average fluorescence intensity ratio of positive cells to the negative control is 2 times or more.

Low expression means that the average fluorescence intensity ratio of positive cells to that of negative controls is 2 times or more and less than 10 times.

The present inventors surprisingly found for the first time that a professional antigen-presenting cell that shows low expression of CD11b and c and expression of CD74, or CD74 and CD33 promotes antigen non-specifically the proliferation of T cells, particularly naive T cells that express CD8. In addition, the present inventors surprisingly found that the professional antigen-presenting cell subjected to radiation irradiation promotes proliferation of T cells expressing CD8 in the living body but the professional antigen-presenting cell disappears from the living body in 3 to 4 days after the administration.

To disappear means that the cell administered to the living body cannot be detected or is immunologically eliminated. Specifically, for example, changes over time in the photographed images of in vivo imaging and the total flux of luciferase luminescence are confirmed by the method described in Example 8 below, and disappearance can be confirmed by being below detection limits. In addition, disappearance can be confirmed by equivalent methods using not only luciferase but also fluorescent dyes, radioactive compounds, and the like.

Furthermore, after administering the professional antigen-presenting cells of the present invention exposed to radiation to a living body, the disappearance can also be confirmed by low expression of CD11b/c and the fact that T cells showing expression of CD33 and CD74 are below detection limit in a blood sample of the living body.

Any method may be used as long as it can confirm the professional antigen-presenting cell of the present invention and T cells that show low expression of CD11b/c and expression of CD33 and CD74. When the presence of the antigen-presenting cell or T cell cannot be detected by such methods, it can be determined that the professional antigen-presenting cells of the present invention have disappeared.

In addition, in one embodiment of the present invention, the present invention further relates to the aforementioned professional antigen-presenting cell (pAPC) having self-proliferation potency and showing apoptosis resistance.

This professional antigen-presenting cell can be produced by the method described in the present specification.

The self-proliferation potency is to have the ability to perform cell proliferation by activating the cell proliferation signal by the autocrine cytokine produced by the cell itself. The self-proliferation potency can be confirmed by proliferation of cells seeded in a cytokine-free culture medium such as RPMI-1640 medium containing 10% fetal bovine serum (FBS). Cell proliferation can be confirmed and evaluated by methods such as cell counting before and after culture, MTT assay, [$^{3}$H]-thymidine uptake activity, and the like.

Apoptosis resistance is the property of being able to avoid cell death due to apoptosis. The apoptosis resistance can be evaluated by staining cells with fluorescent dye-labeled reagents FITC-labeled Annexin-V, 7-AAD, and PI, which can detect cell death, and then analyzing them with a flow cytometer.

In addition, in one embodiment of the present invention, the present invention further relates to a method for promoting proliferation of T cells that express antigen non-specific or antigen specific CD8 in vivo and in vitro by coculturing the aforementioned professional antigen-presenting cells or GM-CSF, and naive T cells expressing CD8 in vitro.

Furthermore, in one embodiment of the present invention, the present invention relates to a method for producing T cells that express antigen non-specific or antigen specific CD8, using the aforementioned method for promoting proliferation of T cells that express antigen non-specific or antigen specific CD8.

This professional antigen-presenting cell can be produced by the method described in the present specification.

Also, the present inventors have surprisingly found that GM-CSF alone can promote antigen-nonspecifically the proliferation of T cells, particularly T cells expressing CD8.

The naive T cells that express CD8 refer to a cell population that has not undergone antigen stimulation and expresses CD3, which is a cell surface marker for T cells. The antigen non-specific T cells refer to a T cell population that maintains diversity of T cell receptors, and is not biased towards a population of T cells having a T cell receptor recognizing a specific antigen.

This professional antigen-presenting cell may be a professional antigen-presenting cell loaded with a desired antigen.

The antigen specific T cell is a T cell that expresses a T cell receptor that specifically recognizes a specific antigen by stimulation of antigen-presenting cells loaded with a desired antigen.

In the present invention, the "antigen" refers to all proteins, sugar chains and other molecules that can elicit an immune response, particularly a cellular immune response, specific to the antigen. As the antigen in the present invention, antigens are preferred that elicit cellular immunity specific to autologous cells that are harmful to the body, such as cancer cells, cells with neurodegeneration or other tissue degeneration, cells that have come to cause adverse reactions to the body after physiological or pathological processes, and the like, in order to eliminate these cells. In the present invention, cancer specific antigens are particularly preferred.

In the present invention, the "cancer specific antigen" is a protein, sugar chain, or other molecule that is expressed only when cells of a specific cell type become malignant and proliferate, and refers to an antigen that does not exist in a living body without such malignant cells. The so-called carcinoembryonic antigen, which is expressed only up to the embryonic or fetal stage in normal development but is expressed in cancer cells, is one of the typical cancer-specific antigens.

Furthermore, the professional antigen-presenting cell may be irradiated with radiation in vitro.

Irradiation of radiation on the professional antigen-presenting cells of the present invention by the aforementioned method promotes proliferation of T cells expressing antigen specific or non-specific CD8 in vivo, after administration of the cells to a living body. The professional antigen-presenting cells can be eliminated from the body within 3 to 4 days after administration to the body.

In addition, in one embodiment of the present invention, the present invention further relates to a pharmaceutical composition for inducing proliferation of T cells expressing CD8, containing the aforementioned professional antigen-presenting cells.

In the present invention, the "pharmaceutical composition for inducing proliferation of T cells" refers to a pharmaceutical composition for inducing proliferation of T cells. In the present invention, it refers to a pharmaceutical composition for acting on and inducing proliferation of naive T cells that are in or near a dormant state with respect to cell proliferation. It refers to cytokines themselves that promote the proliferation of T cells and cells that produce and secrete the cytokine. In addition, it includes a pharmaceutical composition that not only induces proliferation, but also induces T cells that proliferate with cytotoxicity as specific cytotoxic T cells. This pharmaceutical composition can activate immunity in the living body.

In addition, in one embodiment of the present invention, the present invention includes a method for producing T cells expressing CD8 for administration into a body, including loading an antigen on the aforementioned professional antigen-presenting cells of the present invention, exposing the aforementioned professional antigen-presenting cell loaded with the antigen to radiation, and coculturing in vitro the aforementioned professional antigen-presenting cell exposed to radiation, and naive T cells that express CD8 to promote proliferation of the T cells that express antigen specific CD8, and T cells expressing CD8 that are produced by this method.

T cells expressing CD8 that are produced by this method can be administered into the body. The radiation-irradiated professional antigen-presenting cell in this method can disappear from the body in 3 to 4 days after administration to the body. T cells expressing CD8 that are produced by this method may be T cells expressing antigen specific CD8 loaded on the aforementioned professional antigen-presenting cells, and the antigen may be a cancer-specific antigen.

The professional antigen-presenting cells or T cells expressing CD8 of the present invention can be used in combination with anticancer agents and/or other cancer treatment methods.

In addition, the professional antigen-presenting cells or T cells expressing CD8 of the present invention can be used in combination with immune checkpoint inhibitors.

In the present specification, the anticancer agents and/or other methods for cancer treatment include, but are not limited to, surgical therapy to physically remove cancer cells; chemotherapy that administers chemical substances and chemotherapeutic agents including, but not limited to, alkylating drugs, platinum compounds, antimetabolites, topoisomerase inhibitors, microtubule inhibitors, and antibiotics; immunotherapy in which immune cells attack cancer cells as non-self and immunotherapeutic agents; and radiation therapy that uses irradiation of radiation including, but not limited to, X-rays, electron beams, gamma rays, and neutron beams, to inhibit the proliferation of cancer cells and kill them. The chemotherapy drugs for treating cancer include 6-O-(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, hepromycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofour, cytarabine, methyltestosterone, testosterone propionate, testosterone enanthate, mepitiostane, fosfestrol, chlormadinone acetate, leuprorelin acetate, buserelin acetate, and the like. The aforementioned other treatment methods can also include removal of cancer tissues by surgery and/or irradiation of radiation that kills cancer cells.

In the present specification, the immune checkpoint inhibitor is an anticancer agent that suppresses cancer proliferation by binding to immune checkpoint molecules that suppress the activity of T cells by antigen presentation, and inhibiting the signal transduction thereof. The immune checkpoint molecules may include both receptors and ligands that function as immune checkpoints.

In one embodiment of the present invention, the "immune checkpoint inhibitors" include, but are not limited to, for example, any antibody or compound that can inhibit binding or interaction between PD-L1 and PD-1, binding or interaction between CD80/CD86 and CTLA4, binding or interaction between CD137L and CD137, binding or interaction between MHC and LAG-3/KIR, binding or interaction between CD48 and CD244, binding or interaction between GAL9 and TIM3, binding or interaction between HVEM and BTLA/CD160, binding or interaction between CD40L and CD40, binding or interaction between OX40L and OX40, or binding or interaction between GITRL and GITR.

In another embodiment of the present invention, the "immune checkpoint inhibitor" is selected from the group consisting of, though not limited to, an anti-PD-1 antibody, an anti-PD-L1 antibody, an anti-CTLA4 antibody, an anti-B7 antibody, an anti-C27 antibody, an anti-KIR antibody, an IDO inhibitor, an anti-CD137 antibody, and an anti-TIM3 antibody.

In still another embodiment of the present invention, the "immune checkpoint inhibitor" is selected from the group consisting of, though not limited to, Atezolizumab, Durvalumab, Avelumab, Nivolumab, Pembrolizumab, Pidilizumab, BMS-936559, Ipilimumab, tremelimumab, Enoblituzumab, Varlilumab, Lirilumab, Epacadostat, Utomilumab, Urelumab, and TSR-022.

In yet another embodiment of the present invention, the "immune checkpoint inhibitor" is preferably an anti-PD-L1 antibody, an anti-PD-1 antibody, or an anti-CTLA4 antibody, more preferably an anti-PD-L1 antibody or an anti-CTLA4 antibody.

All documents referred to in this specification, and the specifications and drawings of the base patent application Nos. 2020-084821 and 2020-149486 are incorporated herein by reference in its entirety.

The Examples of the present invention described below are for illustrative purposes only and are not intended to limit the technical scope of the present invention. The technical scope of the present invention is limited only by the description of the claims. Modifications of the present invention, such as addition, deletion, and substitution of the constituent elements of the present invention, can be performed without departing from the gist of the present invention.

EXAMPLE

Example 1: Production of Human iPSC-Derived Embryoid Body

Human iPSC was produced by the method described in Kitayama, S. et al. (Stem Cell Reports. 6: 213-227, (2016)). The maintenance culture of human iPSC was performed using StemFit AK02N (Ajinomoto Healthy Supply), which is a medium for regenerative medicine, on polystyrene tissue culture plates coated with iMatrix511 (Nippi). The medium was changed every 1 or 2 days, and the cells were treated with the cell detachment solution TrypLE Select (Life Technologies) for 4 to 5 minutes once a week depending on the growth of the cells, and collected as a single cell dispersion. The cell dispersion was seeded in a culture container with a suitable size and culture was continued. The seeded iPSCs were cultured overnight in the presence of 10 μM Y-27632 (Wake Pure Chemical), a Rock inhibitor, and the medium was changed the next day to remove Y-27632.

The embryoid body derived from human iPSC (hereinafter to be indicated as human EB) was produced by seeding human iPSC at a given density prepared with StemFit containing 10 μM Y-27632 in a 6-well plate type cell mass-forming culture container EZ SPHERE SP (AGC Techno Glass). One to four days after the formation of embryoid bodies with a diameter of 50 to 200 μm, differentiation induction culture of Example 3 described later was performed.

Example 2: Production of Mouse iPSC-Derived Embryoid Body

Mouse iPSC was produced by the method described in Araki, R. et al. (Nature, 494:100-104. (2013)). The maintenance culture of mouse iPSC was performed using complete medium complete ESM (cESM) prepared by adding 2-mercaptoethanol (Life Technologies) at a final concentration of 55 μM and $10^4$ U/mL Leukemia Inhibitory Factor (LIF) (Merck, trade name ESGROmLIF) to ES cell medium ESM (15% KSR (Life Technologies)-containing DMEM (Wako Pure Chemical)), on feeder cells of mouse fetal fibroblast MEF (ReproCELL) seeded on a 6-well tissue culture plate.

Feeder cells were prepared by seeding MEF (ReproCELL), whose cell proliferation had been stopped by mitomycin C treatment, on a gelatin-coated dish, and used for the maintenance culture of mouse iPSCs from the day after adhesion of MEFs.

The embryoid body derived from mouse iPSC (hereinafter to be indicated as mouse EB) was produced by seeding mouse iPSC at a given density prepared with complete medium cESM in a 6-well plate type EZ SPHERE SP (AGC Techno Glass). One to four days after the formation of embryoid bodies with a diameter of 50 to 200 μm, differentiation induction culture of Example 3 described later was performed.

Example 3: Differentiation Induction of Embryoid Body into Myeloid Cell (1) Preparation of Feeder Cell A mouse-derived cultured cell line C3H10T1/2 or OP9 was seeded on a gelatin-coated dish, and the cell line was used the next day. Feeder cells used for differentiation induction of human iPSC-derived embryoid body were irradiated with 60 Gy radiation to stop proliferation and then used. BME medium (Life Technologies) containing 10% FBS was used to culture C3H10T1/2 cells, and αMEM medium (Life Technologies) containing 20% FBS was used to culture OP9 cells.

(2) On-Feeder Differentiation Induction Culture of Mouse iPSC

After culturing mouse EB prepared from mouse iPSC on feeder cells OP9 for 7 to 10 days using αMEM containing 20% FBS as a differentiation induction medium, the harvested cells were reseeded on freshly-prepared OP9 feeder. Differentiated cells containing myeloid cells were obtained by culturing for 7 to 10 days in the presence of 55 μM 2-mercaptoethanol and 50 ng/mL GM-CSF.

(3) On-Feeder Differentiation Induction Culture of Human iPSC

Human EB prepared from human iPSC was cultured on feeder cells C3H10T1/2 for 7 to 10 days in the presence of 20 ng/mL VEGF and using αMEM containing 20% FBS as a differentiation induction medium. Thereafter, the cells were cultured in the presence of 20 ng/mL VEGF, 50 ng/mL SCF, 50 ng/mL Flt-3L, 10 ng/mL TPO, and 20 ng/mL IL-3 for 7 to 10 days, and the harvested cells were reseeded on freshly-prepared OP9 feeder. The reseeded cells were cultured in the presence of 50 ng/mL SCF, 50 ng/mL Flt-3L, and 50 ng/mL GM-CSF for 7 to 10 days to obtain differentiated cells containing myeloid cells.

(4) Feeder-Free Differentiation Induction Culture of Human iPSC

Human EB produced from human iPSC was cultured for 5 to 7 days in differentiation induction medium X-VIVO15 (Lonza) in the presence of 50 ng/mL bFGF, 50 ng/mL BMP-4, 50 ng/mL VEGF, and 50 ng/mL SCF. Thereafter, the cells were cultured for 7 to 10 days in the presence of 50 ng/mL bFGF, 50 ng/mL VEGF, 50 ng/mL SCF, 50 ng/mL Flt-3L, 10 ng/mL TPO, 20 ng/mL IL-3, and 50 ng/mL GM-CSF. Thereafter, the cells were cultured for 7 to 10 days in the presence of 50 ng/mL GM-CSF, 50 ng/mL SCF, and 50 ng/mL Flt-3L to obtain differentiated cells containing myeloid cells. Although possibly affected at times by other growth factors and the like, any two concentrations within the range of 0.2 ng/mL to 200 ng/mL can be used as the upper limit and the lower limit. For example, any two concentrations from 0.2 ng/mL, 2 ng/mL, 2 ng/mL, 10 ng/mL, 20 ng/mL, 50 ng/mL, 100 ng/mL to 200 ng/mL, can be used as the upper limit and the lower limit.

Example 4: Production of Proliferative Myeloid Cells pMC by Introduction of Proliferation Gene (1) Preparation of Lentiviral Vector Human c-MYC, BMI1, and MDM2 cDNAs were synthesized by gene synthesis using the sequence information in the database of the National Center for Biotechnology Information (NCBI). A cDNA fragment of each gene was inserted into the lentiviral vector pSL or CDII-EF-MSC-IRES2-Veneus. Using the lipofection method, each of the genes introduced into the lentiviral vector pSL or CDII-EF-MSC-IRES2-Veneus as prepared above, the packaging construct pCAG-HIVgp, and the envelope and Rev construct pCMV-VSV-G-RSV-Rev was introduced into 293T cells, which are packaging cells (virus-producing cells).

Three days after gene transfer into 293T cells, the cell culture medium was collected, filtered through a filter with a pore size of 0.45 μm, and then concentrated with a Lenti-X concentrator (Clontech) to collect virus particles. After suspending the collected recombinant virus particles in a DMEM solution, they were dispensed into cryovials and stored under a −150° C. environment.

(2) Conferring Proliferation Potency by Introducing Proliferation Gene into iPSC-Derived Myeloid Cell The myeloid cells prepared in the previous section were cultured in a 48-well tissue culture plate, and in the case of mouse myeloid cells, a suspension of lentivirus expressing c-MYC was added at the same time to infect them. In the case of human myeloid cells, a suspension of lentiviral expressing c-MYC, BMI1, and MDM2 was added at the same time to infect them. From the next day of the gene transfer, the culture scale was expanded while adding the culture medium according to the proliferation of the cells. Using 20% FBS-containing αMEM as a culture medium for myeloid cells after virus infection, the cells after infection were cultured in the presence of 50 ng/mL GM-CSF and 50 ng/mL M-CSF. The transfected cells continued to proliferate for more than 3 months. The thus-produced myeloid cells having proliferation potency were named proliferative myeloid cells (pMC).

(3) Examination of the Necessity of GM-CSF and M-CSF in pMC Proliferation

After gene transfer, pMCs were collected after culturing for 2 weeks or more, seeded in a 96-well tissue culture plate ($2\times10^3$ cells/well), and cultured. Then, the proliferation rate was compared between a culture medium containing GM-CSF and M-CSF and a culture medium not containing GM-CSF and M-CSF.

0.5 mg/mL of 3-(4,5-Dimethyl-2-thiazolyl)-2,5-diphenyl-2H-tetrazolium bromide (MTT) reagent (Merck) was added every 24 hours from immediately after the start of culture in a 96-well tissue culture plate, and metabolized formazan was measured 4 hours later by absorbance at a wavelength of 595 nm. The amount of metabolized formazan is proportional to the number of cells at the time of addition of the MTT reagent, that is, the rate of cell proliferation.

FIG. 1 shows the measurement results of the MTT assay. From the result, pMC proliferation required about 50 ng/mL of GM-CSF or M-CSF in the culture medium. In addition, the combined use of GM-CSF and M-CSF was effective in promoting proliferation.

(4) pMC Morphology and Surface Antigen Analysis

The obtained pMC did not show any change in cell morphology due to the introduction of c-MYC, BMI1, or MDM2, and retained the distorted morphology with protrusions that myeloid cells show.

pMCs were collected by a pipetting operation and stained with an anti-CD11b antibody, an anti-CD11c antibody, an anti-CD33 antibody, or an isotype-compatible control antibody. The cells were then washed twice with 2% FBS-containing PBS or PBS. The cells after washing were analyzed using a flow cytometer analyzer (trade name: BD Accuri C6 Flow Cutometer, manufactured by Beckton Dickinson). FIG. 2 shows the results of surface antigen analysis by a flow cytometer after antibody staining. From the results of this analysis, it was found that the expression of CD11b and CD11c, which were expressed in differentiated cells, on the cell surface decreased in pMCs. In addition, it was found that pMCs express CD33, which is a physiologically existing myeloid cell marker, on the cell surface.

Example 5: Production of iPSC-Derived Professional Antigen-Presenting Cell (ipAPC)

(1) Preparation of Lentiviral Vector (Human)

Human GM-CSF and M-CSF cDNAs were synthesized by gene synthesis, cDNA fragments of each gene were inserted into the lentiviral vector pSL in the same manner as in Example 4(1), and virus particles were prepared. After suspending the collected recombinant virus particles in a DMEM solution, they were dispensed into cryovials and stored under a −150° C. environment.

(2) Transfer of GM-CSF, M-CSF Genes into iPSC-Derived pMC (Human, Mouse)

The human proliferative myeloid cells pMC prepared in Example 4(2) were cultured in a 48-well tissue culture plate, and a suspension of lentivirus expressing human GM-CSF alone, human M-CSF alone, or human GM-CSF and human M-CSF was added to infect them. Similarly, mouse proliferative myeloid cells pMC prepared in Example 4(2) were cultured in a 48-well tissue culture plate, and a suspension of lentivirus expressing mouse GM-CSF alone was added to infect them.

From the next day of the gene transfer, the culture scale was expanded while adding the culture solution according to the proliferation of the cells. Using 20% FBS-containing αMEM as a culture medium, the cells were cultured in the presence of 50 ng/mL GM-CSF and 50 ng/mL human M-CSF. Human GM-CSF was used for the human proliferative myeloid cells pMC, and mouse GM-CSF was used for the mouse proliferative myeloid cells pMC.

The transfected cells self-proliferated due to GM-CSF and M-CSF produced by the cells themselves, even without exogenous addition of the cytokines GM-CSF and M-CSF to the culture medium. The thus-produced pMC with self-proliferation potency was named iPSC-derived professional antigen-presenting cell-GMM (ipAPC-GMM). Similarly, a pMC with self-proliferation potency by GM-CSF produced by the cell itself was named ipAPC-GM, and a pMC with self-proliferation potency by GM-CSF produced by the cell itself was named ipAPC-M.

(3) Examination of Production Amount of Cytokine GM-CSF or M-CSF Introduced into ipAPC-GM, ipAPC-M, ipAPC-GMM (Mouse and Human)

The expression of GM-CSF in the above-mentioned mouse ipAPC-GM, GM-CSF in human ipAPC-GM, M-CSF in ipAPC-M, and GM-CSF and M-CSF in ipAPC-GMM was examined by a flow cytometer. A fluorescent protein, Venus, was expressed via the IRES sequence in the nucleic acid sequence at the 3'-terminal side of the mouse GM-CSF cDNA incorporated into the lentiviral vector. This makes it possible to analyze the expression of GM-CSF in mouse ipAPC-GM by a flow cytometer using Venus fluorescence as an index. A truncated dCD19 without an activation domain was expressed in the nucleic acid sequence at the 3'-terminal side of the human GM-CSF or M-CSF cDNA. This makes it possible to analyze the expression of GM-CSF in human ipAPC-GM, M-CSF in ipAPC-M, and GM-CSF and M-CSF in ipAPC-GMM, using as an index the expression of dCD19 examined using a fluorescence dye-labeled anti-CD19 antibody. FIG. 3 shows the results of the expression of GM-CSF-Venus in mouse pMC and ipAPC-GM, GM-CSF-dCD19 in human pMC and ipAPC-GM, M-CSF-dCD19 in ipAPC-M, and GM-CSF-M-CSF-dCD19 in ipAPC-GMM, as examined by a flow cytometer. It can be seen that mouse ipAPC-GM emits Venus fluorescence, and human ipAPC-GM, ipAPC-M, and ipAPC-GMM express CD19, as compared to pMC before cytokine introduction.

Mouse ipAPC-GM, or human ipAPC-GM, ipAPC-M, ipAPC-GMM was/were cultured using 20% FBS-containing αMEM while maintaining a constant cell density ($1\times10^5$ to $1\times10^6$/mL) and without addition of exogenous cytokines. GM-CSF in the culture supernatant obtained by the aforementioned culture was quantified by Enzyme-Linked Immunosorbent assay (ELISA) method (BioLegend). The results are shown in FIG. 4. While GM-CSF and M-CSF were not produced from the control pMC, mouse ipAPC-GM produced about 150 ng/mL of GM-CSF, human ipAPC-GM and ipAPC-GMM produced about 40 ng/mL of GM-CSF, and human ipAPC-M and ipAPC-GMM produced about 15 ng/mL of M-CSF. Since mouse pMC shows cell proliferation dependent on GM-CSF and human pMC shows cell proliferation dependent on GM-CSF and M-CSF, it was found that mouse ipAPC-GM and human ipAPC-GMM produce GM-CSF or M-CSF sufficient for self-proliferation.

(4) Examination of Self-Proliferation Potency of ipAPC-GM and the Necessity of GM-CSF and M-CSF in Proliferation (Human, Mouse)

Mouse ipAPC-GM obtained as mentioned above, or human ipAPC-GMM derived from on-feeder differentiation induction was collected, seeded in a 96-well tissue culture plate ($2\times10^3$ cells/well), and cultured. The proliferation rate was compared by MTT assay between a culture medium containing 50 ng/mL GM-CSF alone, 50 ng/mL M-CSF alone, or 50 ng/mL GM-CSF and 50 ng/mL M-CSF, and a culture medium not containing any of them.

FIG. 5 shows the measurement results of MTT assay for mouse ipAPC-GM and human ipAPC-GMM. From the results, it was found that ipAPC-GM and ipAPC-GMM proliferate even when GM-CSF and M-CSF are not contained in the culture medium. Therefore, ipAPC-GM and ipAPC-GMM were found to self-proliferate without the addition of cytokines. In addition, exogenous addition of GM-CSF to the culture medium did not promote proliferation. On the other hand, it was found that the addition of 50 ng/mL M-CSF to the culture medium shows the effect of promoting the proliferation of ipAPC-GM and ipAPC-GMM.

(5) Morphology of ipAPC-GM (Mouse)

The mouse ipAPC-GM produced in Example 5(2) showed no change in cell morphology due to the introduction of GM-CSF, and had the morphology of myeloid-like cells with protrusions.

(6) Morphology of ipAPC-GMM and Surface Antigen Analysis of Dendritic Cells (Human)

Similar to mouse ipAPC-GM, human ipAPC-GMM prepared in Example 5(2) showed no change in cell morphology due to the introduction of GM-CSF and M-CSF.

Using 20% FBS-containing αMEM medium containing 50 ng/mL GM-CSF and 50 ng/mL M-CSF, ipAPC-GMM, ipAPC-GM, and ipAPC-M prepared in Example 5(2) were seeded in a 12-well tissue culture plate and cultured. Using cytokine-free 10% FBS-containing RPMI-1640 medium, dendritic cells (DC) were seeded in a 12-well tissue culture plate and cultured for 48 hr. DC was induced by culturing CD14-positive monocytic cells derived from healthy donor blood for 5 days in the presence of 50 ng/mL GM-CSF and 50 ng/mL IL-4. The collected cells were stained with anti-HLA-ABC antibody, anti-HLA-DR antibody, anti-CD40 antibody, anti-CD80 antibody, anti-CD83 antibody, anti-CD86 antibody, anti-CCR7 antibody, anti-CD74 antibody, anti-CD11b antibody, anti-CD11c antibody, anti-CD33 antibody, or isotype-compatible antibody, and analyzed by a flow cytometer.

FIG. 6 shows the results of surface antigen analysis of human ipAPC-GM, ipAPC-M, and ipAPC-GMM. ipAPC-GMM was CD86-, HLA-ABC-, HLA-DR-, CD74-, CD33-positive, CD40-, CD80-low expression, CD11b-, CD11c-low expression to positive, and CD83-, CCR7-negative. Being positive indicates a surface marker intensity ratio (RFI) of 10-fold or more with respect to the mean fluorescence intensity of isotype-compatible antibodies. Low expression indicates RFI of not less than 2-fold and less than 10-fold. Being negative indicates less than 2-fold.

FIG. 7 shows the results of DC surface antigen analysis. DC was found to be positive for all markers except low expression CD83, CCR7. From the results, it can be seen that ipAPC-GM, ipAPC-M, and ipAPC-GMM express antigen-presenting molecules HLA-ABC, HLA-DR, and costimulator molecule CD86, and express, like DC, CD74 important for cross-presentation.

(7) Comprehensive Gene Expression Analysis of Mouse ipAPC-GM

The mouse ipAPC-GM prepared in Example 5(2) was subjected to RNA-seq analysis, which is a whole transcriptome analysis, to quantify the expression of transcription products. Total RNA was extracted from the obtained three types of cells, which were mouse ipAPC-GM, mouse pMC, and mouse pMC added with exogenous GM-CSF, by using the QIAGEN RNeasy mini kit and sequenced using the next generation sequencer BGISEQ (BGI). Then, principal component analysis (PCA) and gene set enrichment analysis (GSEA) were performed.

FIG. 8 shows the results of PCA. This figure plots the profiles of mouse pMC, mouse ipAPC-GM, and GM-CSF-added mouse pMC against two axes (PC1, PC2) with high contribution rates obtained by multivariate analysis. It was found that the gene expression profile of mouse ipAPC-GM was remarkably separated from that of mouse pMC and GM-CSF-added mouse pMC.

FIG. 9 shows the results of GSEA of mouse ipAPC-GM against mouse pMC and GM-CSF-added mouse pMC. It was found that transcripts involved in the cell cycle, its process, cell division and its regulation were detected as gene sets showing remarkably increased expression in mouse ipAPC-GM. Specifically, it was found that the expression of XRCC2, KNTC1, TTK, PKMYT1, AURKA, HMGN5, ANKLE1, KIF2C, MCM8, CDC45, MCM7, CDCA5, CABLES1, CDC6, CDK1, SGOL1, TPX2, NUSAP1, TACC3, UBE2C, MCM5, OSM, UHRF1, CCND1, ABCB1A, APITD1, NSL1, DSCC1, HAUS5, FOXM1, CHEK1, KIF4, BUB1, SKA1, ERCC6L, RECQL4, GINS1, EXO1, CENPN, MKI67, DLGAP5, KIF18A, SYCE2, BIRC5, CDC20, CDC25C, CDKN3, GSG2, CENPH, FAM64A, EPS8, NUP62, RASSF1, KIF20B, CENPT, UTP14B as genes involved in the cell cycle; HAUS5, XRCC2, FOXM1, KNTC1, TTK, AURKA, CHEK1, HMGN5, ANKLE1, KIF2C, CDC45, KIF4, BUB1, SKA1, CDCA5, CABLES1, ERCC6L, RECQL4, GINS1, CDC6, CENPN, CDK1, MKI67, SGOL1, TPX2, KIF18A, NUSAP1, SYCE2, BIRC5, CDC20, CDKN3, UBE2C, TACC3, CDC25C, GSG2, CENPH, OSM, FAM64A, CCND1, ABCB1A, EPS8, NUP62, APITD1, NSL1, RASSF1, KIF20B, CENPT, DSCC1 as genes involved in the cell cycle process; XRCC2, HAUS5, FOXM1, KNTC1, TTK, AURKA, CHEK1, KIF2C, CDC45, KIF4, BUB1, SKA1, CDCA5, CABLES1, ERCC6L, GINS1, CDC6, CDK1, CENPN, MKI67, SGOL1, TPX2, KIF18A, NUSAP1, BIRC5, CDC20, CDKN3, UBE2C, TACC3, CDC25C, GSG2, CENPH, FAM64A, CCND1, ABCB1A, EPS8, NUP62, APITD1, NSL1, KIF20B, CENPT, DSCC1 as genes involved in the mitotic cell division; HAUS5, FOXM1, KNTC1, TTK, AURKA, CHEK1, KIF2C, CDC45, KIF4, BUB1, SKA1, CDCA5, CABLES1, ERCC6L, GINS1, CDC6, CDK1, CENPN, SGOL1, TPX2, KIF18A, NUSAP1, BIRC5, CDC20, CDKN3, UBE2C, TACC3, CDC25C, GSG2, CENPH, FAM64A, CCND1, ABCB1A, EPS8, NUP62, APITD1, NSL1, KIF20B, CENPT, DSCC1 as genes involved in the regulation of mitotic cell division; and the like increase in ipAPC-GM.

(8) Apoptosis Analysis of ipAPC-GM

Cell death of mouse ipAPC-GM, and human ipAPC-GM, ipAPC-M, and ipAPC-GMM produced in Example 5(2), was analyzed using fluorescent label Annexin V and 7-Amino-Actinomycin D (7-AAD). Annexin-V is a protein that specifically binds to phosphatidylserine (PS), which is a phospholipid component of cell membranes. While viable cells do not expose PS on the cell surface, Annexin V binds due to cell membrane reversal caused by apoptosis. 7-AAD permeates dead cells with disrupted cell membranes due to late apoptosis or necrosis, intercalates with DNA strands, and emits red fluorescence. In this way, apoptosis of cells during culture can be analyzed.

Mouse ipAPC-GM and mouse pMC, or human ipAPC-GM, ipAPC-M, ipAPC-GMM, and human pMC were cultured in 20% FBS-containing αMEM without adding exogenous cytokine wherein the cells derived from mouse were cultured for 4 days, and the cells derived from human were cultured for 3 days. The cells cultured under the above-mentioned conditions were sampled every day and analyzed by a flow cytometer after staining with Annexin V and 7-AAD. FIG. 10A shows cytograms showing the analysis results of mouse-derived cells by a flow cytometer. It was found that, on the fourth day of culture (Day 4), mouse ipAPC-GM maintained lower positive rates of Annexin V and 7-AAD, which indicate cell death, than in mouse pMC, which is the control cell. FIG. 10C shows cytograms showing the analysis results of human-derived cells by a flow cytometer. It was found that, on the third day of culture (Day 3), human ipAPC-GMM and ipAPC-M, like mouse ipAPC-GM, maintained lower positive rates of Annexin V and 7-AAD, which indicate cell death, than in human pMC. On the other hand, it was found that human ipAPC-GM has a high frequency of cell death like human pMC. FIG. 10B (cell derived from mouse) and FIG. 10D (cell derived from human) show line graphs of changes over time in the ratios of viable cells, early apoptotic cells, and late apoptotic cells divided into four-quadrant gates of the cytograms. The viable cell rates of mouse ipAPC-GM, human ipAPC-GMM, and human ipAPC-M were high during the culture period, and the ratio of apoptotic cells was maintained low. On the other hand, the viable cell rates of mouse pMC, human pMC, and human ipAPC-GMM started to decrease from the second day of culture and the proportion of apoptotic cells increased. From the above, it was found that mouse ipAPC-GM has higher apoptosis resistance than pMC by introduction of GM-CSF, and human ipAPC-GMM and human ipAPC-M have higher apoptosis resistance than pMC by introduction of M-CSF alone or double introduction of M-CSF and GM-CSF.

Example 6: Examination of Antigen-Presenting Function of ipAPC-GM (1) Proliferation of Alloreactive T Cells by Mouse ipAPC-GM and Human ipAPC-GM, ipAPC-M and ipAPC-GMM In Vitro Using mouse ipAPC-GM prepared from C57BL/6 strain mouse iPSC in the same manner as described above, human ipAPC-GM, human ipAPC-M, and human ipAPC-GMM produced in Example 5(2), allogenic mixed lymphocyte reaction (alloMLR) induction activity was evaluated. Antigen unstimulated naive T cells ($1.5\times10^5$ cells/well) prepared from BALB/c strain mice were cocultured with different strains of C57BL/6 strain-derived mouse ipAPC-GM or mouse pMC for 6 days, [$^3$H]-thymidine (PerkinElmer, 1 μCi/well) was added, and the next day, high-molecular-weight DNA in the cells was captured on a glass filter using a cell harvester (PerkinElmer). Human ipAPC-GM, human ipAPC-M, and human ipAPC-GMM were cocultured with CD3-positive naive T cells derived from peripheral blood mononuclear cells of healthy human donors as the alloMLR-inducing activity, and proliferative activity of human T cells was evaluated. [$^3$H]-Thymidine uptake into high molecular weight DNA was then measured by scintillation counting. [$^3$H]-Thymidine uptake into high molecular weight DNA is proportional to the rate of DNA synthesis, i.e., cell proliferation rate.

FIG. 11 shows the results of scintillation counting of naive T cell stimulation activity. As the ratio of mouse ipAPC-GM to T cells increased, proliferation of alloreactive naive CD8-positive T cells was induced. On the other hand, alloreactive naive T cell proliferation to mouse pMC was weak. Similar to mouse ipAPC-GM, as the ratio of human ipAPC-GM, ipAPC-GMM increased, proliferation of alloreactive naive CD8-positive T cells was induced. On the other hand, alloreactive naive T cell proliferation to human pMC, ipAPC-M was weak. From the above results, it can be seen that the effect of the cytokine GM-CSF introduced into ipAPC-GM and ipAPC-GMM enhances the immune response by pMC.

(2) Examination of Proliferation of Antigen-Specific CD8-Positive T Cells In Vitro by ipAPC-GM Loaded with Peptides and Proteins Generally, antigen-presenting cells take up extracellular antigens, and after a processing process to degrade them into peptides, present peptide antigens to CD4-positive T cells via major histocompatibility complex (MHC) class II antigen-presenting molecules. Special antigen-presenting cells such as dendritic cells (DC) and the like have the function of presenting the extracellular antigens taken up to CD8-positive T cells via MHC class I molecules. Such mechanism is called cross-presentation. Using ovalbumin (DQ-OVA) that emits green fluorescence when taken up into cells and digested into peptides, due to labeling with a self-quenching fluorescent dye, the antigen uptake capacity of human ipAPC-GM, ipAPC-M, and ipAPC-GMM produced in Example 5(2) was examined. Using ovalbumin (OVA) and OVA-specific T cells, cross-presentation by mouse ipAPC-GM was examined.

Human ipAPC-GM, ipAPC-M, and ipAPC-GMM produced in Example 5(2) were seeded in a 24-well tissue culture plate at $5\times10^4$ cells/well, and the ipAPC-GM, ipAPC-M, and ipAPC-GMM were loaded with 10 μg/mL DQ-OVA and incubated at 37° C. for 4 hr. A sample incubated at 4° C. was also prepared as a negative control without antigen uptake. The frequency of antigen uptake was compared with the DC of biological origin induced in Example 5(6). Then, the mouse ipAPC-GM produced from the C57BL/6 strain mouse iPSC described in Example 6(1) was seeded in a 96-well tissue culture plate at $5\times10^4$ cells/well, and the ipAPC-GM was loaded with OVA peptide $OVA_{257-264}$ or OVA protein in a concentration-dependent manner, and proliferation of ipAPC-GM was stopped by radiation irradiation (85 Gy). Then, they were cocultured for 4 days with naive CD8-positive T cells OT-1 ($1\times10^4$ cells/well) having OVA-specific T cell receptor (TCR).

The results of measuring DQ-OVA intracellular uptake by a flow cytometry are shown in FIG. 12A (left), and the results of measuring OT-1 proliferation by [$^3$H]-thymidine uptake are shown in FIG. 12A (right). Human ipAPC-GM, ipAPC-M, and ipAPC-GMM were found to take up antigen at a high frequency of about 95%, similar to pMC before cytokine introduction. On the other hand, the frequency of antigen uptake in DC of biological origin was about 75%. Mouse ipAPC-GM was loaded with OVA peptide $OVA_{257-264}$ or OVA protein in a concentration-dependent manner, and proliferation of ipAPC-GM was stopped by radiation irradiation. Then, they were cocultured with naive CD8-positive T cells OT-1 having OVA-specific T cell receptor (TCR). The in vitro proliferation of antigen-specific CD8-positive T cells was quantified by scintillation counting of [$^3$H]-thymidine uptake. A plot of the results is shown in FIG. 12B. Mouse ipAPC-GM induced OT-1 proliferation in a manner dependent on the concentrations of OVA peptide and protein. FIG. 13 shows the comparison results of the OT-1 proliferation-inducing activity between mouse ipAPC-GM and mouse pMC under conditions loaded with 10 μM OVA peptide or 100 μg/mL OVA protein. From the above results, human ipAPC-GM, ipAPC-M, and ipAPC-GMM were superior to DC in the frequency of antigen uptake, and mouse ipAPC-GM was superior to mouse pMC in the antigen-specific T cell proliferation-stimulating activity.

(3) Induction of Antigen-Specific Cancer-Reactive T Cells In Vivo

Using a mouse preventive model, the in vivo antigen-specific T cell stimulation activity of ipAPC-GM was examined. To the C57BL/6 strain mice were intraperitoneally administered $1\times10^5$ cells of the mouse ipAPC-GM produced from the C57BL/6 strain mouse iPSC described in Example 6(1) or mouse pMC alone, or mouse ipAPC-GM or mouse pMC loaded with OVA peptide or OVA protein twice every 7 days, and melanoma-derived OVA-expressing cancer cells (MO4) ($2\times10^5$ cells) were inoculated to the mice by subcutaneous injection. Five days after inoculation when the tumor diameter reached 2 to 3 mm, the tumor diameter of the mice in the mouse ipAPC-GM or mouse pMC administration group and the control group was measured twice a week. It was continued until the mouse died or the tumor diameter reached 20 mm.

FIG. 14 shows the time-course changes of the inoculated tumor volume. ipAPC-GM significantly suppressed an increase in the tumor volume. The suppressive effect was higher in ipAPC-GM than in pMC, and was more remarkable in both ipAPC-GM and pMC when loaded with OVA peptide or OVA protein.

FIG. 15 shows the survival curve of mice inoculated with cancer cells. Corresponding to the aforementioned measurement results of the tumor volume, the group administered with ipAPC-GM loaded with OVA peptide or OVA protein remarkably showed a significant extension of survival compared with the group administered with pMC similarly loaded with OVA peptide or OVA protein.

FIG. 16 shows the results of in vitro detection of splenic OVA peptide antigen-specific T cells on day 56 after inoculation. CD8-positive T cells were separated from the collected peripheral blood mononuclear cells by using anti-CD8 antibody-coated beads. The obtained cells were stimulated with the OVA peptide or the control SIY peptide, and 36 hours later, the frequency of antigen-specific T cells was analyzed by Enzyme-Linked ImmunoSpot (ELISPOT) assay for detecting interferon γ. OVA-specific T cells were highly frequently detected in the mice of the ipAPC-GM-treated group. Based on the above, it was found that the ipAPC-GM of the present invention has the function of presenting desired antigens such as cancer antigen and the like to CD8-positive T cells, and furthermore, proliferate the CD8-positive T cells having antigen-specific T-cell receptors.

Example 7: Induction of Homeostatic Expansion of CD8-Positive T Cells by ipAPC-GM (1) Promotion of Proliferation of Naive T Cells by GM-CSF and ipAPC-GM Culture Supernatant The influence of GM-CSF produced by mouse ipAPC-GM produced in Example 5 on the proliferation of naive OT-1 CD8-positive T cells was examined. Naive OT-1

CD8-positive T cells ($1\times10^5$ cells/well) were cultured for 6 days in the presence of various concentrations of gene recombinant GM-CSF protein or ipAPC-GM culture supernatant. In addition, the contribution of GM-CSF was verified by adding an anti-GM-CSF neutralizing antibody to the ipAPC-GM culture supernatant. The proliferation of T cells was evaluated by [$^3$H]-thymidine uptake.

As a result of culturing naive OT-1 CD8-positive T cells in the presence of various concentrations of recombinant GM-CSF, T cell proliferation occurred in a GM-CSF concentration-dependent manner, and at least 1.5 ng/mL GM-CSF was necessary. FIG. 17 shows the evaluation results of T cell proliferation in the presence of ipAPC-GM or pMC culture supernatant. While the ipAPC-GM culture supernatant promoted T cell proliferation, the pMC culture supernatant did not show a similar effect. FIG. 18 shows the evaluation results of T cell proliferation when an anti-GM-CSF neutralizing antibody was added to the ipAPC-GM culture supernatant. The anti-GM-CSF antibody inhibited the T cell proliferative activity of the ipAPC-GM culture supernatant. From the above, it was also found that ipAPC-GM not only induces antigen-specific T cells, but also promotes proliferation of CD8-positive naive T cells by GM-CSF secreted by the cells. Particularly, it was found that 1.5 ng/mL or more of GM-CSF was necessary for homeostatic expansion of CD8-positive naive T cells.

(2) Promotion of Proliferation of Naive T Cells Cocultured with ipAPC-GM

Mouse ipAPC-GM or mouse pMC ($5\times10^4$ cells), whose cell proliferation had been stopped by 85 Gy radiation irradiation, of mouse ipAPC-GM produced in Example 5 were cocultured for 4 days with naive CD8-positive T cells prepared from C57BL/6 strain mouse, and T cell proliferation was evaluated by [$^3$H]-thymidine uptake. FIG. 19 shows the proliferative activity of T cells cocultured with ipAPC-GM or pMC. It can be seen that coculture with ipAPC-GM caused remarkable proliferation of T cells. It can be seen that the T cell proliferation promoting effect of ipAPC-GM is significantly higher than that of pMC. FIG. 20 shows the flow cytometer analysis results of T cell receptor (TCR) Vβ frequency of naive CD8-positive T cells before and after coculture with ipAPC-GM. It can be seen that coculture with ipAPC-GM does not affect specific TCR clone, but promotes homeostasis expansion of polyclonal T cells.

Example 8: Regulation of Pharmacokinetics (Disappearance from the Body in 3 to 4 Days) while Maintaining Antigen-Presenting Ability by Radiation Irradiation on ipAPC-GM (1) Apoptosis Analysis of ipAPC-GM Irradiated with 85 Gy Radiation As described above in Example 5(7) and (8), it was found that ipAPC-GM shows active cell division due to GM-CSF it produces, and has improved survival ability compared with pMC. While the high self-proliferation potency of ipAPC-GM is useful in producing cells in the number required for treatment, tumorigenicity after administration in vivo is feared. As described in Non Patent Literature Science 311, 1160-1164, ipAPC-GM needs to survive in vivo for several days after transplantation in order for the antigen-presenting cells to activate CD8-positive T cells, but is desirably cleared rapidly thereafter. In order to solve this problem, ipAPC-GM was irradiated with radiation, and the influence on the self-proliferation potency was examined.

Mouse ipAPC-GM prepared in Example 5 and mouse pMC were irradiated with 65, 85, or 100 Gy radiation, and cultured for 4 days at 37° C. and 5% CO2 using 20% FBS-containing αMEM in the absence of cytokines. Human pMC, ipAPC-GM, ipAPC-M, and ipAPC-GMM were irradiated with 2.5, 5, 10, 20, 40, 80 Gy radiation, and cultured for 6 days in the presence of cytokines, 50 ng/mL GM-CSF, and 50 ng/mL M-CSF. The cell morphology thereof is shown in FIG. 21. ipAPC-GM retained its cell morphology even after radiation irradiation. On the other hand, most of the control pMCs were destroyed by radiation irradiation and suffered cell injury. FIG. 22 shows evaluation results of the cell proliferation of mouse ipAPC-GM, human pMC, ipAPC-GM, ipAPC-M, and ipAPC-GMM after radiation irradiation by [$^3$H]-thymidine uptake activity. Both mouse ipAPC-GM and pMC showed significantly suppressed cell proliferation at any irradiation dose. In human pMC, ipAPC-GM, ipAPC-M, and ipAPC-GMM, cell proliferation stopped at 20 Gy or more, whereas cell proliferation was observed at low irradiation doses of 10 Gy or less. From the above results, it was found that cell proliferation of human ipAPC-GM, ipAPC-M, and ipAPC-GMM can be controlled by radiation irradiation of 20 Gy or more.

Mouse ipAPC-GM produced in Example 5 were seeded in a 96-well plate and irradiated with 85 Gy radiation, and mouse ipAPC-GM and mouse pMC ($1\times10^5$ cells) were stained with Annexin V and 7-AAD, and analyzed by a flow cytometer to analyze in vitro survival rate. FIG. 23 shows the flow cytometer analysis results. At 24 hr after 85 Gy irradiation, the main cell population of ipAPC-GM became negative for both Annexin V and 7-AAD and survived. In contrast, most pMC became positive for both Annexin V and 7-AAD reagents and apoptosis was observed.

(2) Examination of Cell Proliferation Potency of ipAPC-GM Irradiated with Radiation FIG. 24 shows the evaluation results of the cell proliferation in vitro of mouse ipAPC-GM produced in Example 5 or mouse pMC ($2\times10^4$ cells/well) seeded in a 96-well plate and irradiated with radiation at 85 Gy, by MTT assay continuously for 3 days after irradiation. The 85 Gy radiation irradiation suppressed proliferation of ipAPC-GM seen in non-irradiated cells (0 Gy). In pMC, the radiation irradiation caused a significant decrease in the MTT activity. The results are consistent with the results of FIG. 21 in which pMC was disrupted by cell injury due to radiation irradiation.

(3) Pharmacokinetics of ipAPC-GM Irradiated with Radiation

A lentiviral vector that expresses luciferase as a reporter gene was introduced into the mouse ipAPC-GM prepared in Example 5. Similarly, mouse pMC with luciferase gene introduced thereinto was also produced. Cells expressing the luciferase gene emit biochemiluminescence upon addition of luminescent substrate luciferin. This makes it possible to optically examine the pharmacokinetics of ipAPC-GM administered in vivo.

Luciferase-expressing ipAPC-GM or pMC ($1\times10^6$ cells) irradiated with 85 Gy radiation was subcutaneously administered to C57BL/6 strain mice. Cell viability of ipAPC-GM and pMC in vivo was measured by biochemiluminescence with an IVIS imaging system (PerkinElmer) every other day. FIG. 25 shows the photographed images of in vivo imaging and the time course zo changes of the total flux of luciferase luminescence. Immediately after administration, ipAPC-GM or pMC was detected as a clear luminescence signal locally at the transplanted site, and disappeared with the passage of days. ipAPC-GM was retained in the body for 3 days after subcutaneous administration to mice, and disappeared on the 4th day. In contrast, pMC mostly disappeared from the body on the next day after administration.

From the above, it was found that the ipAPC-GM of the present invention exists in the body for 3 days after administration to the body even after radiation irradiation, and disappears after 4 days. From this, it was found that ipAPC-GM disappears in 3 to 4 days after administration when administered into the body after radiation irradiation.

(4) In Vivo Cross-Presentation Ability of ipAPC-GM that Received Radiation Irradiation The mouse ipAPC-GM produced in Example 5 and pMC were subjected to radiation irradiation to stop proliferation so potency, loaded with OVA peptide, and intraperitoneally administered to C57BL/6 strain mice. Cancer cell MO4 was subcutaneously inoculated, and the tumor diameter and viability of the mice were evaluated every 3 to 4 days. A comparative test was performed using bone marrow-derived dendritic cells (BM-DC) free of radiation irradiation as a positive control, and an untreated group as a negative control. An ELISPOT assay for interferon-γ was performed 54 days after MO4 inoculation.

FIG. 26 shows changes in tumor volume. The ipAPC-GM administration group significantly suppressed tumor growth compared to the untreated group and pMC administration group. The tumor suppressive effect of ipAPC-GM was comparable to that of the bone marrow-derived dendritic cells (BM-DC) as the positive control.

FIG. 27 shows survival curves of mice. The ipAPC-GM administration group showed significantly extended survival of mice compared with the untreated group. It was found that the survival extending effect by ipAPC-GM administration was not significantly different from that of BM-DC and pMC.

FIG. 28 shows the ELISPOT assay results. The ipAPC-GM administration group remarkably induced CD8-positive T cells specific to OVA, which is a cancer antigen, as compared with the untreated and pMC administration groups. It was found that the induction of cancer-specific CD8-positive T cells by ipAPC-GM was equivalent to that of BM-DC.

From the above, it was found that, even after radiation irradiation, the ipAPC-GM of the present invention has the function of presenting desired antigens such as cancer antigen and the like to CD8-positive T cells, and furthermore, proliferate the CD8-positive T cells having desired antigen-specific T-cell receptors.

Example 9: Regulation of Pharmacokinetics by Introducing Suicide Gene into ipAPC-GM A lentiviral vector that expresses HSV-TK or iCasp9 as a suicide gene was introduced into the mouse ipAPC-GM prepared in Example 5. HSV-TK-introduced ipAPC-GM is indicated as ipAPC-GM-HSV-TK, and iCasp9-introduced ipAPC-GM is indicated as ipAPC-GM-iCasp9. A lentiviral vector that expresses luciferase as a reporter gene was further introduced into ipAPC-GM-HSV-TK or ipAPC-GM-iCasp9, and ipAPC-GM-HSV-TK and ipAPC-GM-iCasp9 administered in vivo was investigated optically. Luciferase-introduced cells are indicated as ipAPC-GM-Luc, ipAPC-GM-HSV-TK-Luc, or ipAPC-GM-iCasp9-Luc. ipAPC-GM expressing luciferase and suicide genes or ipAPC-GM expressing only luciferase gene ($1\times10^6$ cells) were subcutaneously administered to C57BL/6 strain mice. Subsequently, 100 mg/kg of GCV, which is a suicide gene HSV-TK induction reagent, or 2.5 mg/kg of AP1903, which is an iCasp9 induction reagent, was administered intraperitoneally for five consecutive days from the day of administration (Day 0) to the fourth day (Day 4). Cell viability of ipAPC-GM-HSV-TK, ipAPC-iCasp9, and ipAPC-GM in vivo was measured by biochemiluminescence with an IVIS imaging system (PerkinElmer) every other day.

FIG. 29 shows time-course changes in the total flux of luciferase luminescence obtained from the photographed images of in vivo imaging. All of HSV-TK introduction, iCasp9 introduction, and suicide gene-free ipAPC-GM were detected as clear luminescence signals locally at the transplanted sites, and the signals decreased with the passage of days. In mice of the ipAPC-GM-Luc administration group, no significant decrease in the signal due to the administration of GCV or AP1903 was observed, whereas the signal of cells retained in vivo significantly decreased due to the administration of GCV or AP1903 and completely disappeared on day 7 after transplantation in the ipAPC-HSV-TK-Luc administration group or ipAPC-GM-iCasp9-Luc administration group.

FIG. 30 shows the effect of the combined use of the suicide gene iCasp9 and 5 mg/kg YM-155, which is an inhibitor of anti-apoptotic factor Survivin. In mice to which ipAPC-GM-iCasp9-Luc was administered, administration of 5 mg/kg YM-155 alone showed a signal attenuation process similar to that of physiological saline (Medium), whereas a significant decrease in the signal was observed the day after cell transplantation when administered in combination with AP1903 compared to AP1903 alone. From the result, it was found that by using AP1903 in combination with YM-155, apoptosis of the suicide gene iCasp9 of the transplanted cells was induced at an early stage, and a rapid cell removal effect was obtained. It was also found that ipAPC can be rapidly removed by using a suicide gene and an anti-apoptotic factor in combination.

Example 10: Examination of Safety of In Vivo Administration of ipAPC-GM (1) Measurement of Blood Cytokine in ipAPC-GM-Administered Mouse Mouse ipAPC-GM prepared in Example 5 was administered alone twice at 7 day intervals, and blood cytokine was measured on the day after the second administration. A group administered with 4.0 mg/kg of lipopolysaccharide (LPS) was compared as a positive control. In ipAPC-GM-administered mice, no increase in blood levels of IL-6, TNFα, and GM-CSF was observed, and no inflammation was induced in vivo.

(2) Variation in Blood Cell Fraction in ipAPC-GM-Administered Mouse

Mouse ipAPC-GM prepared in Example 4(2) was administered and the variation in leukocyte fraction was examined after the administration (the next day) by a flow cytometry. The frequency of cell populations such as T cells (B220−/CD3+), B cells (B220+/CD3−), myeloid cells (CD11b+/Gr-1−), myeloid-derived suppressor cells (CD11b+/Gr-1+), and the like did not change significantly by ipAPC-GM administration and there was no influence on leukocyte fraction.

Example 11: Comparison of Effect of ipAPC-GM and Immune Checkpoint Inhibitor

The antitumor effects of immune checkpoint inhibitor (ICI) known as an existing cancer immunotherapy and ipAPC-GM were compared, and the effect of the combined use of ICI and ipAPC-GM was examined. ipAPC-GM, or ICI (anti-CTLA-4 antibody and anti-PD-L1 antibody), or ipAPC-GM and ICI in combination were intraperitoneally administered to mice inoculated with tumor cells by subcutaneous injection. The tumor diameter and viability of the mice were evaluated every 3 to 4 days. An antitumor effect on immune checkpoint inhibitor (ICI)-low-sensitive cancer cell MO4 tumor is shown in FIG. 31. As a cancer antigen for MO4 tumor, $OVA_{257-264}$ peptide was loaded on ipAPC-GM. ipAPC-GM significantly suppressed tumor growth compared with treatment with ICI alone and extended the survival of mice. Furthermore, the combined use of ICI and ipAPC-GM tended to suppress tumor growth and extend the survival of mice more than the administration of ipAPC-GM alone.

An antitumor effect on ICI-sensitive cancer cell MC38 tumor is shown in FIG. 32. As a cancer antigen for MC38 tumor, mutant Adpgk (mAdpgk) peptide was loaded on ipAPC-GM, and as a negative control for cancer antigen, wild-type Adpgk (wtAdpgk) peptide was loaded on ipAPC-GM. Compared with wtAdpgk peptide-loaded ipAPC-GM, mAdpgk peptide-loaded ipAPC-GM treated group did not show a significant difference but showed a tendency to suppress an increase in the tumor diameter, and significantly prolonged the survival of mice. Compared with ICI alone treatment, no significant difference was found in the time-course changes in the tumor size and survival of mice by mAdpgk peptide-loaded ipAPC-GM. When ICI and mAdpgk peptide-loaded ipAPC-GM were used in combination, no significant difference was found from ICI alone, but an increase in the tumor diameter was significantly suppressed and mouse survival was prolonged more than ipAPC-GM alone treatment.

Example 12: Influence of ipAPC-GM on Myeloid-Derived Suppressor Cells (MDSC) in Tumor The influence of combined use of immune checkpoint inhibitor (ICI) known as an existing cancer immunotherapy and ipAPC-GM on myeloid-derived suppressor cells (MDSC) in tumor is shown in FIG. 33. Mice with subcutaneous tumor of ICI-low-sensitive cancer cell MO4 prepared in advance were subjected to a treatment with ipAPC-GM or a combined treatment with ICI (anti-CTLA-4 antibody+anti-PD-L1 antibody) and ipAPC-GM, and myeloid-derived suppressor cells (MDSC) in the tumor after treatment were evaluated by a flow cytometry. Since MDSC suppresses immune responses, it is considered to be a factor that makes the treatment of cancer immunotherapy resistant. It was found that the proportion of MDSC in the tumor significantly decreased to 12.1% by a treatment with ipAPC-GM alone, and 4.33% by a treatment with ipAPC-GM in combination with ICI, compared with 15.5% in untreated tumor tissue.

Example 13: Influence of ipAPC-GM on CD8-Positive T Cells in Tumor

FIG. 34 shows the evaluation results by a flow cytometry for CD8-positive T cells in the tumor after treatment in Example 11. Perforin and granzyme (GzmB) are cytotoxic granules secreted by CD8-positive T cells that have recognized antigen peptides. Perforin polymerizes and opens pores on the target cancer cell membrane, and GzmB enters the target cancer cells through the pores and causes cell death. Administration of ipAPC-GM increased the number of Perforin- and GzmB-expressing CD8-positive T cells in the tumor from 0.52% to 6.19% compared with no treatment, which further increased to 12.3% by a combined treatment of ipAPC-GM and ICI (anti-CTLA-4 antibody+anti-PD-L1 antibody). A decrease in MDSC and an increase in both Perforin- and GzmB-positive CD8-positive T cells in the tumor are considered to contribute to the antitumor effect of ipAPC-GM. Moreover, from the result, it was found that the combined use of ipAPC-GM and various ICIs can exhibit a greater antitumor effect.

Comparative Example 1: Feeder-Free Differentiation Induction Culture of Human iPSC The differentiation induction of Example 3(4) was compared with the differentiation induction method described in Non Patent Literature (Gene Therapy 2011 18, 874-883). Human EBs produced from human iPSC were seeded in a recombinant human fibronectin-coated tissue culture 12-well plate and statically cultured overnight in a StemFit medium at 37° C. in a 5% $CO_2$ incubator. The iPSC colonies adhered to the plate were cultured for 10 days in the presence of 50 ng/mL BMP-4 in a 1:1 mixture of AIM-V (Life Technologies) and X-VIVO15 (Lonza) as a differentiation induction medium. Furthermore, the colonies were cultured in X-VIVO15 for 14 days in the presence of 50 ng/mL BMP-4. The obtained cells were detached and collected using TripLE (Life Technologies), seeded on a low-adhesion plate (Corning), and cultured for 7 days in X-VIVO15 in the presence of 50 ng/mL GM-CSF and 50 ng/mL M-CSF to obtain differentiated cells. Differentiated cells on day 18 and day of culture were used as samples, and the expression of hematopoietic differentiation marker CD34 and CD43 antibodies or myeloid differentiation markers CD11b and CD11c was examined by a flow cytometry.

The differentiated cells were collected by a pipetting operation and stained with an anti-CD11b antibody, an anti-CD11c antibody, an anti-CD34 antibody, an anti-CD43 antibody, or an isotype-compatible control antibody. The cells were then washed twice with 2% FBS-containing PBS or PBS. The cells after washing were analyzed using a flow cytometer analyzer. FIG. 35 shows the results of surface antigen analysis by a flow cytometer after antibody staining. From the results of this analysis, it was found that the differentiated cells produced in Example 3(4) showed the frequency of hematopoietic differentiation marker CD34-positive cells of 19.4% on day 18 of differentiation induction. On day 25, the frequency of myeloid differentiation marker CD11b-positive cells was 48.3%.

The differentiated cells (Comparative Example 1) produced by the differentiation induction method described in Non Patent Literature (Gene Therapy 2011 18, 874-883) were negative for the hematopoietic differentiation marker CD34 on day 18 of differentiation induction. Thereafter, the cells died and the number of recovered cells was remarkably small. At day 25, they were negative for the myeloid differentiation marker CD11b. From the result, it was found that the referenced differentiation induction protocol was not reproducible and had poor differentiation induction efficiency.

INDUSTRIAL APPLICABILITY

The pluripotent stem cell-derived human professional antigen-presenting cell of the present invention has the ability to proliferate in vitro and antigen-presenting ability comparable to that of DC of biological origin, and therefore, achieves stable supply as a cell preparation.

The invention claimed is:

1. A method for producing a professional antigen-presenting cell (pMC), comprising differentiating myeloid cells (MC) from a pluripotent stem cell by the following method (i) or (ii):

(i) performing a double-laver culture of embryoid body (EB) induced from the pluripotent stem cells on feeder cells in a medium containing vascular endothelial growth factor (VEGF), and further culturing same in a medium containing VEGF, stem cell factor (SCF), and thrombopoietin (TPO), or (ii) performing a monolayer culture of an embryoid body (EB) induced from the pluripotent stem cells in a medium containing bone morphogenetic protein 4 (BMP-4), VEGF, and SCF without feeder cells, and further culturing same in a medium containing VEGF, TPO, and granulocyte-macrophage colony-stimulating factor (GM-CSF), inducing expression of Myc proto-oncogene protein (c-MYC), polycomb complex protein BMI-1 (BMI1), and E3 ubiquitin-protein ligase Mdm2 (MDM2) in a myeloid cell (MC) to obtain a proliferative myeloid cell (pMC), and inducing expression of GM-CSF and/or Macrophage colony-stimulating factor (M-CSF) in the pMC to obtain a professional antigen-presenting cell (pAPC).

2. The method according to claim 1, further comprising forming an embryoid body (EB) from the pluripotent stem cell by the following method:

(i) seeding the pluripotent stem cells in a container for cell mass-forming culture to form an embryoid body (EB), wherein the container has fine spheroid wells at a bottom, and does not have a flat surface between adjacent wells.

3. A method for producing a professional antigen-presenting cell, comprising (i) seeding pluripotent stem cells in a container for cell mass-forming culture that has fine spheroid wells at a bottom, and does not have a flat surface between adjacent spheroid wells to form an embryoid body (EB), (ii) obtaining myeloid cells (MC) from the embryoid body (EB) by the method of the following (ii)-1 or (ii)-2:

(ii)-1 performing a double-layer culture of the embryoid body on feeder cells in a medium containing VEGF, and further culturing same in a medium containing VEGF, SCF, and TPO, or (ii)-2 performing a monolayer culture of the embryoid body in a medium containing BMP-4, VEGF, and SCF without feeder cells, and further culturing same in a medium containing VEGF, TPO, and GM-CSF, (iii) inducing expression of c-MYC, BMI1, and MDM2 in the myeloid cells (MC) obtained in (ii) to obtain proliferative myeloid cells (pMC), and (iv) inducing expression of GM-CSF and/or M-CSF in the proliferative myeloid cells (pMC) obtained in (iii) to obtain professional antigen-presenting cells (pAPC).

4. The method according to claim 3, wherein the c-MYC, BMI1, and MDM2 are provided by transfection into myeloid cells (MC), and GM-CSF and/or M-CSF are/is provided by transfection into proliferative myeloid cells (pMC).

5. The method according to claim 1, wherein the embryoid body (EB) has a size of 50 to 200 μm.

* * * * *